(12) United States Patent  
Kimura

(10) Patent No.: US 6,613,313 B2  
(45) Date of Patent: Sep. 2, 2003

(54) ANILINE COMPOUND-CONTAINING HAIR DYE COMPOSITION AND METHOD OF DYEING HAIR

(75) Inventor: Keizo Kimura, Minami-Ashigara (JP)

(73) Assignee: Fuji Photo Film Co., Ltd., Minami-Ashigara (JP)

(*) Notice: Subject to any disclaimer, the term of this patent is extended or adjusted under 35 U.S.C. 154(b) by 0 days.

(21) Appl. No.: 09/200,733

(22) Filed: Nov. 27, 1998

(65) Prior Publication Data

US 2002/0197223 A1 Dec. 26, 2002

(30) Foreign Application Priority Data

Nov. 28, 1997 (JP) .............................................. 9-328129  
Nov. 28, 1997 (JP) .............................................. 9-328130  
Dec. 1, 1997 (JP) .............................................. 9-329998

(51) Int. Cl.$^7$ ...................... A61K 7/13; A61K 31/047; A61K 31/075; A61K 31/136; A61K 31/395

(52) U.S. Cl. .............................. 424/70.1; 8/405; 8/416; 514/210.01; 514/277; 514/279; 514/299; 514/359; 514/408; 514/410; 514/412; 514/415; 514/656; 514/657; 514/718; 514/727; 514/730

(58) Field of Search .................. 424/70.1; 514/277, 514/279, 299, 359, 408, 410, 412, 415, 210.01, 656, 657, 718, 727, 730; 8/405, 416

(56) References Cited

U.S. PATENT DOCUMENTS

| | | | | |
|---|---|---|---|---|
| 3,630,655 A | * | 12/1971 | Berth ............................ | 8/409 |
| 5,190,564 A | * | 3/1993 | Lang et al. .................... | 8/423 |
| 5,427,588 A | * | 6/1995 | Lagrange et al. ............. | 8/423 |
| 5,583,234 A | * | 12/1996 | Lagrange et al. ........... | 548/455 |
| 5,773,206 A | | 6/1998 | Hershey et al. ............. | 430/442 |
| 5,876,464 A | * | 3/1999 | Lim et al. ...................... | 8/409 |
| 5,993,491 A | * | 11/1999 | Lim et al. ...................... | 8/409 |
| 5,994,546 A | * | 11/1999 | Kimura et al. .............. | 546/165 |
| 6,043,006 A | * | 3/2000 | Kimura et al. .............. | 430/380 |
| 6,169,206 B1 | * | 1/2001 | Kimura et al. .............. | 564/443 |

FOREIGN PATENT DOCUMENTS

JP    9-20628    1/1997

OTHER PUBLICATIONS

Rose et al.,'Hair coloring composition'(DE 2716671 A1 (1978)), STN/CAS online, file CAPLUS, Abstract.*  
Abstract of Japanese Patent Document No. JP 9–020628 (4 pages).

* cited by examiner

Primary Examiner—Jose' G. Dees  
Assistant Examiner—Frank Choi  
(74) Attorney, Agent, or Firm—Burns, Doane, Swecker & Mathis, LLP

(57) ABSTRACT

A hair dye composition containing at least one of the following compounds:

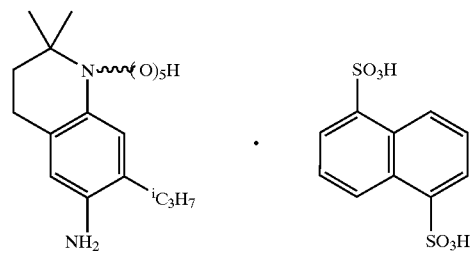

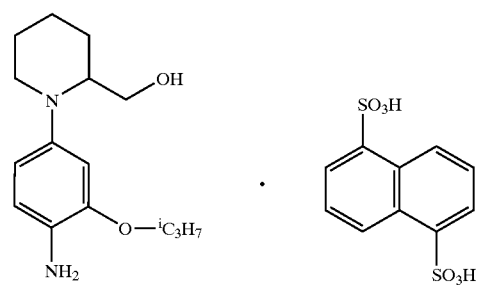

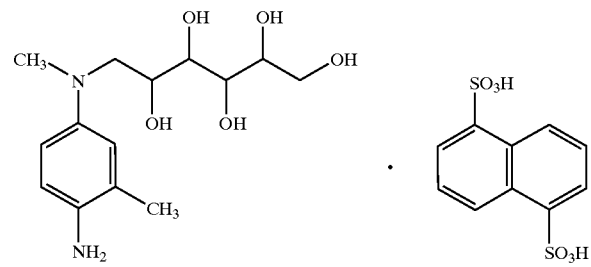

or analogues thereof; and a method for dyeing hair which comprises a step of applying to the hair the hair dye composition is used. The dye composition of the invention exhibits excellent spreadability, applicability, level-dyeing property and shampoo resistance.

6 Claims, No Drawings

ANILINE COMPOUND-CONTAINING HAIR DYE COMPOSITION AND METHOD OF DYEING HAIR

BACKGROUND OF THE INVENTION

The present invention relates to a hair dye composition containing an aniline compound. In particular, the present invention relates to an oxidation hair dye composition which exhibits excellent spreadability, applicability, level-dyeing property and shampoo resistance. The present invention also relates to a method of dyeing hair with the hair dye composition.

Hair dyes are classified into groups of temporary hair colorants, semipermanent hair dyes and permanent hair dyes. The oxidation hair dyes are the most widely used among the permanent hair dyes. When a hair dye of this kind is applied to hair, the oxidative polymerization occurs to develop a color after the oxidation dye in the hair dye composition penetrates into hair and, as a result, the hair is chemically dyed. Therefore, the hair dye of this kind has a strong dyeing power and the color lasts for a long time. The oxidation hair dyes are usually of two-pack type to be used by mixing a first pack containing an oxidation dye with a second pack containing an oxidizing agent at the time of use and applying the obtained mixture to hair. However, the oxidation hair dyes of one-pack type which is in the form of a powder to be mixed with water at the time of the use, and three- or more-pack type are available. In any case, the oxidation hair dyes chemically dye hair by the oxidative polymerization reaction. Therefore, when the applicability of the oxidation hair dye to hair is insufficient, dyeing specks are easily formed. To prevent the formation of the dyeing specks, various ideas were proposed hitherto. For example, a solvent, a dispersion medium or the like is incorporated into the oxidation hair dye composition to improve the fluidity thereof so that the hair dye can be rapidly and uniformly applied to hair; or an improved thickening agent is used as described in Japanese Patent Unexamined Published Application (hereinafter referred to as "J. P. KOKAI") No. Hei 9-20628. However, a further improvement is demanded. In particular, a further improvement in the fastness is demanded so that the dyed hair is not decolored even after repeating the shampoo many times.

SUMMARY OF THE INVENTION

Therefore, an object of the present invention is to provide an oxidation hair dye composition excellent in spreadability, applicability, level-dyeing property and shampoo resistance.

Another object of the invention is to provide a method of dyeing hair with the oxidation hair dye composition.

The present invention provides a hair dye composition containing at least one of the compounds of the following general formulae (I) to (V):

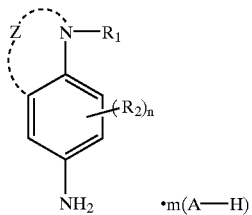

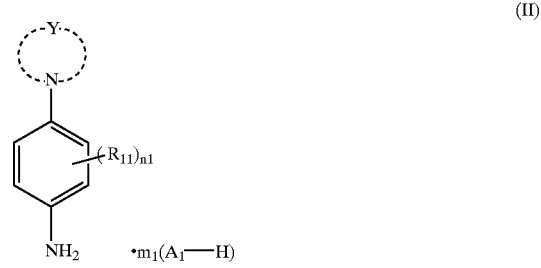

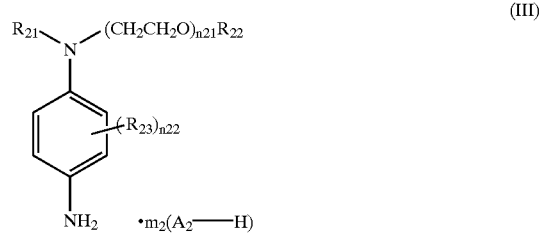

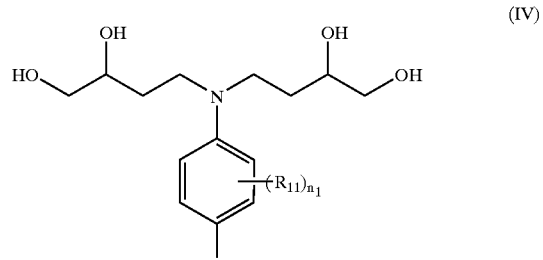

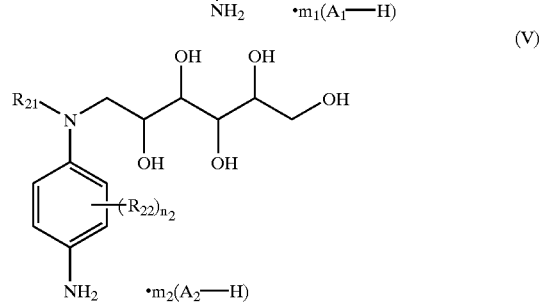

In formula (I), $R_1$ represents an alkyl group, aryl group or heterocyclic group, $R_2$ represents a substituent and Z represents an ethylene group or trimethylene group. When $R_1$ is an alkyl or aryl group, at least one of $R_1$ and Z is substituted by a substituent containing at least one of nitrogen atom, oxygen atom and sulfur atom. n represents 0 or an integer of 1 to 3. When n is 2 or higher, $R_2$'s may be the same or different or they may form a ring. A represents an acid radical or, in other words, A-H is an acid, and m represents 0 or a positive integer.

In formula (II), $R_{11}$ represents a substituent, and Y represents a tetramethylene, pentamethylene or hexamethylene group substituted by a substituent containing at least one of nitrogen atom, oxygen atom and sulfur atom. $n_1$ represents 0 or an integer of 1 to 4. When $n_1$ is 2 or higher, $R_{11}$'s may be the same or different or they may form a ring. A part of Y and $R_{11}$ do not form a ring together. $A_1$ represents an acid radical or, in other words, $A_1$-H is an acid, and $m_1$ represents 0 or a positive integer.

In formula (III), $R_{21}$ represents an alkyl, aryl or heterocyclic group, $R_{23}$ represents a hydrogen atom or an alkyl, aryl or heterocyclic group, and RZ3 represents a substituent. $n_{Z1}$ represents an integer of 2 to 8, and $n_{Z2}$ represents 0 or an integer of 1 to 4. When $n_{Z2}$ is 2 or higher, $R_{23}$'s may be the same or different or together form a ring. $R_{21}$ do not form a ring with $R_{23}$ and do not have four or more hydroxyl groups in the molecule. $A_2$ represents an acid radical or, in other words, $A_2$-H is an acid, and $m_2$ represents 0 or a positive integer.

In formula (IV), $R_{41}$ represents a substituent and $n_{41}$ represents 0 or an integer of 1 to 4. When $n_{41}$ is 2 or higher, $R_{41}$'s may be the same or different or together form a ring. $A_{41}$ represents an acid radical or, in other words, $A_{41}$-H is an acid, and $m_{41}$ represents 0 or a positive integer.

In formula (V), $R_{51}$ represents a hydrogen atom or an alkyl, aryl or heterocyclic group, $R_{52}$ represents a substituent. $n_{51}$ represents an integer of 1 to 4. When $n_{51}$ is 2 or higher, $R_{52}$s may be the same or different or together form a ring. $R_{51}$ does not form a ring with $R_{52}$. $A_{51}$ represents an acid radical or, in other words, $A_{51}$ -H is an acid, and $m_{51}$ represents 0 or a positive integer.

DETAILED EXPLANATION OF THE PREFERRED EMBODIMENTS

The detailed description will be made on the compounds of the general formulae (I) to (V).

The term "alkyl groups" herein indicates linear, branched and cyclic alkyl groups which may have a substituent.

In general formula (I), $R_1$ represents an alkyl group, aryl group or heterocyclic group. These substituents may be further substituted by other substituents such as those comprising, for example, halogen, oxygen, nitrogen, sulfur and/or carbon atom (e.g. alkyl, alkenyl, alkynyl, aryl, hydroxyl, nitro and cyano groups). When $R_1$ is an alkyl group, it is preferred that among the carbon atoms in $R_1$, elements other than hydrogen element and carbon element are bonded to the carbon atom directly bonded to the nitrogen atom in the general formula (I). When $R_1$ is a heterocyclic group, the nitrogen atom bonded to $R_1$ in the general formula (1) is preferably bonded to a carbon atom constituting the heterocyclic ring of the heterocyclic group. The alkyl groups are linear, branched or cyclic alkyl groups having 1 to 25 carbon atoms, preferably 1 to 15 carbon atoms, such as methyl, ethyl, propyl, isopropyl, t-butyl, 2-hydroxyethyl, 3-hydroxypropyl, benzyl, 2-methanesulfonamidoethyl, 3-methanesulfonamidopropyl, 2-methanesulfonylethyl, 2-methoxyethyl, cyclopentyl, 2-acetamidoethyl, hydroxymethyl, 2-carboxyethyl, 2-carbamoylethyl, 3-carbamoylpropyl, 2,3-dihydroxypropyl, 3,4-dihydroxybutyl, 2,3,4-trihydroxybutyl, 2,3,4,5-tetrahydroxypentyl, 2,3,4,5,6-pentahydroxyhexyl, methanesulfonamidomethyl, n-hexyl, n-decyl, n-octadecyl, 2-ethylhexyl, 2-hydoxypropyl, 4-hydroxybutyl, 2-carbamoylaminoethyl, 3-carbamoylaminopropyl, 4-carbamoylaminobutyl, 4-carbamoylbutyl, 2-carbamoyl-1-methylethyl, carbamoylaminomethyl, 4-nitrobutyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-[2-(2-2-(2-hydroxyethoxy)ethoxy]ethoxy)ethoxy]ethyl, 2-(2-[2-(2-[2-(2-hydroxyethoxy)ethoxyethoxy) ethoxy]ethoxy)ethyl, 2-[2-(2-[2-(2-[2-(2-hydroxyethoxy)ethoxy]ethoxy)ethoxy] ethoxy)ethyl, 2-(2-[2-(2-[2-(2-[2-(2-hydroxyethoxy) ethoxy]ethoxy]ethoxy)ethoxy] ethoxy)ethyl, 2-(2-methoxyethoxy)ethyl, 2-[2-(2-methoxyethoxy)ethoxy] ethyl, 2-(2-[2-(2-methoxyethoxy)ethoxy]ethoxy)ethyl, 2-[2-(2-[2-(2-methoxyethoxy)ethoxy]ethoxy)ethoxy]ethyl, 2-(2-ethoxyethoxy)ethyl and 2-[2-(2-butoxyethoxy)ethoxy]ethyl groups.

The aryl groups are preferably those having 6 to 24 carbon atoms such as phenyl, naphthyl and p-methoxyphenyl groups. The heterocyclic groups are five-membered or six-membered, saturated or unsaturated heterocyclic groups containing 1 to 5 carbon atoms and at least one of oxygen, nitrogen and sulfur atoms. The number of the hetero atoms or elements constituting the ring may be one or more. The heterocyclic groups include 2-furyl, 2-thienyl, 2-pyrimidinyl, 2-benzotriazolyl, imidazolyl and pyrazolyl groups.

$R_1$ is preferably an alkyl group or an aryl group, particularly the alkyl group.

Preferred examples of $R_1$ include methyl, ethyl, propyl, isopropyl, 2-hydroxyethyl, 3-hydroxypropyl, benzyl, 2-methanesulfonamidoethyl, 2,3-dihydroxypropyl, 3,4-dihydroxybutyl, 2,3,4-trihydroxybutyl, 2,3,4,5-tetrahydroxypentyl, 2,3,4,5,6-pentahydroxyhexyl, n-hexyl, n-octyl, n-decyl, n-octadecyl, 2-ethylhexyl, 2-hydroxypropyl, 4-hydroxybutyl, 2-(2-hydroxyethoxy)ethyl, 2-[2-(2-hydroxyethoxy)ethoxy]ethyl, 2-(2-[2-(2-hydroxyethoxy)ethoxy] ethoxy)ethyl, 2-[2-(2-[2-(2-hydroxyethoxy)ethoxy]ethoxy)ethoxy]ethyl, 2-(2-[2-(2-[2-(2-hydroxyethoxy)ethoxy]ethoxy)ethoxy]ethoxy)ethyl, 2-[2-(2-[2-(2-[2-(2-hydroxyethoxy)ethoxy]ethoxy)ethoxy] ethoxy)ethoxy]ethyl, 2-(2-[2-(2-[2-(2-[2-(2-hydroxyethoxy) ethoxy]ethoxy)ethoxy] ethoxy)ethoxy]ethyl, 2-(2-methoxyethoxy)ethyl, 2-[2-(2-methoxyethoxy)ethoxy] ethyl, 2-[2-(2-butoxyethoxy)ethoxy]ethyl, mercaptoethyl, pyrimidinyl, carboxymethyl, 2-carbamoylaminoethyl, sulfoethyl, 2-bromoethyl, phenyl and p-methoxyphenyl. Particularly preferred examples of $R_1$ include methyl, ethyl, propyl, isopropyl, 2-hydroxyethyl, 3-hydroxypropyl, 2-methanesulfonamidoethyl, 2,3-dihydroxypropyl, 3,4-dihydroxybutyl, 2,3,4-trihydroxybutyl, 2,3,4,5-tetrahydroxypentyl, 2,3,4,5,6-pentahydroxyhexyl, n-hexyl, n-octyl, n-decyl, n-octadecyl, 2-ethylhexyl, 2-(2-hydroxyethoxy)ethyl, 2-[2-(2-hydroxyethoxy)ethoxylethyl, 2-(2-[2-(2-hydroxyethoxy)ethoxy] ethoxy)ethyl, 2-(2-[2-(2-hydroxyethoxy)ethoxy]ethoxy)ethyl, 2-(2-[2-(2-[2-(2-hydroxyethoxy)ethoxy]ethoxy)ethoxy]ethyl, 2-(2-[2-(2-[2-(2-hydroxyethoxy)ethoxy]ethoxy)ethoxy] ethoxy)ethyl, 2-(2-methoxyethoxy)ethyl, 2-[2-(2-methoxyethoxy)ethoxy] ethyl, 2-[2-(2-butoxyethoxy)ethoxy]ethyl, mercaptoethyl, pyrimidinyl, carboxymethyl, 2-carbamoylaminoethyl, sulfoethyl, 2-bromoethyl and phenyl.

More particularly preferred examples of $R_1$ include methyl, isopropyl, 2-hydroxyethyl, 3-hydroxypropyl, 2-methanesulfonamidoethyl, 3,4-dihydroxybutyl, 2,3,4,5,6-pentahydroxyhexyl, n-hexyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-[2-(2-[2-(2-hydroxyethoxy) ethoxyethoxy)ethoxy]ethyl, 2-(2-[2-(2-15 [2-(2-hydroxyethoxy)ethoxy] ethoxy)ethoxy]ethoxy)ethyl, 2-(2-[2-(2-[2-(2-[2-(2-hydroxyethoxy)ethoxy]ethoxy) ethoxy]ethoxy)ethoxy]ethoxy)ethyl, 2-[2-(2-methoxyethoxy)ethoxy]ethyl, 2-[2-(2-butoxyethoxy) ethoxy]ethyl, mercaptoethyl, pyrimidinyl, carboxymethyl, 2-carbamoylaminoethyl, sulfoethyl and 2-bromoethyl. Further particularly preferred examples of $R_1$ include methyl, 2-hydroxyethyl, 3-hydroxypropyl, 3,4-dihydroxybutyl, 2,3, 4,5,6-pentahydroxyhexyl, 2-(2-hydroxyethoxy)ethyl, 2-[2-(2-hydroxyethoxy)ethoxy]ethyl, 2-(2-[2-(2-hydroxyethoxy) ethoxy] ethoxy)ethyl, 2-(2-[2-(2-[2-(2-hydroxyethoxy) ethoxy]ethoxy)ethoxy] ethoxy)ethyl, and mercaptoethyl.

$R_2$ represents a substituent. Examples of the substituents include halogen atoms and groups such as alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups. They may be substituted by an alkyl group, alkenyl group, alkynyl group, aryl group, hydroxyl group, nitro group, cyano group, halogen atom, mercapto group or another substituent comprising oxygen atom, nitrogen atom, sulfur atom and/or carbon atom.

As for the detailed examples of substituents $R_2$, the halogen atoms are, for example, fluorine atom and chlorine atom. The alkyl groups are linear, branched or cyclic alkyl groups having 1 to 25 carbon atoms, preferably 1 to 15 carbon atoms, such as methyl, ethyl, propyl, isopropyl, t-butyl, hydroxymethyl, mercaptomethyl, 2-hydroxyethyl, 2-mercaptoethyl, 3-hydroxypropyl, benzyl, 2-methanesulfonamidoethyl, 3-methanesulfonamidopropyl, 2-methanesulfonylethyl, 2-methoxyethyl, cyclopentyl, 2-acetamidoethyl, hydroxymethyl, 2-carboxyethyl, 2-carbamoylethyl, 3-carbamoylpropyl, 2,3-dihydroxypropyl, 2,3-dimercaptopropyl, 3,4-dihydroxybutyl, methanesulfonamidomethyl, n-hexyl, 2-hydoxypropyl, 4-hydroxybutyl, 2-carbamoylaminoethyl, 3-carbamoylaminopropyl, 4-carbamoylaminobutyl, 4-carbamoylbutyl, 2-carbamoyl-1-methylethyl, carbamoylaminomethyl, 4-nitrobutyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-[2-(2-[2-(2-hydroxyethoxy)ethoxy]ethoxy)ethoxy]ethyl, 2-(2-methoxyethoxy)ethyl, 2-[2-(2-methoxyethoxy) ethoxy] ethyl, 2-(2-[2-(2-methoxyethoxy)ethoxy]ethoxy)ethyl, 2-[2.-(2-[2-(2-methoxyethoxy)ethoxy]ethoxy)ethoxy]ethyl, 2-(2-ethoxyethoxy)ethyl and 2-[2-(2-butoxyethoxy)ethoxy] ethyl groups.

The aryl groups are preferably those having 6 to 24 carbon atoms such as phenyl, naphthyl and p-methoxyphenyl groups. The heterocyclic groups are five-membered or six-membered, saturated or unsaturated heterocyclic groups containing 1 to 5 carbon atoms and at least one of oxygen, nitrogen and sulfur atoms. The number of the hetero atoms and the variety of the elements constituting the ring may be one or more. The heterocyclic groups include 2-furyl, 2-thienyl, 2-pyrimidinyl, 2-benzotriazolyl, imidazolyl and pyrazolyl groups.

The alkoxyl groups are those having 1 to 16 carbon atoms, preferably 1 to 6 carbon atoms, such as methoxyl, ethoxyl, 2-mercaptoethoxyl, 2-methoxyethoxyl and 2-methanesulfonylethoxyl groups. The aryloxy groups are those having 6 to 24 carbon atoms such as phenoxy, p-methoxyphenoxy and m-(3-hydroxypropionamido) phenoxy groups. The acylamino groups are those having 1 to 16 carbon atoms, preferably 1 to 6 carbon atoms, such as acetamido, 2-methoxypropionamido and p-nitrobenzoylamido groups.

The alkylamino groups are those having 1 to 16 carbon atoms, preferably 1 to 6 carbon atoms, such as dimethylamino, diethylamino, bis(2-mercaptoethyl)amino and 2-hydroxyethylamino groups. The anilino groups are those having 6 to 24 carbon atoms such as anilino, m-nitroanilino and N-methylanilino groups. The ureido groups are those having 1 to 16 carbon atoms, preferably 1 to 6 carbon atoms, such as ureido, methylureido, N,N-diethylureido and 2-methanesulfonamidoethylureido groups.

The sulfamoylamino groups are those having 0 to 16 carbon atoms, preferably 0 to 6 carbon atoms, such as dimethylsulfamoylamino, methylsulfamoylamino and 2-methoxyethylsulfamoylamino groups. The alkylthio groups are those having 1 to 16 carbon atoms, preferably 1 to 6 carbon atoms, such as methylthio, ethylthio and 2-phenoxyethylthio groups. The arylthio groups are those having 6 to 24 carbon atoms such as phenylthio, 2-carboxyphenylthio and 4-cyanophenylthio groups. The alkoxycarbonylamino groups are those having 2 to 16 carbon atoms, preferably 2 to 6 carbon atoms, such as methoxycarbonylamino, ethoxycarbonylamino and 3-methanesulfonylpropoxycarbonylamino groups.

The sulfonamido groups are those having 1 to 16 carbon atoms, preferably 1 to 6 carbon atoms, such as methanesulfonamido, p-toluenesulfonamido and 2-methoxyethanesulfonamido groups. The carbamoyl groups are those having 1 to 16 carbon atoms, preferably 1 to 6 carbon atoms, such as carbamoyl, N,N-dimethylcarbamoyl and N-ethylcarbamoyl groups. The sulfamoyl groups are those having 0 to 16 carbon atoms, preferably 0 to 6 carbon atoms, such as sulfamoyl, dimethylsulfamoyl and ethylsulfamoyl groups.

The sulfonyl groups are aliphatic or aromatic sulfonyl groups having 1 to 16 carbon atoms, preferably 1 to 6 carbon atoms, such as methanesulfonyl, ethanesulfonyl and 2-chloroethanesulfonyl groups. The alkoxycarbonyl groups are those having 1 to 16 carbon atoms, preferably 1 to 6 carbon atoms, such as methoxycarbonyl, ethoxycarbonyl and t-butoxycarbonyl groups. The heterocyclic oxy groups are five-membered or six-membered, saturated or unsaturated heterocyclic oxy groups containing 1 to 5 carbon atoms and at least one of oxygen, nitrogen and sulfur atoms. The number of the hetero atom(s) constituting the ring may be one or more, and when the ring contains two or more elements of the hetero atoms, the kind of them may be the same or different. Examples of the heterocyclic oxy groups include 1-phenyltetrazolyl-5-oxy, 2-tetrahydropyranyloxy and 2-pyridyloxy groups.

The azo groups are those having 1 to 16 carbon atoms, preferably 1 to 6 carbon atoms, such as phenylazo, 2-hydroxy-4-propanoylphenylazo and 4-sulfophenylazo groups. The acyloxy groups are those having 1 to 16 carbon atoms, preferably 1 to 6 carbon atoms, such as acetoxy, benzoyloxy and 4-hydroxybutanoyloxy groups. The carbamoyloxy groups are those having 1 to 16 carbon atoms, preferably 1 to 6 carbon atoms, such as N,N-dimethylcarbamoyloxy, N-methylcarbamoyloxy and N-phenylcarbamoyloxy groups.

The silyl groups are those having 3 to 16 carbon atoms, preferably 3 to 6 carbon atoms, such as trimethylsilyl, isopropyldiethylsilyl and t-butyldimethylsilyl groups. The silyloxy groups are those having 3 to 16 carbon atoms, preferably 3 to 6 carbon atoms, such as trimethylsilyloxy, triethylsilyloxy and diisopropylethylsilyloxy groups. The aryloxycarbonylamino groups are those having 7 to 24 carbon atoms such as phenoxycarbonylamino, 4-cyanophenoxycarbonylamino and 2, 6-dimethoxyphenoxycarbonylamino groups.

The imido groups are those having 4 to 16 carbon atoms such as N-succinimido and N-phthalimido groups. The heterocyclic thio groups are five-membered or six-membered, saturated or unsaturated heterocyclic thio groups containing 1 to 5 carbon atoms and at least one of oxygen, nitrogen and sulfur atoms. The number of the hetero atom(s) constituting the ring may be one or more, and when the ring contains two or more elements of the hetero atoms, the kind of them may be the same or different. Examples of the heterocyclic thio groups include 2-benzothiazolylthio and 2-pyridylthio groups.

The sulfinyl groups are those having 1 to 16 carbon atoms, preferably 1 to 6 carbon atoms, such as methanesulfinyl, benzenesulfinyl and ethanesulfinyl groups. The phosphonyl groups are those having 2 to 16 carbon atoms, preferably 2 to 6 carbon atoms, such as methoxyphosphonyl, ethoxyphosphonyl and phenoxyphosphonyl groups. The aryloxycarbonyl groups are those having 7 to 24 carbon atoms such as phenoxycarbonyl, 2-methylphenoxycarbonyl and 4-acetamidophenoxycarbonyl groups. The acyl groups are those having 1 to 16 carbon atoms, preferably 1 to 6 carbon atoms, such as acetyl, benzoyl and 4-chlorobenzoyl groups.

$R_2$ is preferably a halogen atom, or an alkyl, heterocyclic, nitro, hydroxyl, carboxyl, sulfo, alkoxyl, acyloxy, amino, alkylamino, ureido, sulfamoylamino, alkylthio, alkoxycarbonylamino, sulfonamido, carbamoyl, sulfamoyl, sulfonyl, alkoxycarbonyl, heterocyclic oxy, azo, acyloxy, carbamoyloxy, imido, heterocyclic thio, sulfinyl, phosphonyl, acyl or mercapto group. $R_2$ is particularly preferably a halogen atom, or an alkyl, heterocyclic, hydroxyl, alkoxyl, alkylamino, ureido, sulfamoylamino, alkylthio, alkoxycarbonylamino, sulfonamido, heterocyclic oxy, heterocyclic thio or mercapto group. Among them, $R_2$ is particularly preferably an alkyl, heterocyclic, alkoxyl, alkylamino, ureido, alkylthio or mercapto group.

Preferred examples of $R_2$ include methyl, i-propyl, 2-mercaptoethyl, 2-thienyl, pyrazolyl, methoxy, isopropoxy, dimethylamino, ureido, methylthio, chlorine, 2,3-dihydroxypropyl and mercapto groups, or two $R_2$'s may together form a furan ring.

More preferred examples of $R_2$ include methyl, i-propyl, methoxy, chlorine, and 2,3-dihydroxypropyl, or two $R_2$'s may together form a furan ring. Further preferred examples of $R_2$ include methyl, i-propyl and methoxy.

Z represents ethylene group or trimethylene group having 2 to 30 carbon atoms, preferably 2 to 15 carbon atoms and more preferably 2 to 6 carbon atoms. The substituents of ethylene group or trimethylene group as Z are halogen atoms and substituents composed of nitrogen, oxygen, sulfur and/or carbon atoms (such as alkyl, alkenyl, alkynyl, aryl, hydroxyl, nitro and cyano groups). These substituents may be further substituted by other substituents. The substituents are those listed above with reference to $R_2$. Preferred substituents include halogen atoms, and hydroxyl, alkyl, alkoxyl, carboxyl, acylamino, alkylamido, ureido, sulfamoylamino, alkoxycarbonylamino, sulfonylamino, carbamoyl, sulfamoyl, sulfonyl, alkoxycarbonyl, acyloxy, carbamoyloxy, acyl and mercapto groups. Particularly preferred substituents are hydroxyl, alkyl, carboxyl, acylamino, ureido, alkoxycarbonylamino, sulfonylamino, carbamoyl, acyloxy, carbamoyloxy and mercapto groups. Still preferred substituents are hydroxyl, alkyl, carboxyl and mercapto groups. Examples of Z include ethylene, 1-methylethylene (the carbon bonded to the nitrogen atom is in the 1-position), 2-methylethylene, 1,2-dimethylethylene, 1,1,2-trimethylethylene, 1,2,2-trimethylethylene, 1,1,2,2-tetramethylethylene, 2-hydroxymethylethylene, 2-hydroxyethylene, 1-methyl-2-hydroxyethylene, 1,1,2-trimethyl-2-carboxyethylene, 1,1,2,2-tetraethylethylene, trimethylene, 1,1-dimethyltrimethylene, 2,2-dimethyltrimethylene, 3,3-dimethyltrimethylene, 1,1,3-trimethyltrimethylene, 1,1,3-trimethyl-2-decyltrimethylene, 1,1,3-trimethyl-2-methyltrimethylene, 1,1-diethyltrimethylene, 2,2-diethyltrimethylene, 3,3-diethyltrimethylene, 1,1,2,2,3,3-hexaethyltrimethylene 1,3-trimethyl-3-carboxytrimethylene, 1,1,3-trimethyl-2-hydroxytrimethylene 1,-dimethyl-2-hydroxy-3-methylidenetrimethylene, 1,1,3-trimethyl-2,3-dihydroxytrimethylene, 1,1,1,3-trimethyl-2-aminotrimethylene 1,1,-diyroxymethyl-32-dimethylaminotrimethylene, 1,3-trimethyl-2-bromotrimethylene, 1,1,3-trimethyl-2-(N-pyrazolyltrimethylene, 1,1-dihydroxymethyl-3-methyltrimethylene, 1,1-dimethyl-3-hydroxymethyltrimethylene, 1,1-dimethyl-3-formyltrimethylene, 1,1-dimethyl-3-carboxytrimethylene, 1,1-dimethyl-3-carbamoyltrimethylene 1,1-dimethyl-3-dimethylcarbamoyl trimethylene, 1,1-dimethyl-3-hydroxymethyl-2,3-dihydroxytrimethylene and 1,1-dimethyl-3-hydroxymethyl-2-hydroxytrimethylene. Among them, particularly preferred examples include ethylene, 1-methylethylene, 2-methylethylene, 1,2-dimethylethylene, 1,2,2-trimethylethylene, 1,1,2,2-tetramethylethylene, 2-hydroxyethylene 1-methyl-2-hydroxyethylenetrimethylene, 1,1-dimethyltrimethylene, 2,2-dimethyltrimethylene, 3,3-dimethyltrimethylene, 1,1,3-trimethyltrimethylene, 1,1,3-triethyl-2-methyltrimethylene, 1,1,3-trimethyl-2-hydroxytrimethylene, 1,1,3-trimethyl-2,3-dihydroxytrimethylene, 1,1-dimethyl-3-hydroxymethyl trimethylene and 1,1-dimethyl-3-hydroxymethyl-2-hydroxytrimethylene. More preferred examples include ethylene, 1-methylethylene, 2-methylethylene, 1,2-dimethylethylenetrimethylene, 1,1-dimethyltrimethylene, 2,2-dimethyltrimethylene, 3,3-dimethyltrimethylene, 1,1,3-trimethyltrimethylene, 1,1,3-trimethyl-2-hydroxytrimethylene and 1,1-dimethyl-3-hydroxymethyltrimethylene.

A represents an acid radical. Namely, A-H represents an acid such as hydrochloric acid, sulfuric acid, phosphoric acid, p-toluenesulfonic acid, methanesulfonic acid, naphthalene-1,5-disulfonic acid, ascorbic acid or oxalic acid. A-H is preferably hydrochloric acid, sulfuric acid, p-toluenesulfonic acid or naphthalene-1,5-disulfonic acid. The most preferred A-H is sulfuric acid or naphthalene-1,5-disulfonic acid. m represents 0 or a positive integer. When m is 2 or above, two or more (A-H)'s may be the same or different.

In a preferred combination of $R_1$, $R_2$, Z and n, $R_1$ is an alkyl group, $R_2$ is an alkyl or alkoxyl group, Z is an ethylene or trimethylene group unsubstituted or substituted with a hydroxyl, alkyl or carboxyl group, which has 2 to 6 carbon atoms in total. n is 0 or 1.

Since $R_{11}$ in the general formula (II) is the same as $R_2$ in the general formula (I), $R_{11}$ is the same as $R_2$.

$R_{11}$ is preferably a halogen atom, or an alkyl, heterocyclic, nitro, hydroxyl, carboxyl, sulfo, alkoxyl, acyloxy, amino, alkylamino, ureido, sulfamoylamino, alkylthio, alkoxycarbonylamino, sulfonamido, carbamoyl, sulfamoyl, sulfonyl, alkoxycarbonyl, heterocyclic oxy, azo, acyloxy, carbamoyloxy, imido, heterocyclic thio, sulfinyl, phosphonyl, acyl or mercapto group. $R_{11}$ is particularly preferably a halogen atom, or an alkyl, heterocyclic, hydroxyl, alkoxyl, alkylamino, ureido, sulfamoylamino, alkylthio, alkoxycarbonylamino, sulfonamido, heterocyclic oxy, heterocyclic thio or mercapto group. Among them, $R_{11}$ is particularly preferably an alkyl, heterocyclic, alkoxyl, alkylamino, ureido, alkylthio or mercapto group.

Preferred examples of $R_{11}$ include methyl, i-propyl, 2-mercaptoethyl, 2-thienyl, pyrazolyl, methoxy, isopropoxy, acetylamino, amino, dimethylamino, sulfamoylamino, carboxy, sulfo, phenyloxy, acetyl, dichlorophenylamino, carbamoylamino, sulfamoylamino, ureido, methylthio and mercapto groups, or two $R_{11}$'s may together form a furan ring.

More preferred examples of $R_{11}$ include methyl, isopropoxy, acetylamino, methoxy, i-propyl, amino, dimethylamino, sulfamoylamino, carboxy, sulfo, phenyloxy, acetyl, dichlorophenylamino, carbamoylamino, sulfamoylamino and methylthio, or two $R_{11}$'s may together form a furan ring. Further preferred examples of $R_{11}$ include methyl, isopropoxy, acetylamino, methoxy, i-propyl, amino, dimethylamino and sulfamoylamino.

Y represents tetramethylene, pentamethylene or hexamethylene group having 4 to 20 carbon atoms, preferably 4 to 10 carbon atoms and more preferably 4 to 8 carbon atoms, which is substituted by a substituent containing at least one of carbon, nitrogen, oxygen and sulfur atoms. Examples of the substituents include an alkyl, aryl, heterocyclic, cyano, nitro, hydroxyl, carboxyl, sulfo, alkoxyl, aryl oxy, acyloxy, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyloxy, aryloxycarbonylamino, imido, heterocyclic thio, sulfinyl, phosphonyl, aryloxycarbonyl, acyl and mercapto groups. They may be further substituted by an alkyl, alkenyl, alkynyl, aryl, hydroxyl, nitro, cyano or mercapto group or a halogen as well as another substituent comprising oxygen, nitrogen, sulfur and/or carbon atom. Examples of these substituents are the same as those described above with reference to $R_{11}$.

Preferred substituents are hydroxyl, alkyl, alkoxyl, carboxyl, acylamino, alkylamino, ureido, sulfamoylamino, alkoxycarbonylamino, sulfonylamino, carbamoyl, sulfamoyl, sulfonyl, alkoxycarbonyl, acyloxy, carbamoyloxy, acyl and mercapto groups. More preferred substituents are hydroxyl, alkyl, alkoxyl, carboxyl, acylamino, alkylamino, ureido, alkoxycarbonylamino, sulfonylamino, carbamoyl, acyloxy, carbamoyloxy and mercapto groups. Particulrly preferred substituents are hydroxyl, alkyl, carboxyl and mercapto groups.

Preferred Y are tetramethylene and pentamethylene groups. Tetrmethylene group is the most preferred.

In a preferred combination of the substituents $R_{11}$, Y and Y with $n_1$, $R_{11}$ is an alkyl or alkoxyl group, Y is tetramethylene or pentamethylene group, the substituent of Y is a hydroxyl, alkyl, carboxyl or mercapto group, and n, is 0 or 1.

$A_1$ represents an acid radical. Namely, $A_1$-H represents an acid. Examples of $A_1$-H are those described above with reference to A-H in formula (1). The most Preferred $A_1$-H is sulfuric acid or naphthalene-1,5-disulfonic acid. $m_1$ represents 0 or a positive integer. When $m_1$ is 2 or above, two or more ($A_1$-H)'s may be the same or different.

Since $R_{21}$ in the general formula (III) is the same as $R_1$ in the general formula (I), $R_{21}$ is the same as $R_1$.

$R_{21}$ is preferably an alkyl or aryl group. It is most preferably an alkyl group.

Preferred examples of $R_{21}$ include methyl, ethyl, 2-(2-hydroxyethoxy)ethyl, 2-[2-(2-hydroxyethoxy)ethoxy]ethyl, 2-(2-[2-(2-hydroxyethoxy)ethoxy] ethoxy)ethyl, 2-(2-[2-(2-[2-(2-(2-hydroxyethoxy)ethoxy]ethoxy)ethoxy]ethoxy)ethyl, and 2-(2-methoxyethoxy)ethyl, hydroxybutyl, phenyl, benzyl, n-propyl, 2-(2-[2-(2-[2-(2-methoxyethoxy)ethoxy]ethoxy)ethoxy]ethoxy)ethyl, and 2-(2-phenoxyethoxy)ethyl. More preferred examples of $R_{21}$ include methyl, ethyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-(2-[2-(2-[2-(2-hydroxyethoxy)ethoxy]ethoxy]ethoxy)ethoxy]ethoxy)ethyl, and 2-(2-methoxyethoxy)ethyl.

$R_{22}$ represents a hydrogen atom or an alkyl, aryl or heterocyclic group. The alkyl, aryl and heterocyclic groups are the same as those listed above with reference to $R_{21}$. Among them, the hydrogen atom, alkyl group such as methyl group and phenyl group are preferred. Hydrogen atom and methyl group are the most preferred. $R_{23}$ represents a substituent. The substituents are those described above with reference to $R_{11}$.

Preferred examples of $R_{23}$ include trimethylsiloxy, phenoxycarbonyl, isopropoxy, i-propyl, methyl, mercaptoethyl, trimethylsilyl, succinimidyl, pyridylthio, sukfino, phenoxycarbonyl and methoxy. More preferred examples of $R_{23}$ include trimethylsiloxy, phenoxycarbonyl, isopropoxy, i-propyl, methyl and mercaptoethyl.

$n_{21}$ represents an integer of 2 to 8, preferably 2 to 6 and more preferably 2 to 4. $R_{21}$ has particularly preferably a structure of the general formula: $-(CH_2CH_2O)_{n23}R_{24}$.

$R_{24}$ in this formula represents a hydrogen atom or an alkyl, aryl or heterocyclic group. The alkyl, aryl and heterocyclic groups are the same as those described above with reference to $R_{22}$. Among them, the hydrogen atom or alkyl group is preferred. The hydrogen atom is most preferred. $n_{23}$ represents an integer of 2 to 8. The most preferably, $R_{21}$ is a group of the general formula: $-(CH_2CH_2O) \ n_{23}R_{24}$ wherein $n_{23}$ is the same as $n_{21}$, and $R_{24}$ is the same as $R_{22}$.

Preferred compounds of the general formula (III) are those wherein $R_{21}$ is represented by $-(CH_2CH_2O)_{n23}R_{24}$ wherein $R_{24}$ is the same as $R_{22}$ and represents a hydrogen atom or alkyl group, $n_{23}$ is the same as $n_{21}$ and represents an integer of 2 to 4, $R_{23}$ represents an alkyl or alkoxyl group, and $n_{22}$ is 0 or 1.

$A_2$ represents an acid radical. Namely, $A_2$-H represents an acid. Examples of $A_2$-H are those described above with reference to A-H in formula (I). The most preferred $A_2$-H is sulfuric acid or naphthalene-1,5-disulfonic acid. $m_2$ represents 0 or a positive integer. When $m_2$ is 2 or above, two or more ($A_2$-H)'s may be the same or different.

Since $R_{41}$ in the general formula (IV) is a substituent and is the same as $R_2$ in the general formula (I), $R_{41}$ is the same as $R_2$.

$R_{41}$ is preferably a halogen atom or an alkyl, heterocyclic, nitro, hydroxyl, carboxyl, sulfo, alkoxyl, acyloxyl, amino, alkylamino, ureido, ulfamoylamino, alkylthio, alkoxycarbonylamino, sulfonamido, carbamoyl, sulfamoyl, sulfonyl, alkoxycarbonyl, heterocyclic oxy, azo, acyloxy, carbamoyloxy, imido, heterocyclic thio, sulfinyl, phosphonyl, acyl or mercapto group. $R_{41}$ is particularly preferably a halogen atom, or an alkyl, heterocyclic, hydroxyl, alkoxyl, alkylamino, ureido, sulfamoylamino, alkylthio, alkoxycarbonylamino, sulfonamido, heterocyclic oxy, heterocyclic thio or mercapto group. Among them, $R_{41}$ is particularly preferably an alkyl, heterocyclic, alkoxyl, alkylamino, ureido, alkylthio or mercapto group.

Preferred examples of $R_{41}$ include methyl, ethyl, i-propyl, ethoxy, 2-mercaptoethyl, 2-thienyl, pyrazolyl, methoxy, isopropoxy, n-hexanoxy, dimethylpyrazolyl, dimethylamino, carbamoylamino, n-methyl-n-(dimethylaminocarbonyl) ureido, methylthio, ethylthio, mercapto, n-butylthio, n-octylthio, mercaptoethylthio and hydroxyethylthio groups.

More preferred examples of $R_{41}$ include methyl, ethyl, i-propyl, ethoxy, isopropoxy, mercaptoethyl, methoxy, n-hexanoxy, dimethylpyrazolyl, dimethylamino, carbamoylamino, n-methyl-n-(dimethylaminocarbonyl) methylthio, ethylthio, mercapto, n-butylthio, n-octylthio, mercaptoethylthio and hydroxyethylthio. Further preferred examples of $R_{41}$ include methyl, ethyl, i-propyl, ethoxy, isopropoxy and mercaptoethyl.

$n_{41}$ represents an integer of 1 to 4, preferably 0 or 1.

$A_{41}$ represents an acid radical. Namely, $A_{41}$-H represents an acid. Examples of $A_{41}$-H are those described above with reference to A-H in formula (I). The most preferred $A_{41}$-H is sulfuric acid or naphthalene-1,5-disulfonic acid. $m_{41}$ represents 0 or a positive integer. When $m_{41}$ is 2 or above, two or more $A_{41}$-H's may be the same or different.

Since $R_{51}$ in the general formula (V) represents a hydrogen atom or an alkyl, aryl or heterocyclic group, and is the same as $R_1$ (but excepting the hydrogen atom) in the general formula (I), the same description given above for $R_1$ is applied to $R_{51}$.

$R_{51}$ is preferably a hydrogen atom or an alkyl or aryl group. It is particularly preferably hydrogen or an alkyl group.

For preferred examples of $R_{51}$ other than hydrogen atom, the same description given above for $R_1$ is applied to $R_{51}$.

Preferred examples of $R_{51}$ include a hydrogen atom, methyl, n-hexyl, 2-(2-hydroxyethoxy)ethyl and phenyl. More preferred examples of $R_{51}$ include a hydrogen atom, methyl and n-hexyl.

$R_{52}$ is a substituent. The substituents $R_{52}$ are the same as the substituents $R_{41}$. The preferred substituents $R_{52}$ include halogen atoms, and alkyl, heterocyclic, nitro, hydroxyl, carboxyl, sulfo, alkoxyl, acyloxyl, amino, alkylamino, ureido, ulfamoylamino, alkylthio, alkoxycarbonylamino, sulfonamido, carbamoyl, sulfamoyl, sulfonyl, alkoxycarbonyl, heterocyclic oxy, azo, acyloxy, carbamoyloxy, imido, heterocyclic thio, sulfinyl, phophonyl, acyl or mercapto group. $R_{52}$ is particularly preferably a halogen atom, or an alkyl, heterocyclic, hydroxyl, alkoxyl, alkylamino, ureido, sulfamoylamino, alkylthio, alkoxycarbonylamino, sulfonamido, heterocyclic oxy, heterocyclic thio or mercapto group. Among them, $R_{52}$ is particularly preferably an alkyl, heterocyclic, alkoxyl, alkylamino, ureido, alkylthio or mercapto group.

Preferred examples of $R_{52}$ include methyl, i-propyl, 2-mercaptoethyl, 2-thienyl, pyrazolyl, methoxy, isopropoxy, dimethylamino, ureido, methylthio and mercapto groups.

More preferred examples of $R_{52}$ include methyl, ethyl, i-propyl, methoxy, ethoxy, isopropoxy, hydroxyethoxy, 1-methylheptyloxy, mercaptoethyl, methylthio, dimethylamino, mercapto and mercaptomethoxy, or two $R_{52}$'s may together form a methylpyrrole ring. Further preferred examples of $R_{52}$ include methyl, i-propyl, methoxy, methylthio, 1-methylheptyloxy, isopropoxy and hydroxyethoxy.

$n_{51}$ represents an integer of 1 to 4, preferably 0 or 1.

$A_{51}$ represents an acid radical. Namely, $A_{51}$-H represents an acid. Examples of $A_{51}$-H are those described above with reference to A-H in formula (I). The most preferred $A_{51}$-H is sulfuric acid or naphthalene-1,5-disulfonic acid. $m_{51}$ represents 0 or a positive integer. When $m_{51}$ is 2 or above, two or more $A_{51}$-H's may be the same or different.

Examples of the compounds represented by the general formulae (I) to (V) of the present invention are given below, which by no means limit the invention. The stereostructures are not specified in the following formulae, and any possible stereostructure is possible. Mixtures of stereoisomers are also within the present invention.

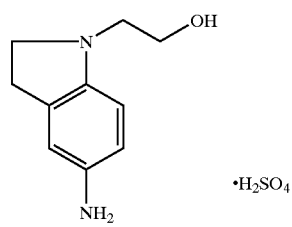

A-1)

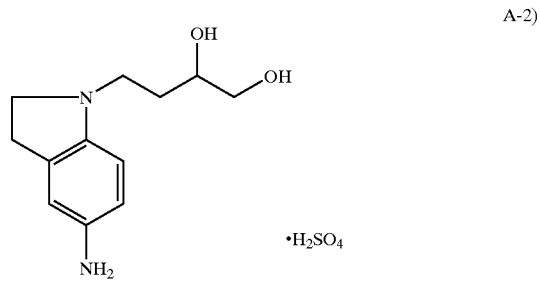

A-2)

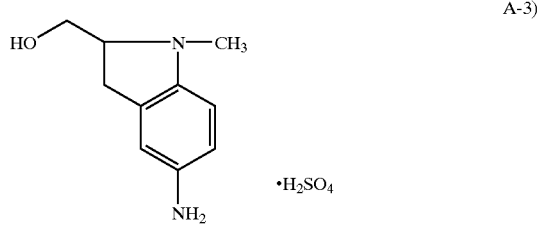

A-3)

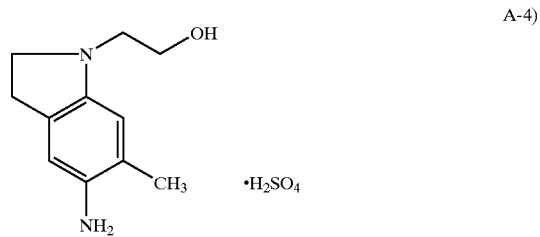

A-4)

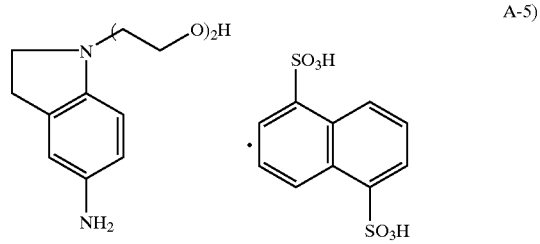

A-5)

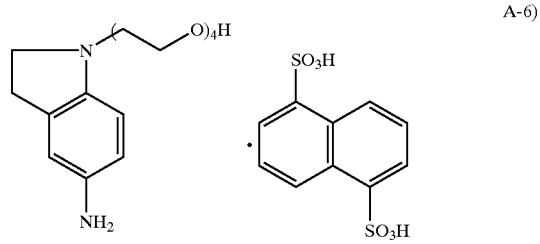

A-6)

A-7)
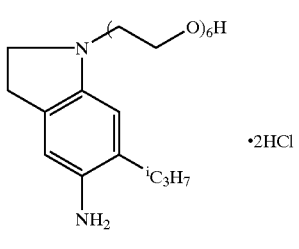
A-8)
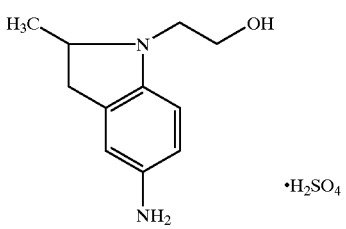
A-9)
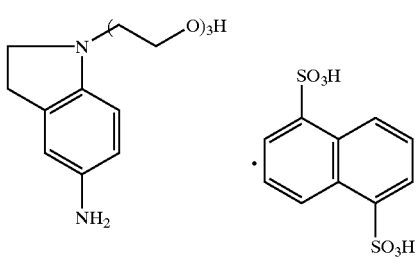
A-10)
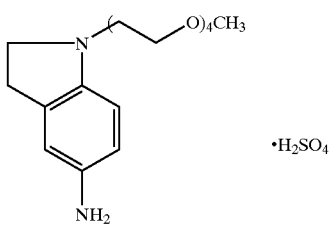
A-11)
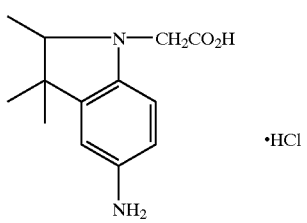
A-12)
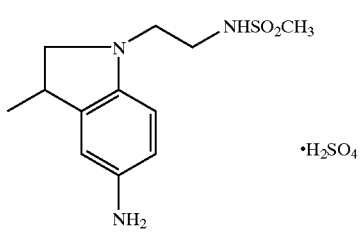
A-13)
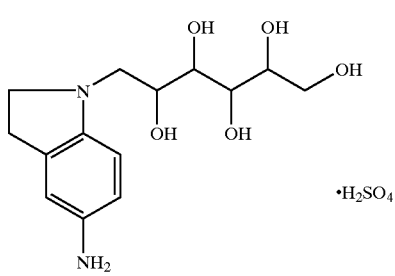
A-14)
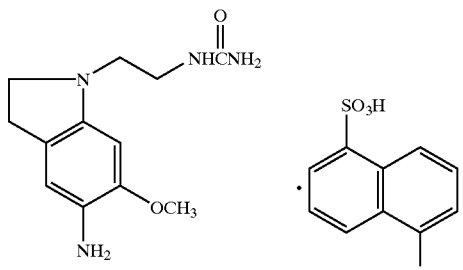
A-15)
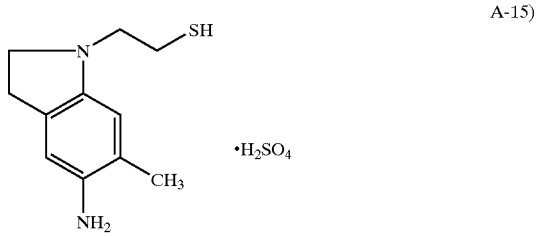
A-16)
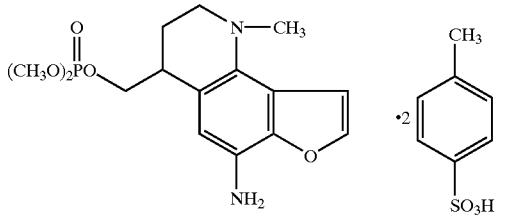
A-17)
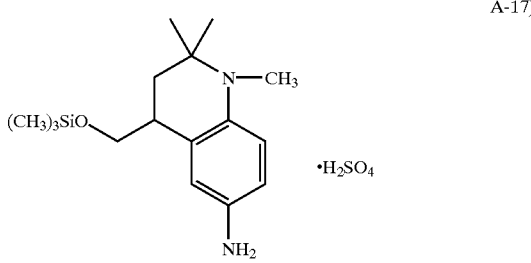
A-18)
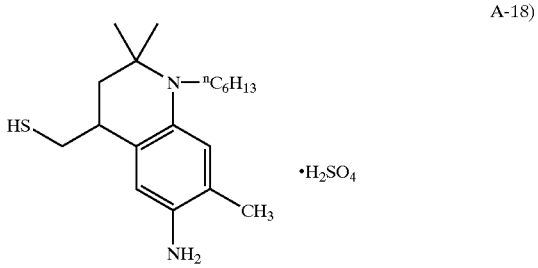

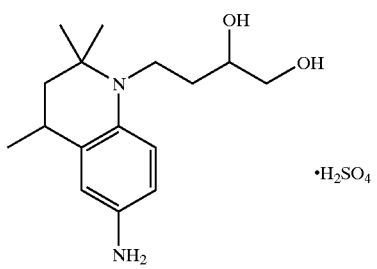
A-19)
·H₂SO₄
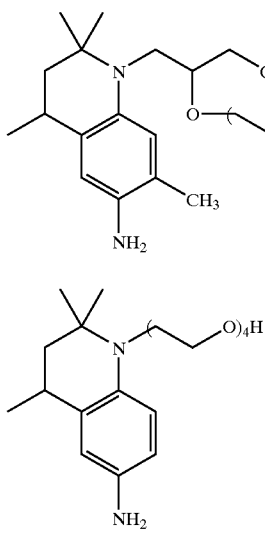
A-20)
·H₂SO₄
A-21)
·H₂SO₄
A-22)
·H₂SO₄
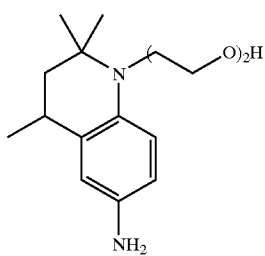
A-23)
·2HCl
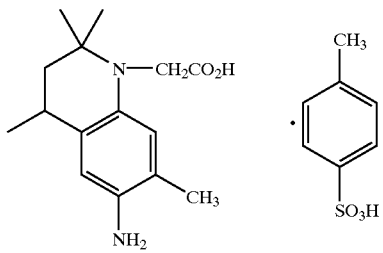
A-24)
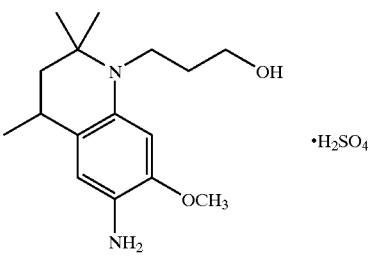
A-25)
·H₂SO₄
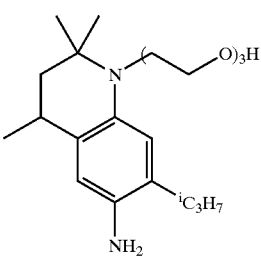
A-26)
·H₂SO₄
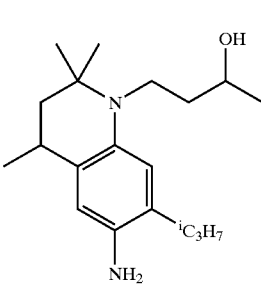
A-27)
·H₂SO₄
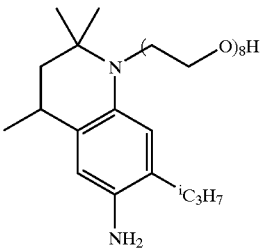
A-28)
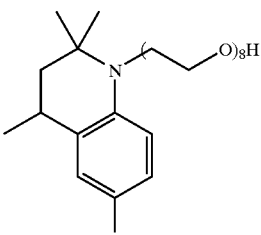
A-29)
·H₂SO₄
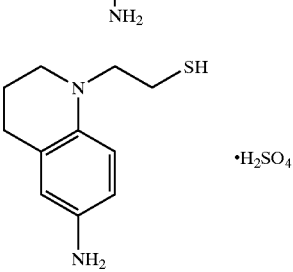
A-30)
·H₂SO₄

-continued

A-31) A-37) A-38) A-32) A-33) A-39) A-34) A-40) A-35) A-41) A-36) A-42)

-continued

A-43) [structure] ·H₂SO₄

A-44) [structure] ·H₂SO₄

A-45) [structure] ·H₂SO₄

A-46) [structure]

A-47) [structure] ·H₂SO₄

A-48) [structure] ·H₂SO₄

A-49) [structure] ·H₂SO₄

A-50) [structure] ·H₂SO₄

A-51) [structure] ·3 [p-toluenesulfonic acid]

A-52) [structure]

A-53) 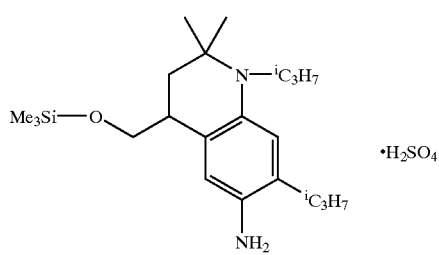 ·H₂SO₄
A-54) 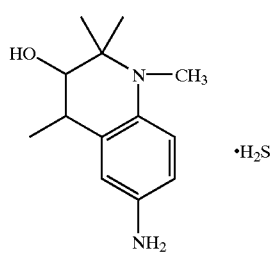 ·H₂SO₄
A-55) 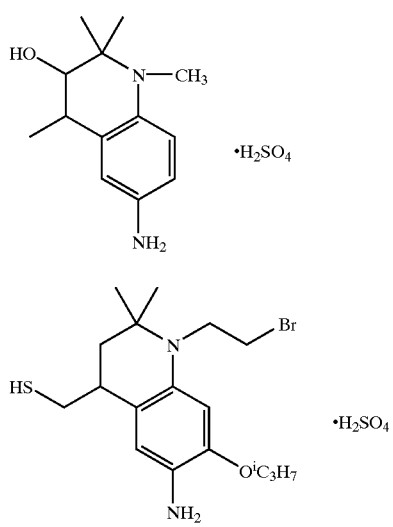 ·H₂SO₄
A₂-1) 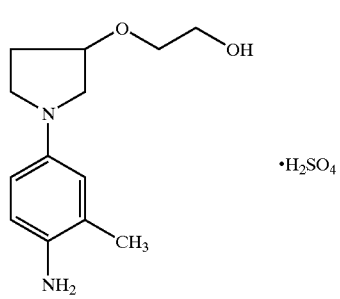 ·H₂SO₄
A₂-2) 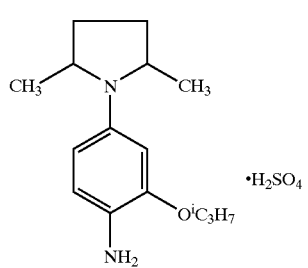 ·H₂SO₄
A₂-3) 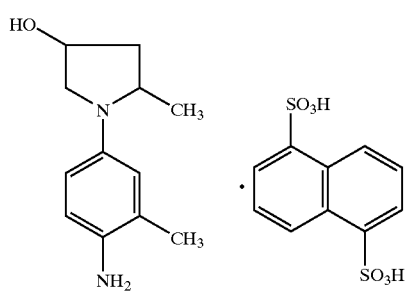
A₂-4) 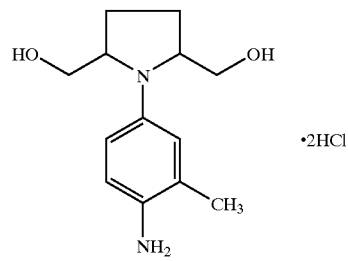 ·2HCl
A₂-5) 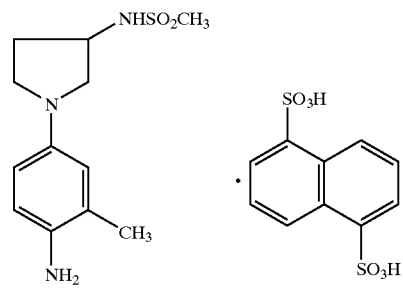
A₂-6) 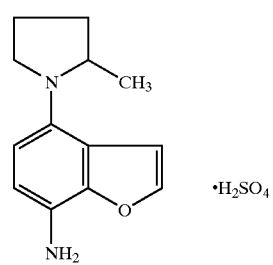 ·H₂SO₄
A₂-7) 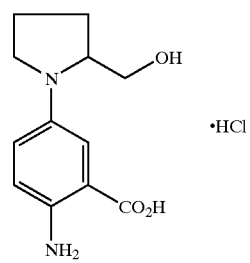 ·HCl
A₂-8) 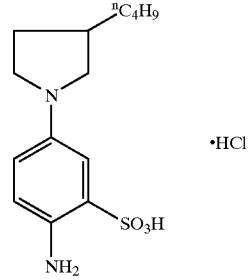 ·HCl

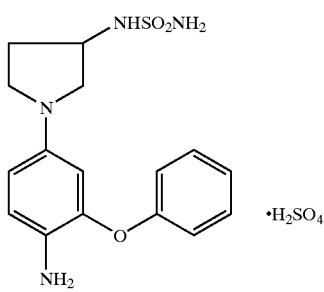
·H₂SO₄
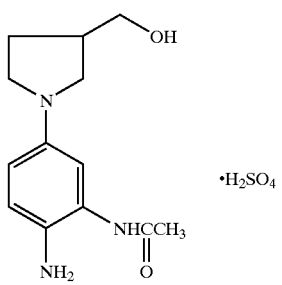
·H₂SO₄
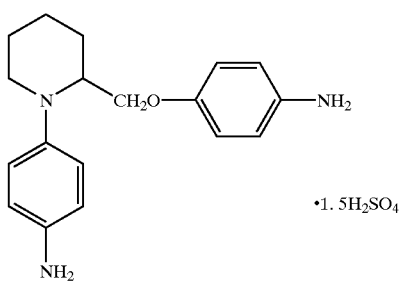
·1.5H₂SO₄
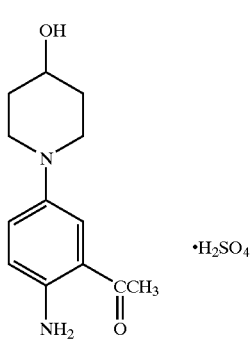
·H₂SO₄
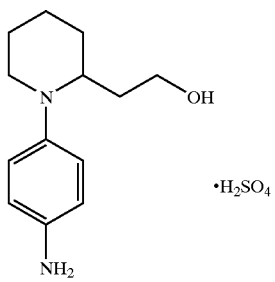
·H₂SO₄
A₂-9)
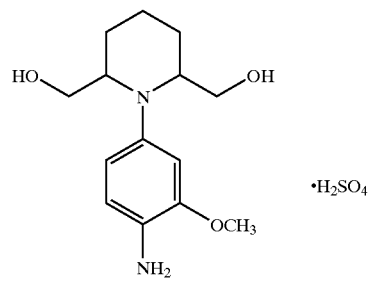
·H₂SO₄
A₂-10)
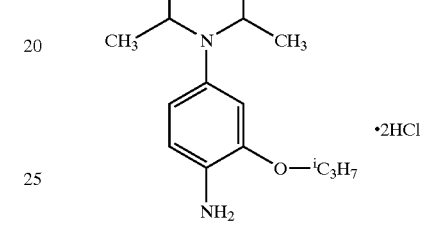
·2HCl
A₂-11)
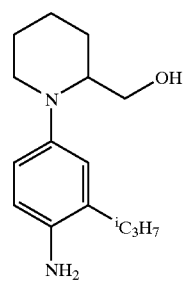
·H₂SO₄
A₂-12)
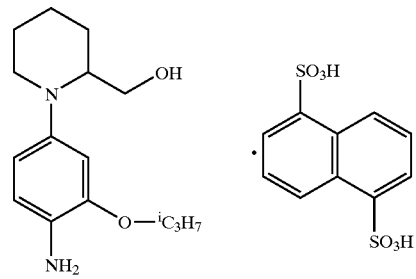
A₂-13)
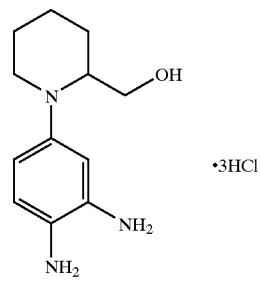
·3HCl -continued
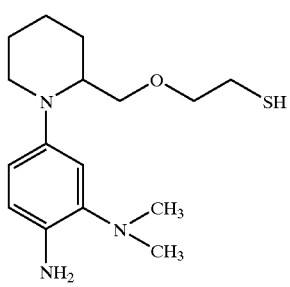
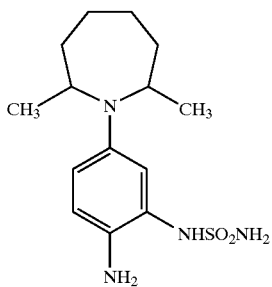
·1. 5H₂SO₄
A₂-19)
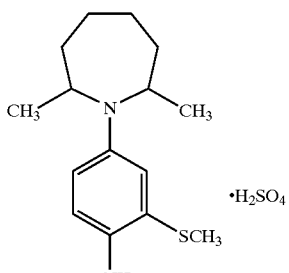
·H₂SO₄
A₂-24)
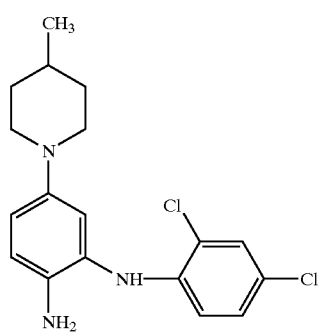
·1.5
A₂-20)
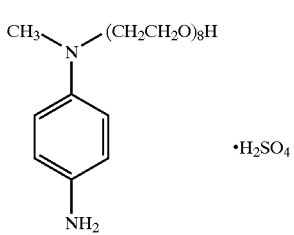
·H₂SO₄
A₂-25)
A₂-26)
CH₃\N−(CH₂CH₂O)₈H
<image of aniline with N(CH3)(CH2CH2O)8H>
·H₂SO₄
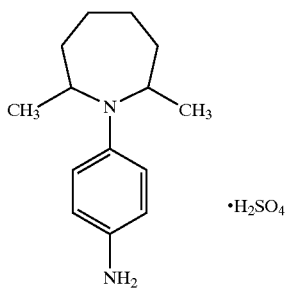
·H₂SO₄
A₂-21)
A₂-27)
HO−(CH₂)₄−N−(CH₂CH₂O)₃H on aryl with iC₃H₇ and NH₂
·
naphthalene-1,5-disulfonic acid (SO₃H / SO₃H)
A₂-22)
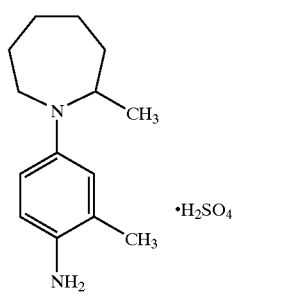
·H₂SO₄
Ph−N(CH₂CH₂O)₂H aryl NH₂
·H₂SO₄
A₂-28)
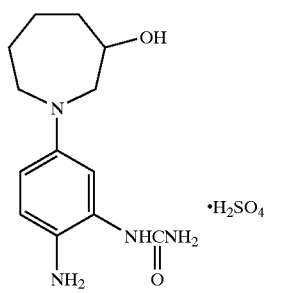
·H₂SO₄
A₂-23)
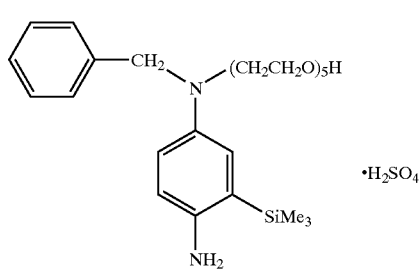
·H₂SO₄
A₂-29)

A2-30) 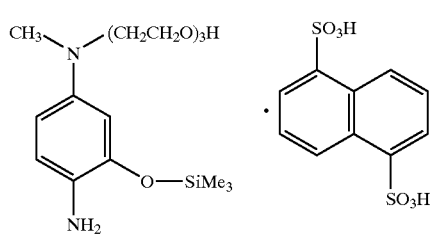
A2-31) 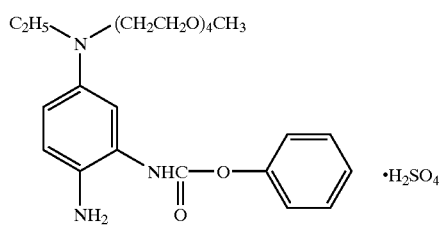
A2-32) 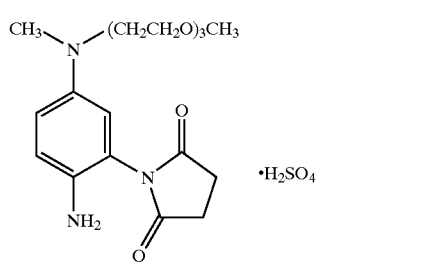
A2-33) 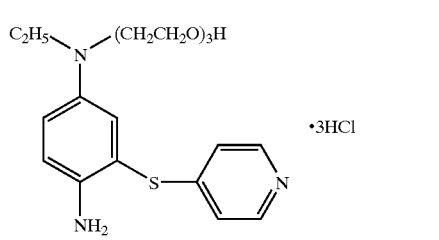
A2-34) 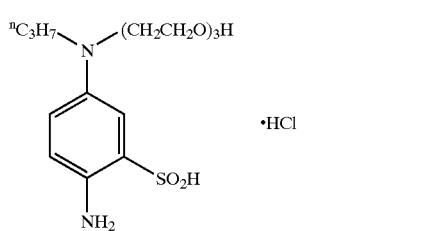
A2-35) 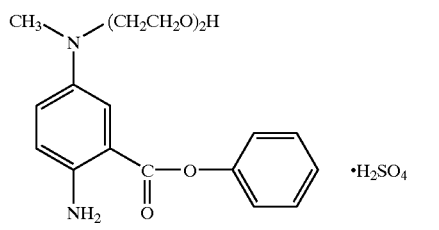
A2-36) 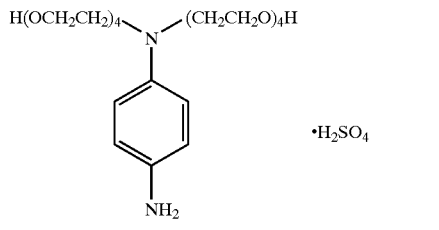
A2-37) 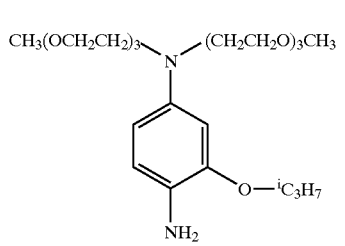
A2-38) 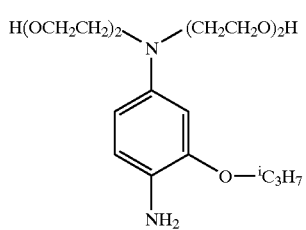
A2-39) 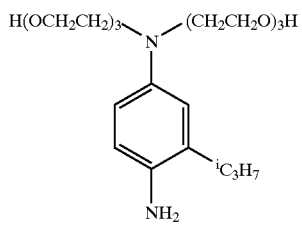
A2-40) 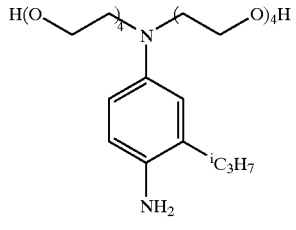
A2-41) 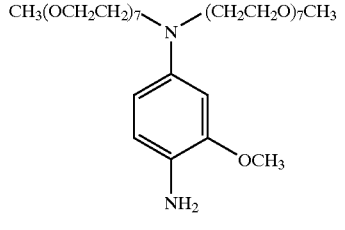
A2-42) 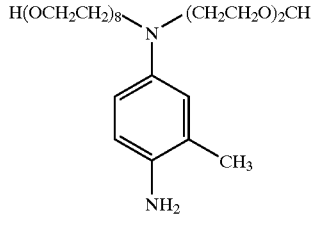

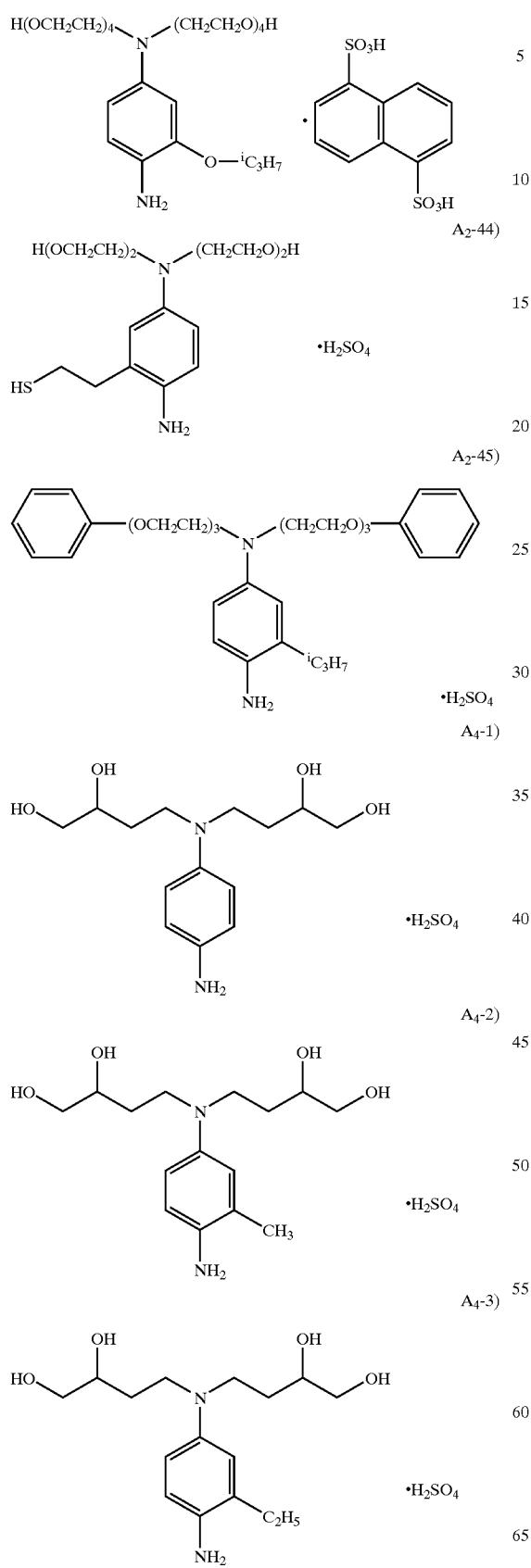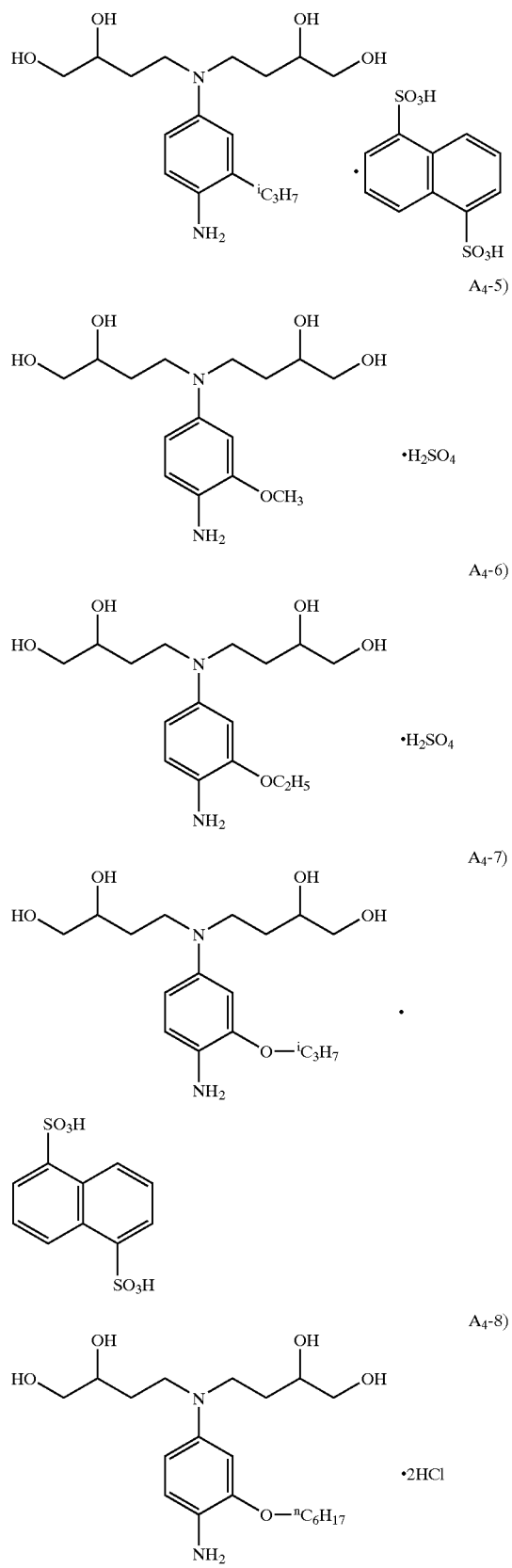

-continued
A₄-9) 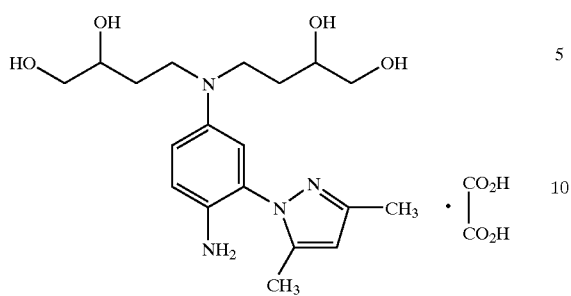 · $CO_2H\ CO_2H$
A₄-10) 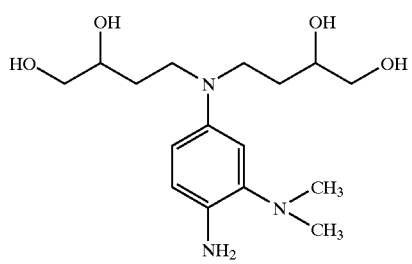 · $H_3PO_4$
A₄-11) 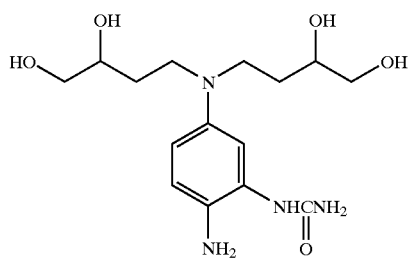 · $H_2SO_4$
A₄-12) 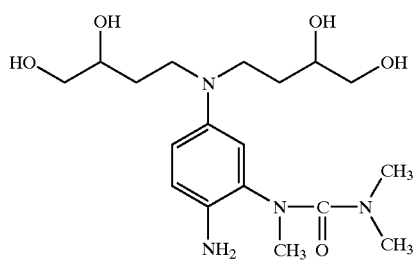 · $H_2SO_4$
A₄-13) 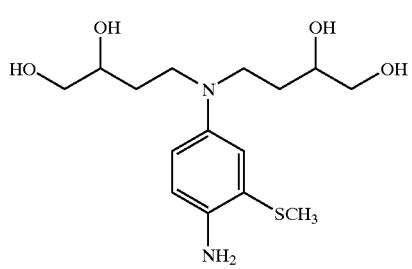 · $H_2SO_4$
-continued
A₄-14) 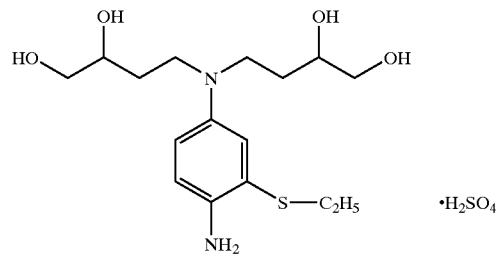 · $H_2SO_4$
A₄-15) 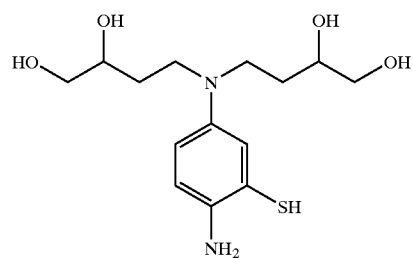 ·
A₄-16) 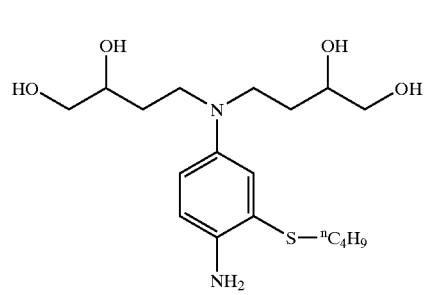 · $H_2SO_4$
A₄-17) 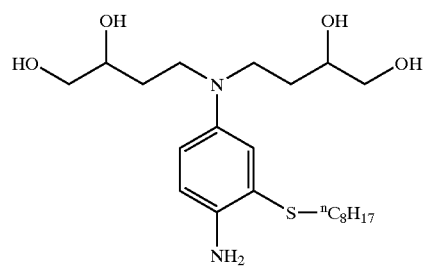 · $H_2SO_4$
A₄-18) 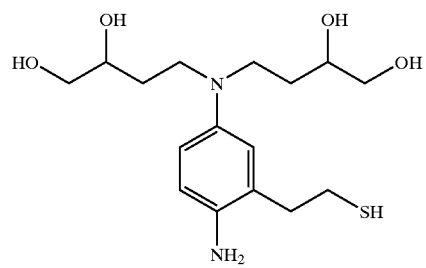 · $H_2SO_4$

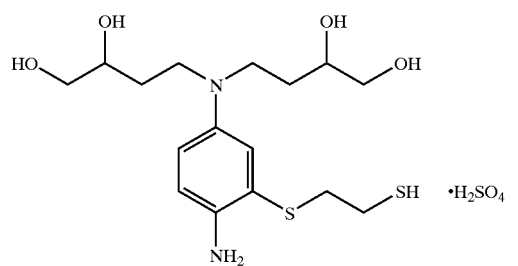
A4-19)
·H2SO4
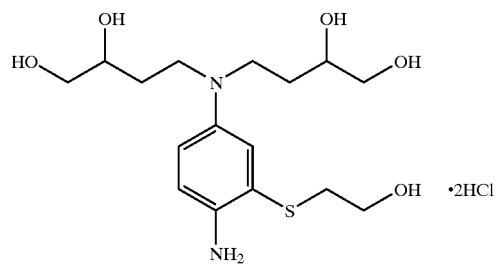
A4-20)
·2HCl
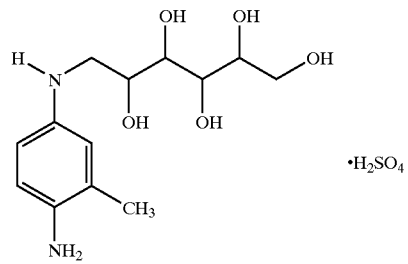
A4-21)
·H2SO4
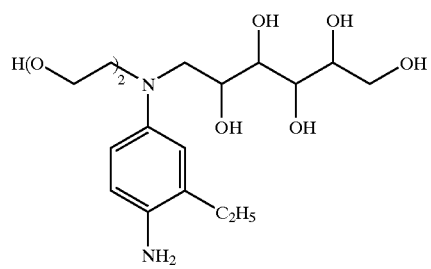
A4-22)
·H2SO4
A4-23)
·2HCl
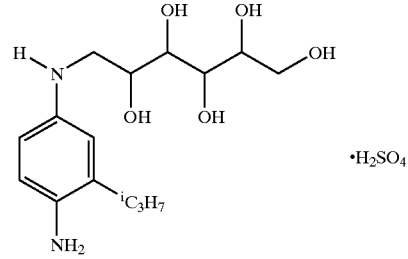
A4-24)
·H2SO4
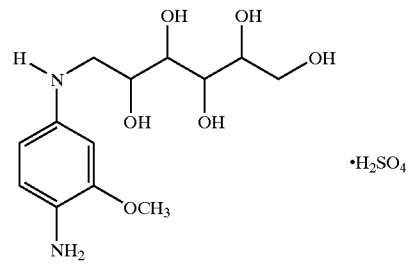
A4-25)
·H2SO4
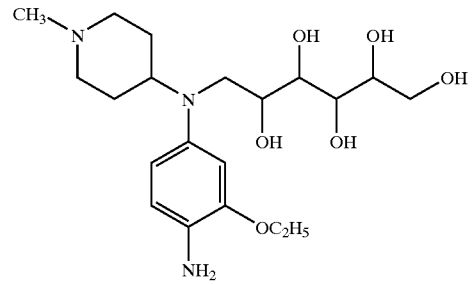
A4-26)
·3HCl
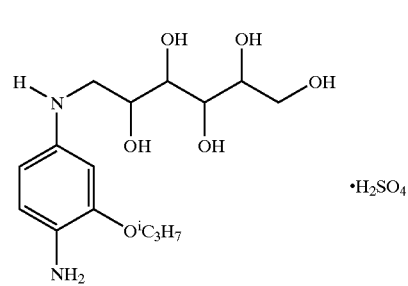
A4-27)
·H2SO4
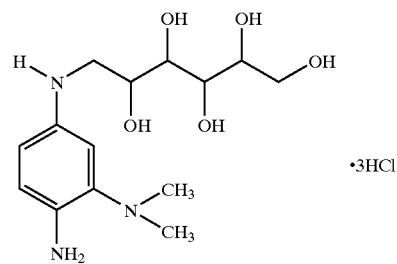
A4-28)
·3HCl

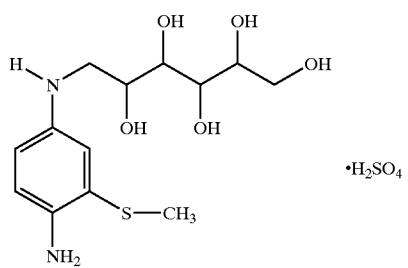 A4-29)
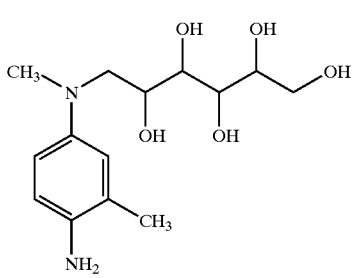 A4-34)
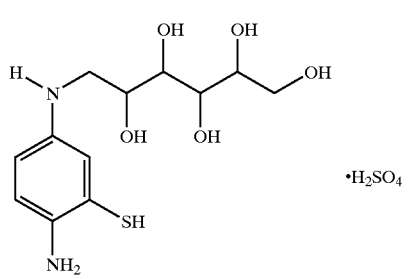 A4-30)
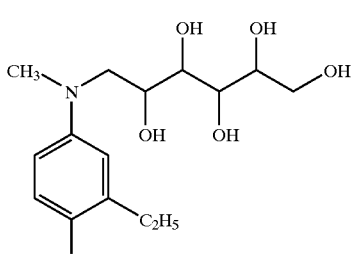 A4-35)
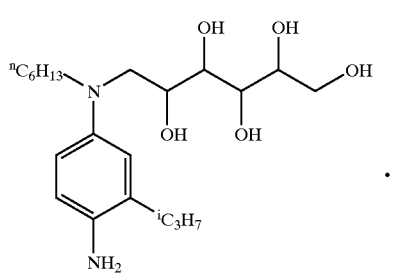 A4-31)
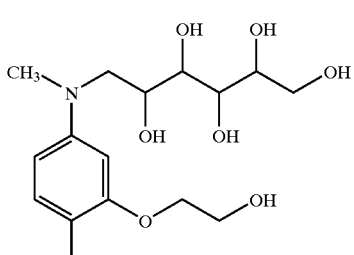 A4-36)
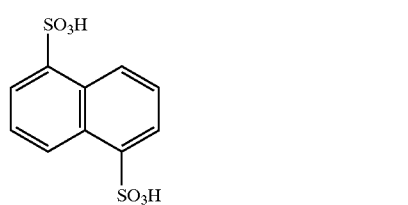 A4-32)
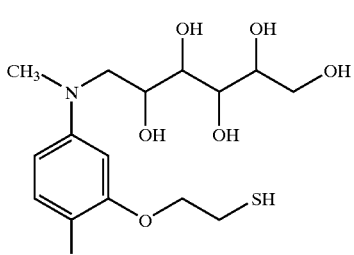 A4-37)
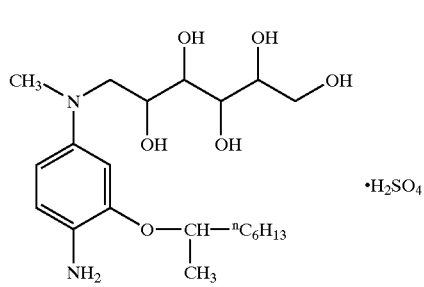 A4-33)
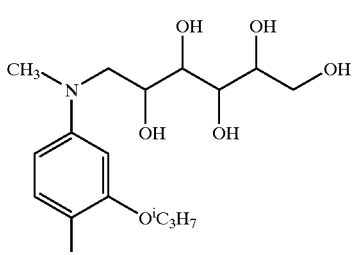 A4-38)
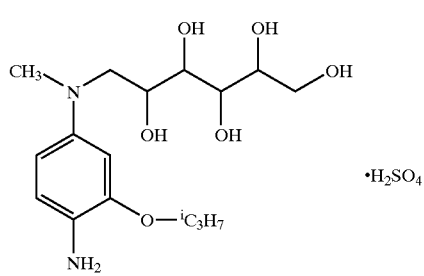

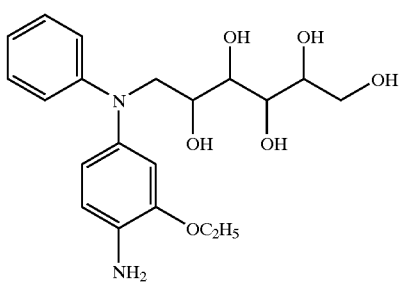

A4-39)

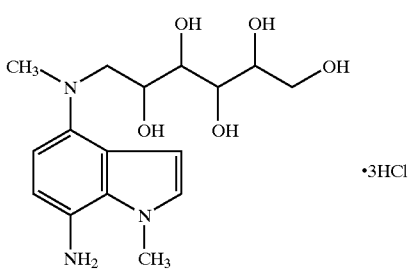

A4-40)

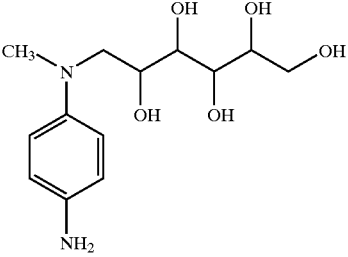

A4-41)

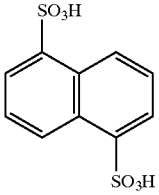

The relationship between these compounds and the general formulae (I) to (V) given above is as follows:

| | |
|---|---|
| A-1 to A-55 | General formula (I) |
| A$_2$-1 to A$_2$-25 | General formula (II) |
| A$_2$-26 to A$_2$-45 | General formula (III) |
| A$_4$-1 to A$_4$-20 | General formula (IV) |
| A$_4$-21 t A$_4$-41 | General formula (V) |

4-Amino-N,N-dialkylaniline compounds represented by the general formula (I) of the present invention can be synthesized on the basis of, for example, Journal of the American Chemical Society, Vol. 73, p. 3100 (1951). They can be synthesized also according to the following synthesizing scheme 1 or processes based thereon.

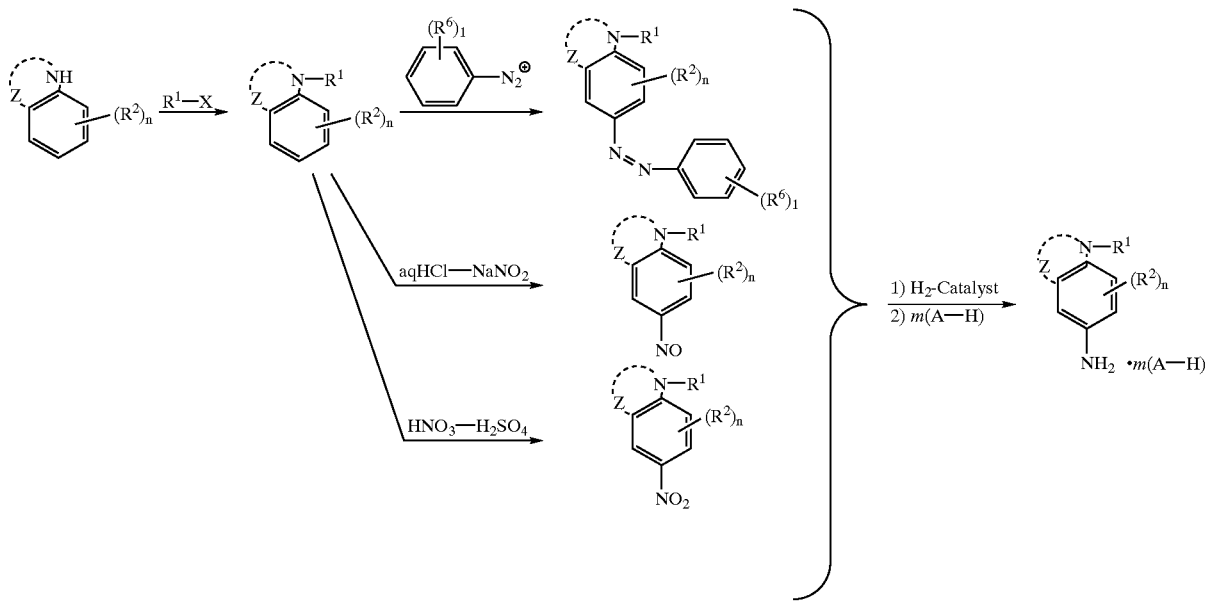

The compounds represented by the general formula (II) or (III) of the present invention can be synthesized by the following synthesizing scheme 2 or processes based thereon. The compounds represented by the general formula (IV) or (V) of the present invention can be synthesized according to the following synthesizing scheme 3 or processes based thereon.

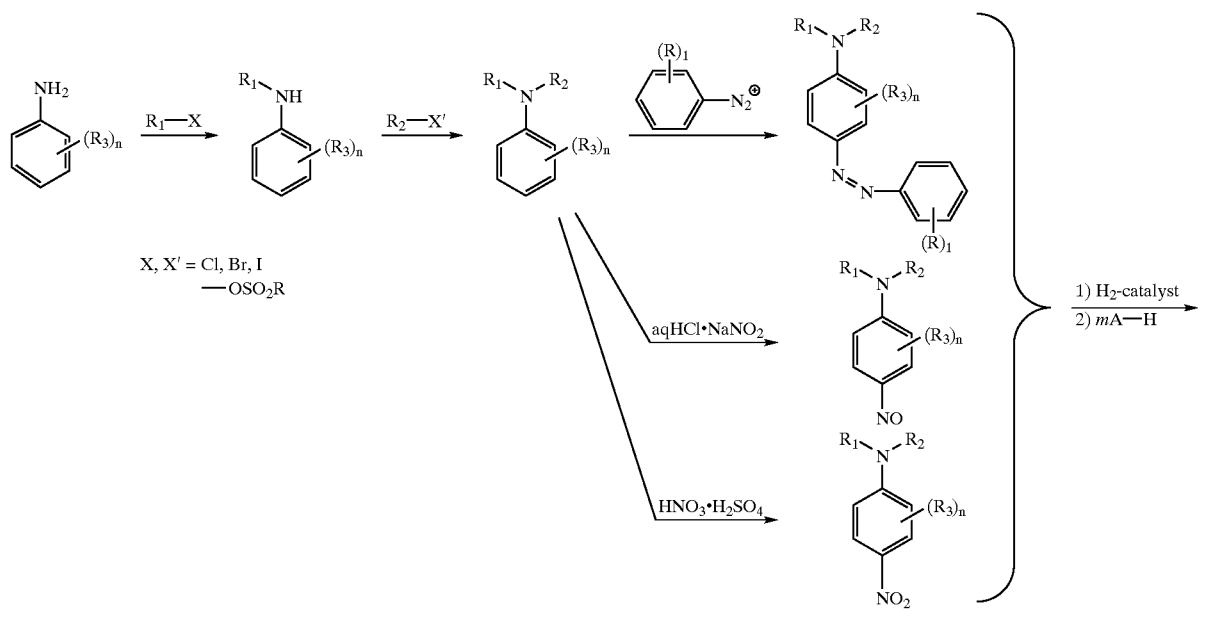
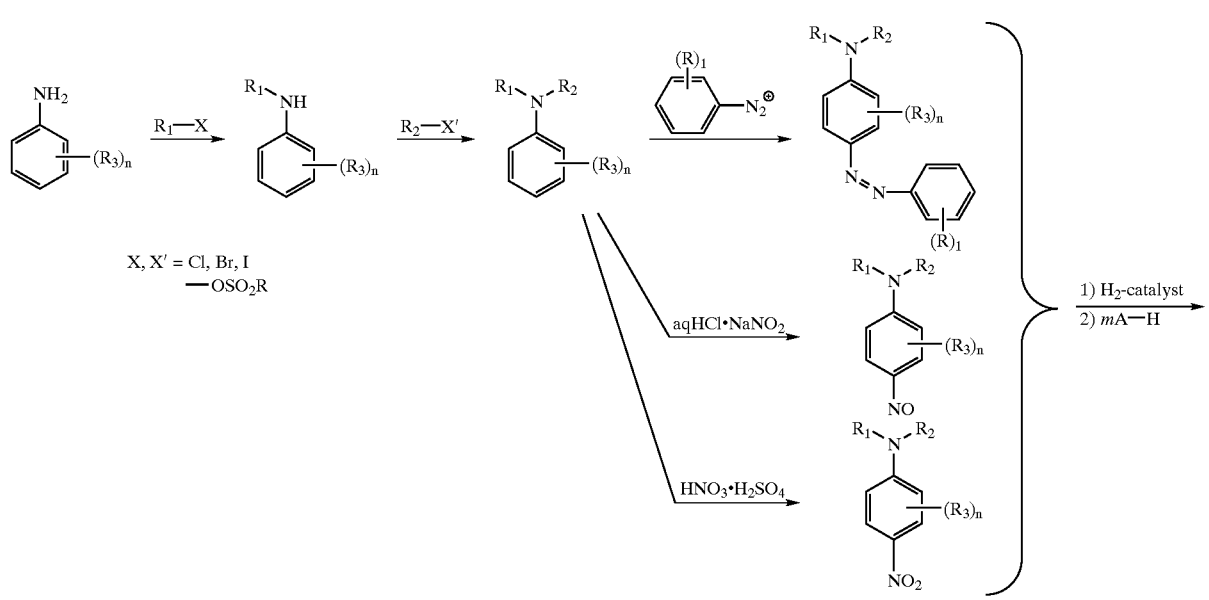
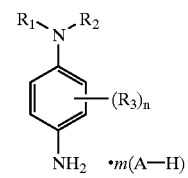

These compounds are synthesized by introducing an alkyl group, aryl group, heterocyclic group or the like into an amino group of an aniline forming a condensed ring with benzene. Namely, the starting compound is reacted with a halide, alkyl sulfonate, aryl sulfonate or the like. Then azo coupling at the p-position of the amino group is conducted, or a nitroso group or nitro group is introduced thereinto. The product is reduced (by the catalytic hydrogenation, reduction with zinc under acidic conditions, reduction with reducing iron or the like) and then converted into a salt with an acid to obtain the intended product.

The alkylation reaction is carried out by using one to five equivalents, preferably one to three equivalents, of a corresponding alkylating agent (per one equivalent of the alkylation) selected from among alkyl halides (alkyl chlorides, alkyl bromides and alkyl iodides) and alkyl sulfonates (such as alkyl mesylates and alkyl tosylates) and alkyl esters (such as alkyl acetates and alkyl benzoates)] in the presence of one to five equivalents (per one equivalent of the alkylation), preferably one to three equivalents, of an organic base (such as triethylamine or diazabicycloundecene) or an inorganic base (such as sodium hydrogencarbonate, sodium carbonate, potassium carbonate, sodium hydroxide or potassium hydroxide); without using any solvent or in a solvent such as water, an amide solvent (such as N,N-dimethylacetamide, N,N-dimethylformamide or 1-methyl-2-pyrrolidone), a sulfone solvent (such as sulfolane), a sulfoxide solvent (such as dimethyl sulfoxide), an ureido solvent (such as tetramethylurea), an ether solvent (such as dioxane) or an alcohol solvent (such as isopropyl alcohol or butanol); in the absence or presence of a catalyst (such as sodium iodide); at a reaction temperature in the range of 0 to 200° C., preferably 80 to 170° C.; for a reaction time in the range of 10 minutes to 72 hours, preferably 30 minutes to 12 hours.

Then the azo coupling at the p-position to the amino group is conducted, or a nitroso group or nitro group is introduced thereinto. An embodiment of the azo coupling reaction is as follows: A substituted or unsubstituted aniline is converted into a diazonium salt thereof in the presence of an acid (organic or inorganic acid such as hydrochloric acid, sulfuric acid, methanesulfonic acid or acetic acid) without using any solvent or in water or an organic solvent (such as an alcohol solvent, e.g. methanol, ethanol or isopropyl alcohol; an amide solvent, e.g. N,N-dimethylacetamide, N,N-dimethylformamide or 1-methyl-2-pyrrolidone; a sulfone solvent, e.g. sulfolane; a sulfoxide solvent, e.g. dimethyl sulfoxide; or a ureido solvent, e.g. tetramethylurea) at a temperature in the range of −78 to 40° C., preferably −20 to 30° C. for a reaction time in the range of five minutes to five hours, preferably five minutes to one hour; and then one to five equivalents, preferably one to two equivalents, of the diazonium salt is coupled with an N,N-dialkylaniline without using any solvent or in water or an organic solvent (such as an alcohol solvent, e.g. methanol, ethanol or isopropyl alcohol; an amide solvent, e.g. N,N-dimethylacetamide, N,N-dimethylformamide or 1-methyl-2-pyrrolidone; a sulfone solvent, e.g. sulfolane, a sulfoxide solvent, e.g. dimethyl sulfoxide; or a ureido solvent, e.g. tetramethylurea) at a temperature in the range of −78 to 40° C., preferably −20 to 30° C. for a reaction time in the range of five minutes to five hours, preferably five minutes to one hour. The coupling reaction is preferably conducted under a weakly acidic to weakly basic condition. The nitrosation is conducted by, for example, using one to five equivalents, preferably one to two equivalents, of an organic nitrosating agent (such as isoamyl nitrite) or an inorganic nitrosating agent (such as sodium nitrite) in the presence of, for example, an acid (organic or inorganic acid such as hydrochloric acid, sulfuric acid, methanesulfonic acid or acetic acid) without using any solvent or in water or an organic solvent (such as an alcohol solvent, e.g. methanol, ethanol or isopropyl alcohol; an amide solvent, e.g. N,N-dimethylacetamide, N,N-dimethylformamide or 1-methyl-2-pyrrolidone; a sulfone solvent, e. g. sulfolane; a sulfoxide solvent, e.g. dimethyl sulfoxide; or a ureido solvent, e.g. tetramethylurea) at a temperature in the range of −78 to 40° C., preferably −20 to 30° C. for a reaction time in the range of five minutes to five hours, preferably five minutes to one hour. The nitration is conducted by, for example, using one to five equivalents, preferably one to 1.5 equivalents, of a varied concentration (60 to 98%) of nitric acid alone or in combination with an activator such as sulfuric acid, sulfuric anhydride, acetic anhydride or trifluoroacetic acid without using any solvent or in water or an organic solvent (such as an alcohol solvent, e.g. methanol, ethanol or isopropyl alcohol; an organic acid, e.g. acetic acid; an organic acid anhydride, e.g. acetic anhydride or trifluoroacetic anhydride; an amide solvent, e.g. N,N-dimethylacetamide, N,N-dimethylformamide or 1-methyl-2-pyrrolidone; a sulfone solvent, e.g. sulfolane; a sulfoxide solvent, e.g. dimethyl sulfoxide; or a ureido solvent, e.g. tetramethylurea) at a temperature in the range of −78 to 100° C., preferably −20 to 30° C., for a reaction time in the range of five minutes to five hours, preferably five minutes to one hour.

Finally, the product is reduced by the catalytic reduction with hydrogen, reduction with zinc under an acidic condition or reduction with reduced iron to obtain the intended product. The catalytic reduction pith hydrogen is conducted, for example, in the presence of a catalyst (such as palladium-carbon or Raney nickel) without using any solvent or in water or an organic solvent (such as an alcohol, e.g. methanol, ethanol or isopropyl alcohol; an amide, e.g. N,N-dimethylacetamide, N,N-dimethylformamide or 1-methyl-2-pyrrolidone; a sulfone, e.g. sulfolane; a sulfoxide, e.g. dimethyl sulfoxide, or a ureido, e.g. tetramethylurea) at a reaction temperature in the range of 0 to 150° C., preferably 0 to 50° C., under a hydrogen pressure in the range of 1 to 500 atm, preferably 1 to 200 atm. for a reaction time in the range of 5 minutes to 72 hour s, preferably 1 to 8 hours. The reduction with reduced iron is conducted, for example, with 4 to 10 equivalents, preferably 4 to 6 equivalents, of reduced iron and 0.0001 to 1 equivalent, preferably 0.001 to 0.1 equivalent, of an acid (an inorganic acid such as hydrochloric acid or sulfuric acid; or an organic acid such as acetic acid or methanesulfonic acid) or an acid salt (such as ammonium chloride, sodium chloride or sodium sulfate) alone or in combination of two or more of them without using any solvent or in water or an organic solvent (such as an alcohol, e.g. methanol, ethanol or isopropyl alcohol; an amide, e.g. N,N-dimethylacetamide, N,N-dimethylformamide or 1-methyl-2-pyrrolidone; a sulfone, e.g. sulfolane; a sulfoxide, e.g. dimethyl sulfoxide; or a ureido, e.g. tetramethylurea) at a reaction temperature in the range of 0 to 150° C., preferably 50 to 100°° C., for a reaction time in the range of 30 minutes to 72 hours, preferably 1 to 8 hours. The reduction with zinc under an acidic condition is conducted by using 3 to 10 equivalents, preferably 3 to 6 equivalents, of zinc powder in the presence of an acid (an organic acid such as acetic acid or methanesulfonic acid; or an inorganic acid such as hydrochloric acid or sulfuric acid) without using any solvent or in water or an organic solvent (such as an alcohol, e.g. methanol, ethanol or isopropyl alcohol, an organic acid, e.g. acetic acid; an amide, e.g. N,N-dimethylacetamide, N,N-dimethylformamide or 1-methyl-2-pyrrolidone; a sulfone, e.g. sulfolane; a sulfoxide, e.g. dimethyl sulfoxide; a ureido, e.g. tetramethylurea; or an organic acid such as acetic acid, propionic acid or methanesulfonic acid) at a reaction temperature in the range of 0 to 150° C., preferably 0 to 100° C., for a reaction time in the range of 5 minutes to 72 hours, preferably 30 minutes to 3 hours.

The products obtained by the above-described reactions are after-treated as in ordinary organic synthesis reactions and then purified if necessary. Namely, for example, the product isolated from the reaction system can be used without the purification or after the purification by the recrystallization, column chromatography or the like, or a combination of these techniques. It is also possible to use the product, after the completion of the reaction, by distilling off the reaction solvent if necessary, pouring the product into water or ice, neutralizing it if necessary, and purifying the isolated product by the recrystallization, column chromatography or the like or by a combination of these techniques, if necessary. Alternatively, it is also possible to use the product, after the completion of the reaction, by distilling off the reaction solvent if necessary, pouring the product into water or ice, neutralizing it if necessary, extracting the product with an organic solvent and purifying the extract, if necessary, by the crystallization or column chromatography or by the combination of these techniques.

Then the description will be given on examples of the synthesis of various anilines each forming a condensed ring with a benzene ring.

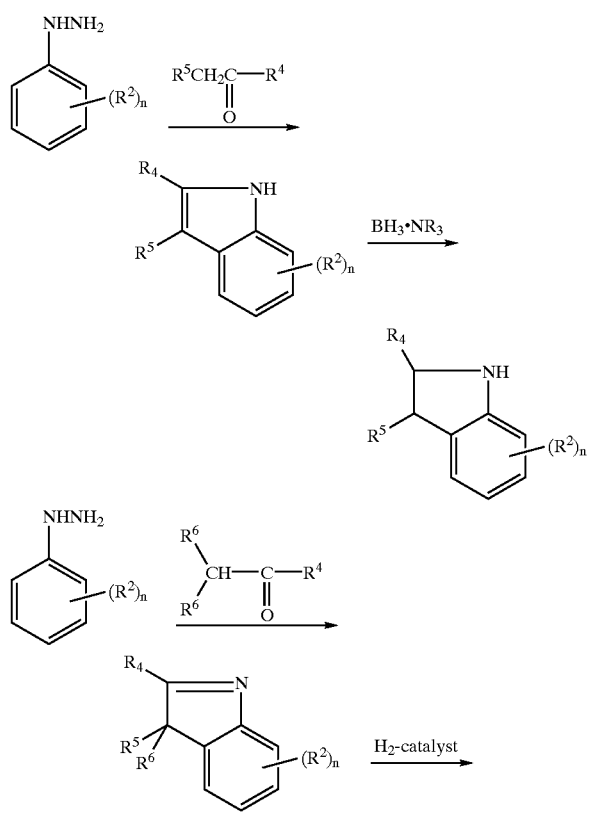

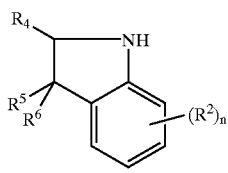

The dihydroindole skeleton is obtained by the Fischer's indole synthesis method from an arylhydrazine, followed by the reduction of the obtained indole compound or indolenine compound.

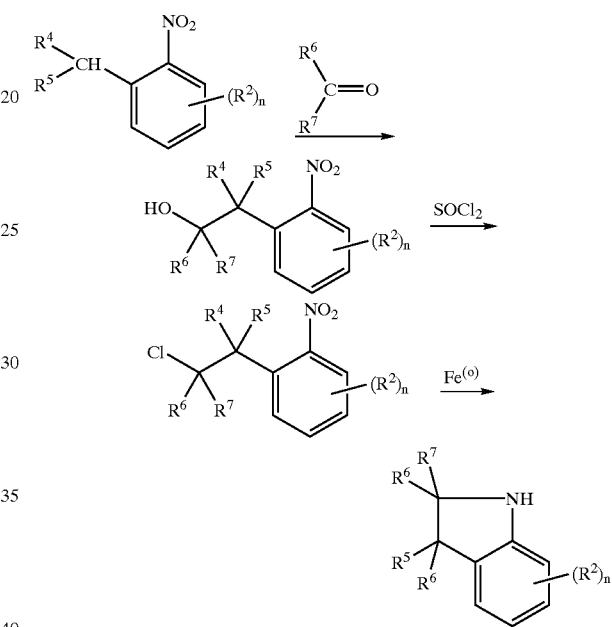

Alternatively, a hydroxymethyl group is introduced in the benzyl position, the obtained product is chlorinated and then fused with the amino group at the 2-position of the benzene ring according to a method described in Journal of the Organic Chemistry, Vol. 55, P. 580 (1990).

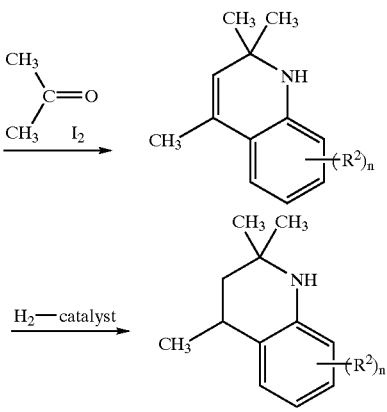

The tetrahydroquinoline skeleton can be dehydration-condensed with aniline and acetone and then the obtained product is reduced to obtain corresponding 2,2,4-trimethyltetrahydroquinoline according to a method described in Organic Synthesis Collective Volume, Vol. III, p. 328.

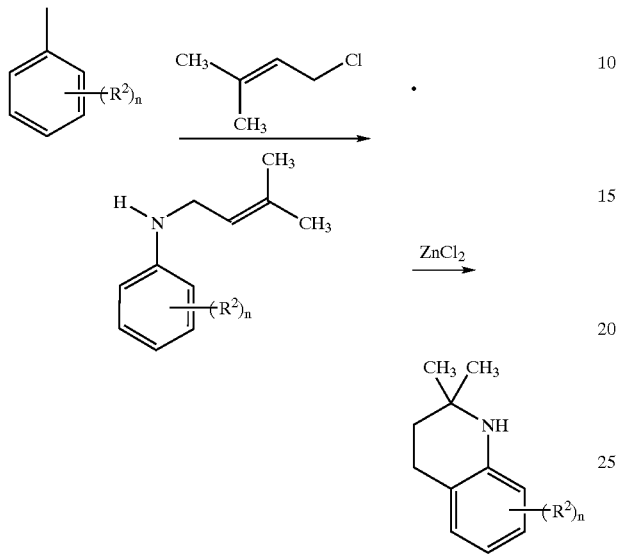

It is also possible to use N-allylaniline and zinc (II) chloride to obtain a corresponding tetrahydroquinoline according to a method described in Nippon Kagaku Kaishi (Journal of Chemical Society Japan) P. 1043 (1981) as described above.

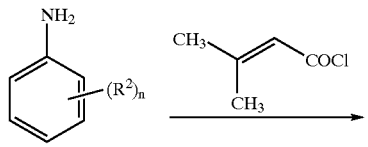

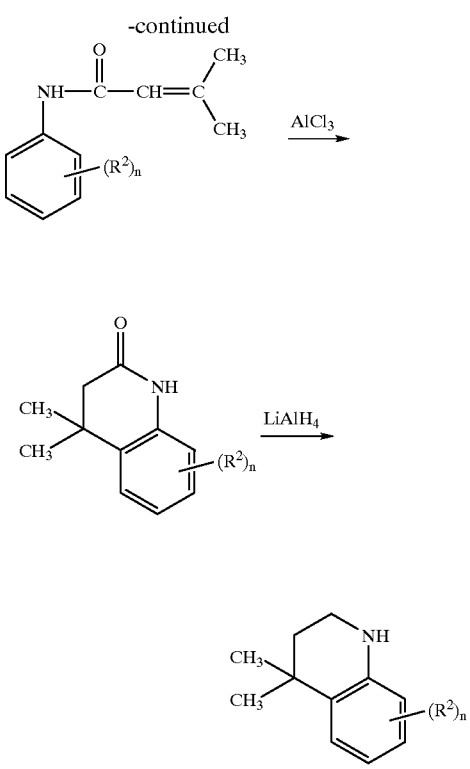

Further, the tetrahydroquinoline skeleton can be obtained by the Friedel-Crafts reaction of an α,β-unsaturated amide and the reduction of the amide according to a method described in Journal of the Americann Chemical Society, Vol. 62, p. 778 (1940) as described above.

Thus, various substituents can be introduced into the propylene chain in the tetrahydroquinoline structure by using the intermediates constituting the basic skeleton. Examples of them are given below.

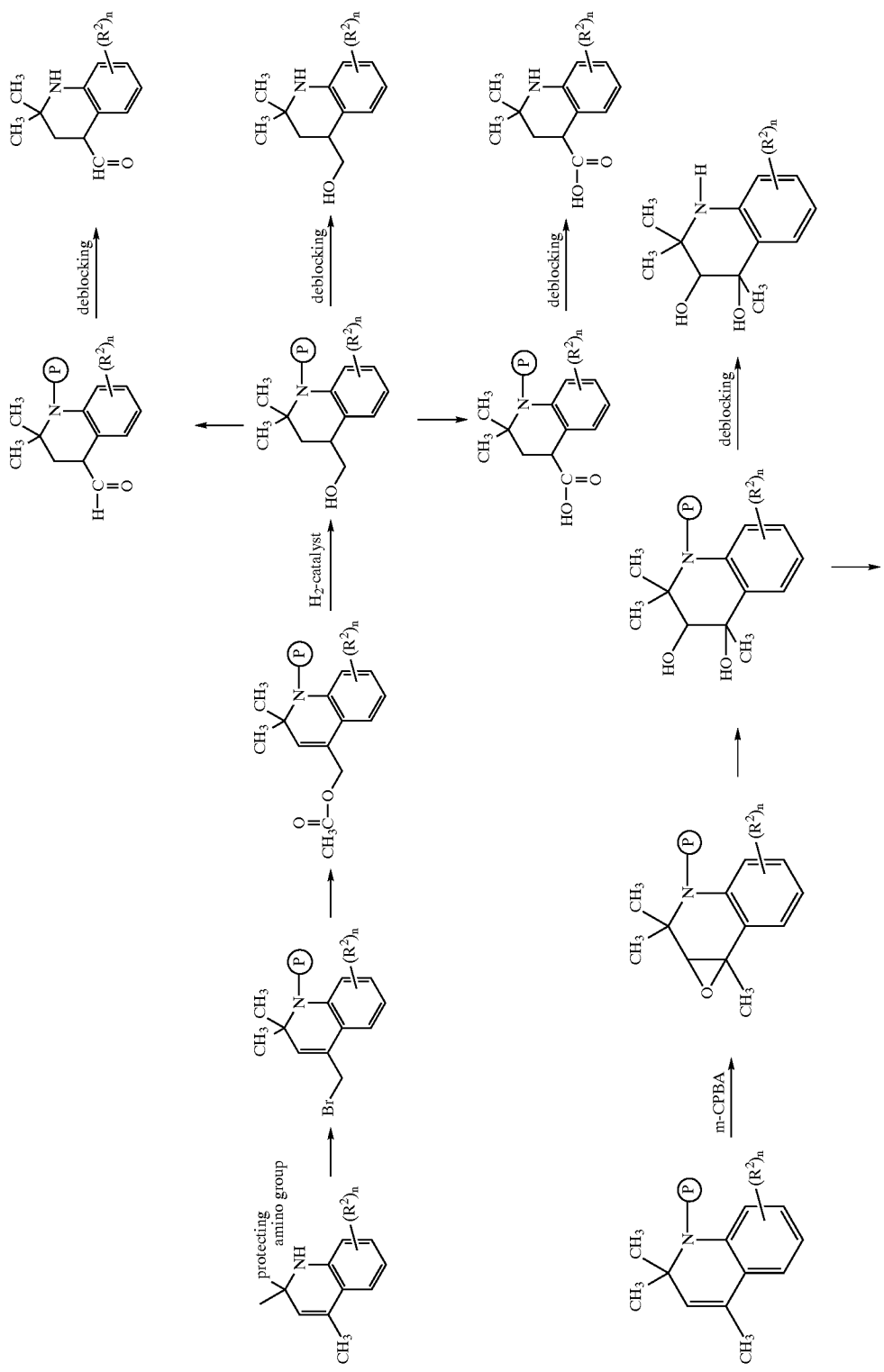

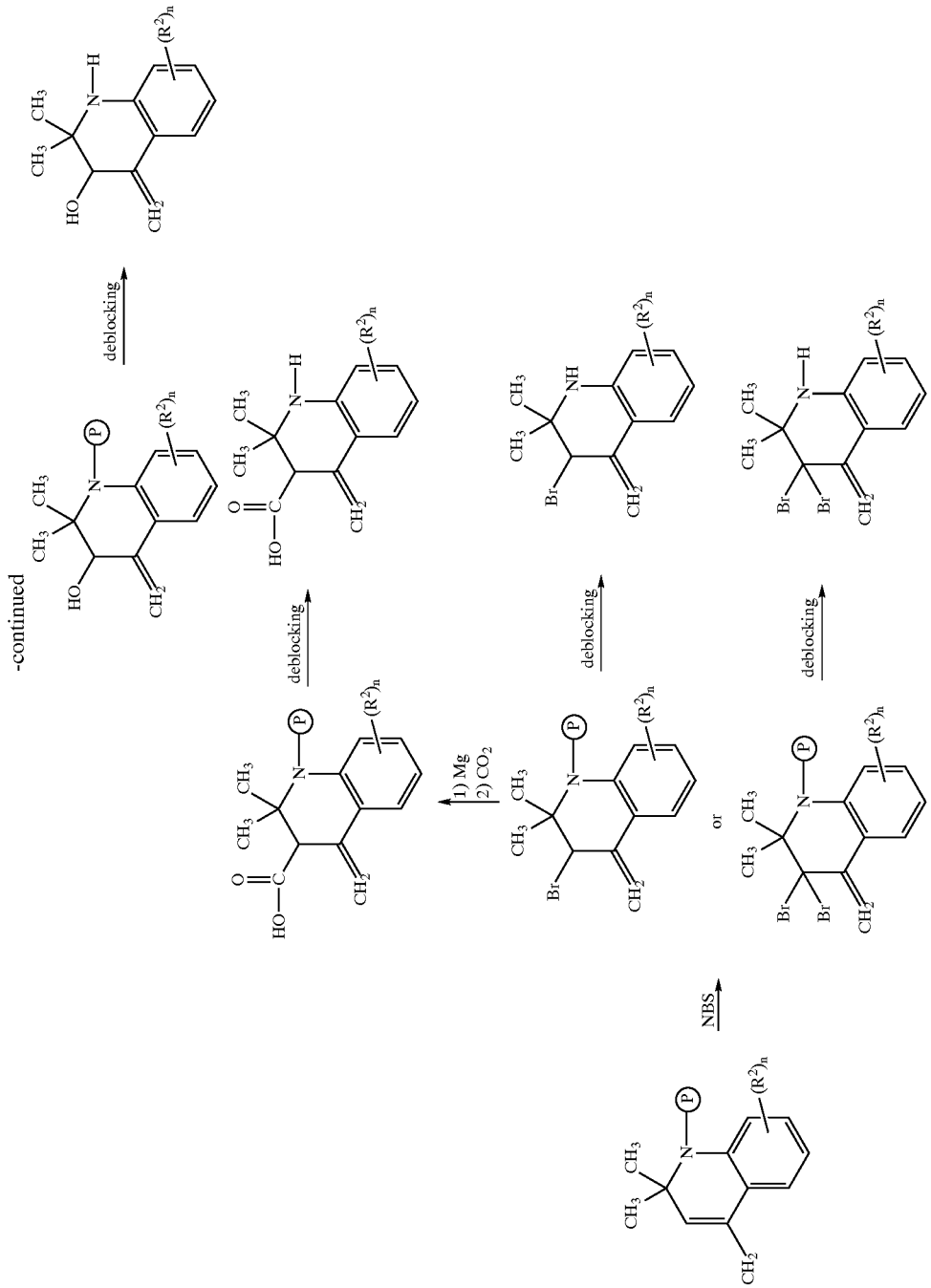

The compounds of general formula (II) can be synthesized by, for example, using a dihalide or by introducing two alkyl groups and then closing a ring by a carbon-to-carbon bond-forming reaction.

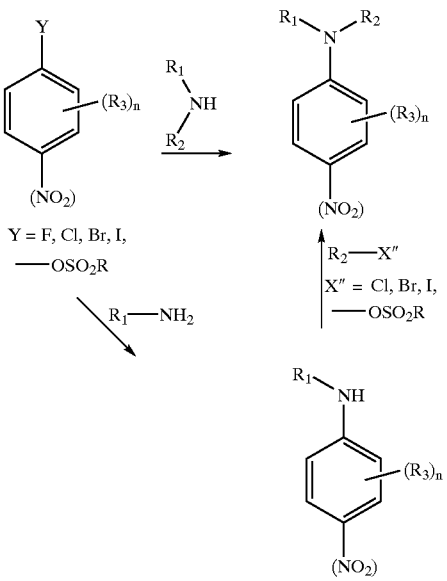

In the synthesis of the compounds of general formulae (II) to (V), the substitution reaction of a halobenzene compound with an amino compound can be employed as described above.

Further, as described above, the substitution reaction can be conducted by using a secondary amine compound having $R_1$ and $R_2$ or a primary amine compound having only $R_1$.

The substitution reaction is carried out by using, for example, one equivalent of a fluorobenzene compound, chlorobenzene compound, bromobenzene compound or iodobenzene compound as the halobenzene compound and one to five equivalents, preferably one to three equivalents, of the amino compound in the absence of any base or in the presence of one to five equivalents, preferably one to three equivalents, of an organic base (such as triethylamine or diazabicycloundecene) or an inorganic base (such as sodium hydrogencarbonate, sodium carbonate, potassium carbonate, sodium hydroxide or potassium hydroxide); without using any solvent or in a solvent such as water, an amide solvent (such as N,N-dimethylacetamide, N,N-dimethylformamide or 1-methyl-2-pyrrolidone), a sulfone solvent (such as sulfolane), a sulfoxide solvent (such as dimethyl sulfoxide), an ureido solvent (such as tetramethylurea), an ether solvent (such as diethyl ether, tetrahydrofuran or dioxane) or an alcohol solvent (such as methanol, ethanol, isopropyl alcohol, butanol or ethylene glycol) alone or in combination of two or more of them; in the absence or presence of a catalyst [such as copper (I) iodide, tetrakistriphenylphosphine palladium (0) or palladium chloride alone or in combination of two or more of them] at a reaction temperature in the range of 0 to 200° C., preferably 25 to 180° C.; for a reaction time in the range of 10 minutes to 72 hours, preferably 30 minutes to 12 hours. When a compound having a nitro group in the p-position to Y is used in this reaction, the first substitution reaction easily proceeds. This is effective for the synthesis of a compound of general formula (V) having a saccharide group at the N-position.

Examples for synthesizing the compounds of the present invention are given below.

SYNTHESIS EXAMPLE 1

The compound (A-9) of the present invention was synthesized according to the following reaction scheme:

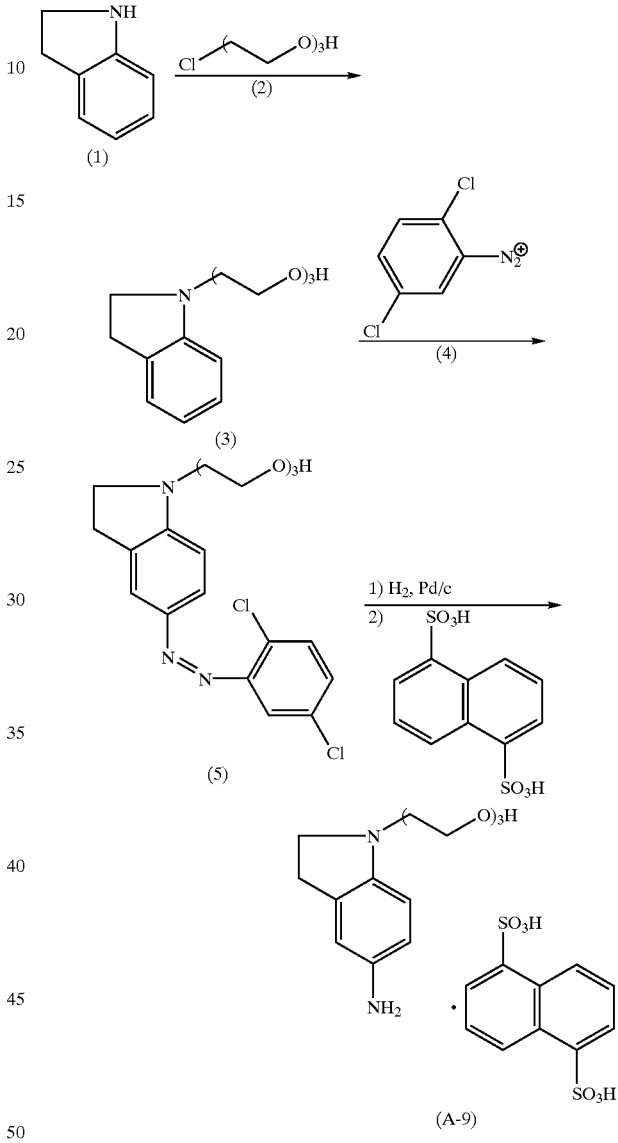

Synthesis of compound (3):

23.8 g of the compound (1), 15.0 g of sodium iodide, 34.0 g of sodium hydrogencarbonate and 70 ml of N,N-dimethylacetamide were fed into a three-necked flask. 37.8 ml of the compound (2) was dropped into the resultant mixture under stirring at an outer temperature of 130° C. for a period of 10 minutes. After the completion of the dropping, the stirring and heating were continued for 3 hours and then the reaction mixture was cooled to room temperature. 400 ml of ethyl acetate and 400 ml of water were added to the reaction mixture under stirring to conduct the extraction. The obtained ethyl acetate layer was washed with a mixture of 300 ml of water and 100 ml of saturated aqueous common salt solution four times and then dried over anhydrous sodium sulfate. The obtained product was concentrated with a rotary evaporator and then the residue was purified by silica gel column chromatography to obtain 29.4 g (yield: 58.5%) of the intended compound (3).

Synthesis of Compound (5):

28.4 g of 2,5-dichloroaniline and 300 ml of water were were fed into a three-necked flask. 59.3 ml of sulfuric acid was added thereto under stirring and under cooling with ice. A solution of 13.4 g of sodium nitrite in 25 ml of water was dropped into the resultant mixture for a period of 10 minutes while the inner temperature was kept at 8° C. or below. After the completion of the dropping, the stirring was continued for 30 minutes. 29.4 g of the compound (3), 96 g of sodium acetate, 67 ml of acetic acid and 200 ml of methanol were fed into another three-necked flask, and the diazonium salt solution prepared as described above was added thereto under stirring and under cooling with ice while the inner temperature was kept at 16° C. or below. In this step, the reaction was traced by TLC, and the addition of the diazonium salt solution was completed when the compound (3) had disappeared from the reaction system. After the completion of the addition, the stirring was continued for additional 30 minutes. Methanol was distilled off under reduced pressure. The reaction mixture was poured onto ice, and neutralized with a sodium hydroxide solution. After the extraction with 1.5 l of ethyl acetate and 500 ml of water, the obtained ethyl acetate layer was washed with a mixture of 700 ml of water and 200 ml of saturated aqueous common salt solution four times and then dried over anhydrous sodium sulfate. The obtained product was concentrated with a rotary evaporator and then the residue was purified by silica gel column chromatography to obtain 25.5 g (yield: 51%) of the intended compound (5).

Synthesis of Example Compound (A-9):

25.5 g of the compound (5), 2 g of palladium/carbon (10%) and 73 ml of methanol were fed into an autoclave and stirred at room temperature under a hydrogen pressure of 100 atm. for 5 hours. A solution of 2 1.6 g of naphthalene-1,5-disulfonic acid tetrahydrate in 40 ml of methanol was added to the reaction mixture. The obtained mixture was filtered, and the filtrate was concentrated with a rotary evaporator. 200 ml of ethyl acetate and 200 ml of water were added to the concentrate, and they were stirred to dissolve them and then they were separated to form layers. The aqueous layer thus obtained was washed with 200 ml of ethyl acetate three times. The aqueous layer thus obtained was concentrated with a rotary evaporator, and then crystals formed in a mixture of methanol and ethanol were taken by the filtration to obtain 22.2 g of the intended example compound (A-9) (yield: 67%).

NMR(D$_2$O): δ=8.82 (d, 2H, J=9.7 Hz), 8.20 (d, 2H, J=9.7 Hz), 7.73 (dd, 2H, J=9.7 Hz, J=9.7 Hz), 7.28 (s, 1H), 7.2–7.4 (m, 2H), 3.80 (t, 2H, J=8.3 Hz), 3.4–3.7 (m, 15H), 3.10 (d, 2H, J=8.3 Hz).

SYNTHESIS EXAMPLE 2

The example compound (A-37) of the present invention was synthesized according to the following reaction scheme:

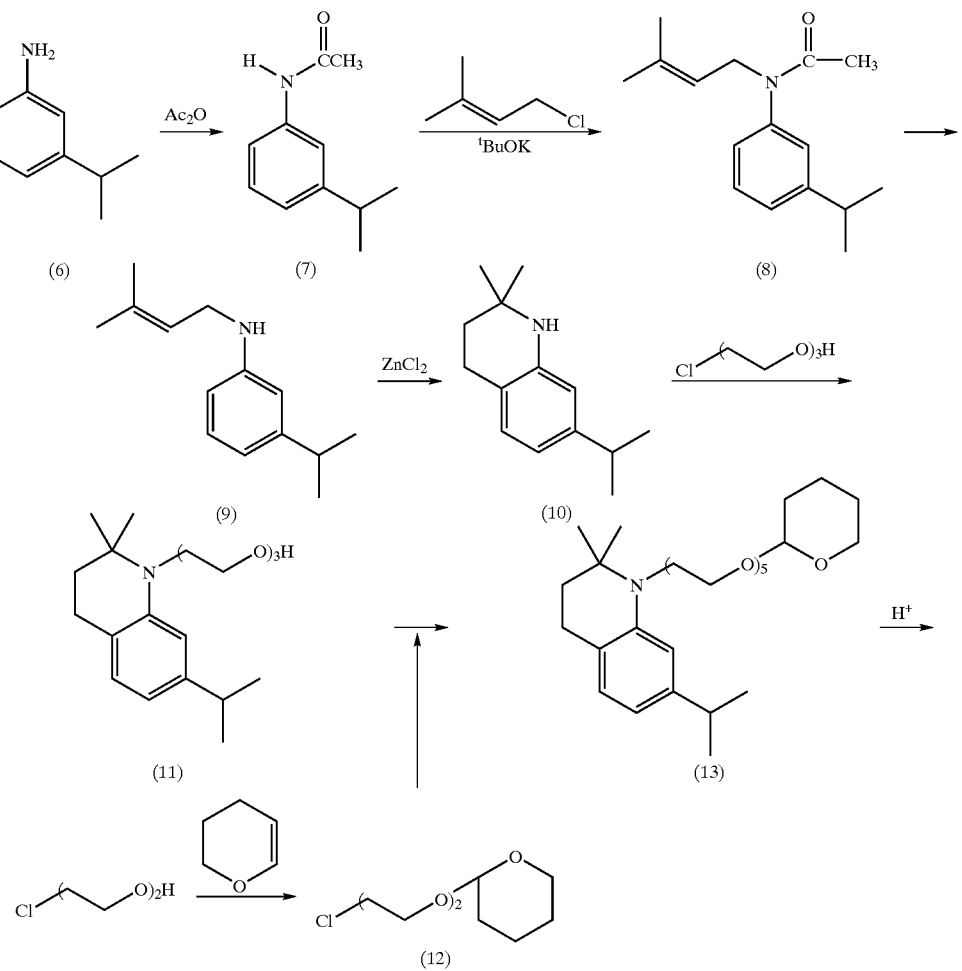

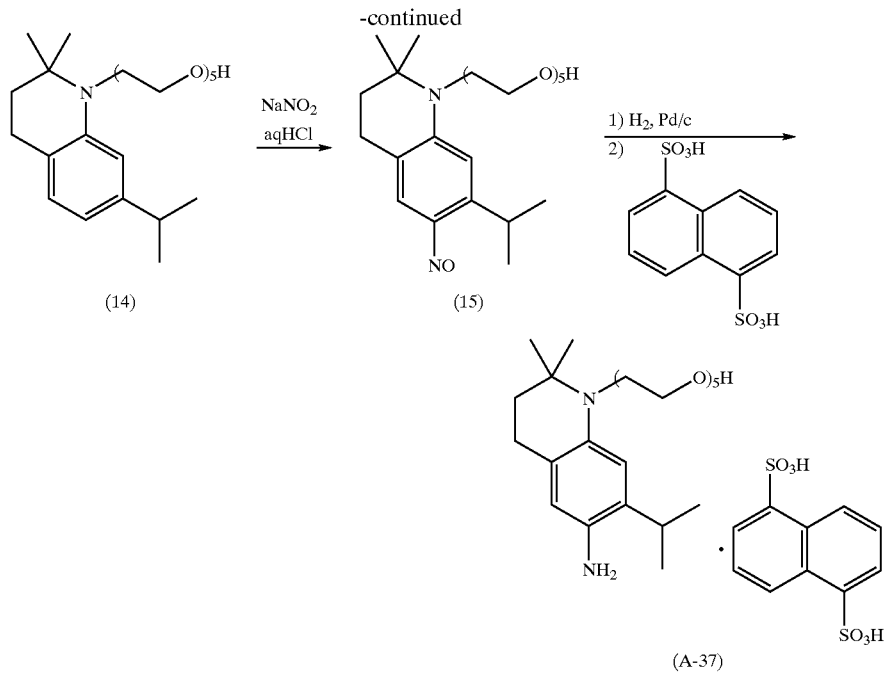

Synthesis of Compound (7):

472 ml of acetic anhydride was fed into a three-necked flask. 270.4 g of the compound (6) was dropped thereinto under stirring, and under heating under reflux for a period of 30 minutes. After the completion of the dropping, the stirring, heating and reflux were continued for 3 hours and 90 ml of water was dropped for a period of 15 minutes to lower the inner temperature to 30° C. 1 l of ethyl acetate and 1 l of water were added to the reaction mixture to conduct the extraction. The obtained ethyl acetate layer was washed with a mixture of 800 ml of water and 200 ml of saturated aqueous common salt solution three times and then dried over anhydrous sodium sulfate. The obtained product was concentrated with a rotary evaporator to obtain 390 g of the intended compound (7) as the crude product, which was directly subjected to the subsequent step.

Synthesis of compound (8):

1 l of N,N-dimethylacetamide was added to the compound (7), obtained as described above, under stirring to obtain a solution. 246.9 g of potassium t-butoxide was added to the solution at room temperature and the resultant mixture was stirred for 1 hour. The mixture was cooled to an inner temperature of −5° C. in an ice/methanol bath. 247.9 ml of purenyl chloride was dropped thereinto under stirring for a period of 1 hour. In this step, the inner temperature was elevated to 7° C. After the completion of the dropping, the ice/methanol bath was removed and the reaction mixture was stirred for 2 hours. After the extraction with 2 l of ethyl acetate and 1.5 l of water, the obtained ethyl acetate layer was washed with a mixed solution of 1 l of water and 200 ml of saturated aqueous common salt solution four times and then dried over anhydrous sodium sulfate. The obtained product was concentrated with a rotary evaporator to obtain the intended compound (8) as the crude product, which was directly subjected to the subsequent step.

Synthesis of Compound (9):

1.2 l of ethanol was added to the compound (8), obtained as described above, to form a solution. A solution of 320 g of sodium hydroxide in 320 ml of water was dropped into the solution under heating under reflux for 20 minutes. The heating under reflux was continued for 3 hours, and the solution of 320 g of sodium hydroxide in 320 ml of water was dropped again into the mixture for 20 minutes. The heating under reflux was continued for additional 3 hours, and a solution of 160 g of sodium hydroxide in 160 ml of water was dropped thereinto for a period of 5 minutes. The resultant mixture was stirred under heating under reflux for 10 hours. The solution was distilled under reduced pressure. 1544 ml oof concentrated hydrochloric acid was dropped thereinto under cooling with ice for one hour. The inner temperature rose to 30° C. in this step. After the extraction with 1.5 l of ethyl acetate, the ethyl acetate layer thus obtained was washed with a mixed solution of 1 of water and 200 ml of saturated aqueous common salt solution four times, and then dried over anhydrous sodium sulfate. The product was concentrated with a rotary evaporator. The obtained residue was purified by silica gel column chromatography to obtain 305.7 g of the intended compound (9) (yield: 75%) as the oily product.

Synthesis of Compound (10):

305.7 g of the compound (9) and 500 ml of xylene were fed into a three-necked flask. Then 613 g of zinc (II) chloride was added thereto under stirring, and the resultant mixture was stirred under heating under reflux for 3 hours. After cooling to 70° C. followed by the extraction with 1.5 l of ethyl acetate and 1.5 l of water, the ethyl acetate layer thus obtained was washed with an aqueous solution of 80 g of sodium hydroxide in 1 l of water three times and then with a mixture of 200 ml of saturated aqueous common salt solution and 800 ml of water three times. The ethyl acetate layer was dried over anhydrous sodium sulfate. The product was concentrated with a rotary evaporator. The obtained residue was purified by silica gel column chromatography to obtain 174.2 g of the intended compound (10) (yield: 57%) as the oily product.

Synthesis of Compound (11):

87.1 g of the compound (10), 288 g of sodium hydrogencarbonate, 64.2 g of sodium iodide and 200 ml of N,N-dimethylacetamide were fed into a three-necked flask, and the obtained mixture was stirred under heating to an inner temperature of 120° C. 145 g of 2-[2-(2-chloroethoxy) ethoxy]ethanol was dropped into the mixture for a period of 1 hour. After the completion of the dropping, the stirring was continued at an inner temperature of 130° C. for 13 hours and then cooled to 30° C. 600 ml of ethyl acetate and 500 ml of water were added to the reaction mixture to conduct the extraction. The obtained ethyl acetate layer was washed with a mixture of 100 ml of saturated aqueous common salt solution and 400 ml of water four times and then dried over anhydrous sodium sulfate. The obtained product was concentrated with a rotary evaporator and then purified by silica gel column chromatography to obtain 84.6 g (yield: 59%) of the intended compound (11) as the oily product.

Synthesis of Compound (12):

249 g of 2-(2-chloroethoxy)ethanol, 3.8 g of p-toluenesulfonic acid monohydrate and 590 ml of dichloromethane were fed into a three-necked flask. 500 ml of dihydropyrane was dropped into the resultant mixture under stirring at room temperature for a period of 30 hours. In the course of the dropping, the temperature of the reaction system was elevated and the reflux state started. After the completion of the dropping, the stirring was continued under these conditions for 3 hours. 10 g of sodium hydrogencarbonate was added to the reaction mixture and the whole mixture was stirred for additional 10 minutes. The mixture was poured into a mixture of 100 g of sodium hydrogencarbonate and ice/water. 590 ml of dichloromethane was added to the reaction mixture to conduct the extraction. The obtained dichloromethane layer was washed with a mixture of 100 ml of saturated aqueous common salt solution and 400 ml of water four times and then dried over anhydrous sodium sulfate. 4 g of sodium hydroxide was added thereto and the obtained mixture was concentrated with a rotary evaporator and then the residue was distilled to collect a fraction of 88 to 100° C./0.2 mmHg. Thus 350 g (yield: 84%) of the intended compound (12) was obtained.

Synthesis of Compound (13):

84.1 g of the compound (11), 14.06 g of potassium hydroxide and 200 ml of toluene were fed into a three-necked flask. 131 g of the compound (12) was dropped into the mixture for a period of 2 hours. After the completion of the dropping, the stirring was continued under heating under reflux, and toluene was distilled off under reduced pressure. 500 ml of dichloromethane and 300 ml of water were added to the reaction mixture to make it acidic. Then the mixture was neutralized with 250 ml of sodium hydrogencarbonate. A dichloromethane layer obtained by the extraction was washed with a mixture of 100 ml of saturated aqueous common salt solution and 400 ml of water three times and then dried over anhydrous sodium sulfate. The obtained product was concentrated with a rotary evaporator to obtain the intended compound (13) as the crude product, which was directly subjected to the subsequent step.

Synthesis of Compound (14):

500 ml of methanol was added to the compound (13) obtained as described above to form a solution. 21.5 ml of concentrated hydrochloric acid was added to the solution, and they were directly stirred for 1 hour. The solvent was distilled off under reduced pressure. 500 ml of ethyl acetate and 300 ml of water were added to the residue to dissolve it. After the neutralization with sodium hydrogencarbonate followed by the extraction, the resultant ethyl acetate layer was washed with a mixture of 50 ml of saturated aqueous common salt solution and 300 ml of water four times and then dried over anhydrous sodium sulfate. The obtained product was concentrated with a rotary evaporator, and the obtained residue was purified by the silica gel column chromatography to obtain 84.7 g (yield: 80%) of the intended compound (14) as the oily product.

Synthesis of Compound (15):

84.7 g of the compound (14), 56.6 ml of concentrated hydrochloric acid and 40 ml of methanol were fed into a three-necked flask. An aqueous solution of 19.3 g of sodium nitrite in 20 ml of water was dropped into the mixture under stirring under cooling with ice for a period of 15 minutes. After the completion of the dropping, the ice bath was removed and the mixture was stirred for 5 hours. The reaction mixture was poured into 100 g of sodium hydrogencarbonate. After the extraction with 500 ml of ethyl acetate and 300 ml of water, the resultant ethyl acetate layer was washed with a mixture of 50 ml of saturated aqueous common salt solution and 50 ml of water three times and then dried over anhydrous sodium sulfate. The obtained product was concentrated with a rotary evaporator, and the obtained residue was purified by the silica gel column chromatography to obtain 44.6 g of the intended compound (15) as the oily product.

Synthesis of Example Compound (A-37):

44.6 g of the compound (15), 5 g of palladium/carbon (10%) and 100 ml of methanol were fed into an autoclave, and they were stirred at room temperature under hydrogen pressure of 100 atm. for 3 hours. A solution of 35.5 g of naphthalene-1,5-disulfonic acid tetrahydrate in 90 ml of methanol was added to the obtained reaction mixture. After the filtration, the obtained filtrate was stirred and crystals thus formed were obtained by the filtration. 58.5 g (yield: 82%) of the intended example compound (A-37) was thus obtained. NMR($D_2O$): δ=8.86 (d, 2H, J=9.7 Hz), 8.21 (d, 2H, J=9.7 Hz), 7.72 (dd, 2H, J=9.7 Hz, 9.7 Hz), 7.22 (s, 1H), 3.0–3.9 (m, 23H), 2.80 (t, 2H, J=8.0H z), 1.95 (t, 2H, J=8.0 Hz), 1.30 (s, 6H), 1.21 (d, 6H, J=8.4 Hz).

SYNTHESIS EXAMPLE 3

The compound (A-32) of the present invention was synthesized according to the following reaction scheme:

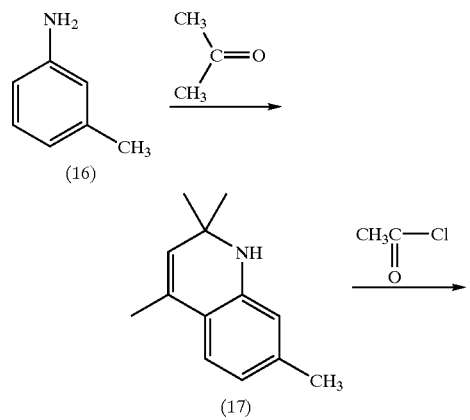

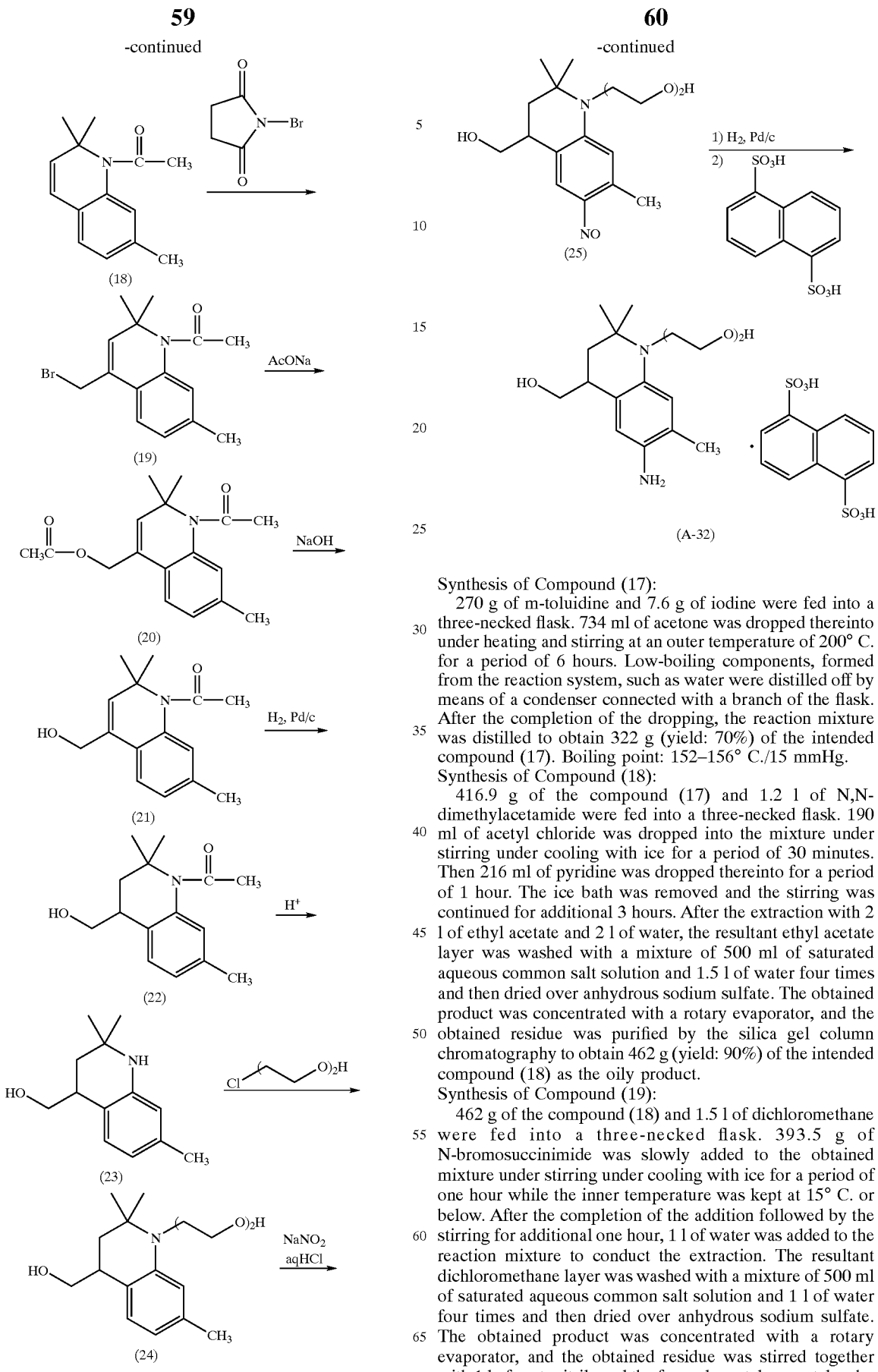

Synthesis of Compound (17):

270 g of m-toluidine and 7.6 g of iodine were fed into a three-necked flask. 734 ml of acetone was dropped thereinto under heating and stirring at an outer temperature of 200° C. for a period of 6 hours. Low-boiling components, formed from the reaction system, such as water were distilled off by means of a condenser connected with a branch of the flask. After the completion of the dropping, the reaction mixture was distilled to obtain 322 g (yield: 70%) of the intended compound (17). Boiling point: 152–156° C./15 mmHg.

Synthesis of Compound (18):

416.9 g of the compound (17) and 1.2 l of N,N-dimethylacetamide were fed into a three-necked flask. 190 ml of acetyl chloride was dropped into the mixture under stirring under cooling with ice for a period of 30 minutes. Then 216 ml of pyridine was dropped thereinto for a period of 1 hour. The ice bath was removed and the stirring was continued for additional 3 hours. After the extraction with 2 l of ethyl acetate and 2 l of water, the resultant ethyl acetate layer was washed with a mixture of 500 ml of saturated aqueous common salt solution and 1.5 l of water four times and then dried over anhydrous sodium sulfate. The obtained product was concentrated with a rotary evaporator, and the obtained residue was purified by the silica gel column chromatography to obtain 462 g (yield: 90%) of the intended compound (18) as the oily product.

Synthesis of Compound (19):

462 g of the compound (18) and 1.5 l of dichloromethane were fed into a three-necked flask. 393.5 g of N-bromosuccinimide was slowly added to the obtained mixture under stirring under cooling with ice for a period of one hour while the inner temperature was kept at 15° C. or below. After the completion of the addition followed by the stirring for additional one hour, 1 l of water was added to the reaction mixture to conduct the extraction. The resultant dichloromethane layer was washed with a mixture of 500 ml of saturated aqueous common salt solution and 1 l of water four times and then dried over anhydrous sodium sulfate. The obtained product was concentrated with a rotary evaporator, and the obtained residue was stirred together with 1 l of acetonitrile and the formed crystals were taken by filtration by suction to obtain 347.5 g (yield: 56%) of the intended compound (19).

Synthesis of Compound (20):

308.25 g of the compound (19), 600 ml of N,N-dimethylacetamide and 246 g of sodium acetate were fed into a three-necked flask and they were stirred under heating under reflux for 2 hours. After cooling the reaction mixture to 30° C., 1.25 l of water was dropped into the mixture and the obtained crystals were filtered by suction. 400 ml of acetonitrile was added to the crystals and the resultant mixture was heated to obtain a solution. After cooling with water, the resultant crystals were filtered by suction to obtain 244.3 g (yield: 85%) of the intended compound (20).

Synthesis of Compound (21):

244.3 g of the compound (20) was dissolved in 250 ml of tetrahydrofuran in a three-necked flask. 1 l of ethanol was added to the solution, and then an aqueous solution of 136 g of sodium hydroxide in 150 ml of water was added thereto under stirring. The resultant mixture was directly stirred for one hour and then the solvent was distilled off under reduced pressure. The residue was made acidic by adding 292 ml of concentrated hydrochloric acid, and then 800 ml of ethyl acetate and 400 ml of water were added thereto. After stirring followed by the neutralization with sodium hydrogencarbonate, the product was extracted. The ethyl acetate layer thus obtained was washed with a mixture of 100 ml of saturated aqueous common salt solution and 400 ml of water four times and then dried over anhydrous sodium sulfate. The obtained product was concentrated with a rotary evaporator to obtain the intended compound (21) as the crude product, which was directly subjected to the subsequent step.

Synthesis of Example Compound (22):

The compound (21) obtained as described above, 20 g of palladium/carbon (10%) and 400 ml of ethanol were fed into an autoclave, and they were stirred at an inner temperature of 50 to 60° C. under a hydrogen pressure of 100 atm. for 5 hours. The reaction mixture was filtered, and the obtained filtrate was concentrated with a rotary evaporator to obtain the intended compound (22) as the crude product, which was directly subjected to the subsequent step.

Synthesis of Example Compound (23):

The compound (22) obtained as described above and 500 ml of ethanol were fed into a three-necked flask. 146 ml of concentrated hydrochloric acid was added thereto under stirring, and the resultant mixture was stirred under heating under reflux. 96 ml of sulfuric acid was dropped into the mixture for a period of 10 minutes, and the stirring was continued under heating under reflux for additional 1 hour. After cooling to 30° C., the reaction mixture was added to 1 kg of sodium hydrogencarbonate to neutralize it. 1 l of ethyl acetate and 1 l of water were added thereto to conduct the extraction. The ethyl acetate layer thus obtained was washed with a mixture of 200 ml of saturated aqueous common salt solution and 800 ml of water four times and then dried over anhydrous sodium sulfate. The obtained product was concentrated with a rotary evaporator, and ethyl acetate and n-hexane were added to the residue. The crystals thus obtained were filtered by suction to obtain 125.7 g (yield: 72%) of the intended compound (23).

Synthesis of Example Compound (24):

58.0 g of the compound (23), 70.6 g of sodium hydrogencarbonate, 25.5 g of sodium iodide and 100 ml of N,N-dimethylacetamide were fed into a three-necked flask. 42.4 g of 2-(2-chloroethoxy)ethanol was dropped thereinto under heating and stirring at an outer temperature of 130° C. for a period of 20 minutes, and the resultant mixture was stirred under heating under reflux for 5 hours. After cooling to 30° C. with water, the product was extracted with 500 ml of ethyl acetate and 400 ml of water, the obtained ethyl acetate layer was washed with a mixture of 100 ml of saturated aqueous common salt solution and 300 ml of water four times and then dried over anhydrous sodium sulfate. The obtained product was concentrated with a rotary evaporator, and the residue was purified by the silica gel column chromatography to obtain 41.6 g (yield: 51%) of the intended compound (24).

Synthesis of Compound (25):

41.0 g of the compound (24), 40.0 ml of concentrated hydrochloric acid and 80 ml of methanol were fed into a three-necked flask. An aqueous solution of 13.8 g of sodium nitrite in 28 ml of water was dropped into the mixture under stirring under cooling with ice for a period of 15 minutes. Then the ice bath was removed and the stirring was continued for additional 5 hours. The reaction mixture was poured into 50 g of sodium hydrogencarbonate. 500 ml of ethyl acetate and 300 ml of water were added thereto to conduct the extraction. The ethyl acetate layer thus obtained was washed with a mixture of 50 ml of saturated aqueous common salt solution and 150 ml of water three times and then dried over anhydrous sodium sulfate. The obtained product was concentrated with a rotary evaporator, and the obtained residue was purified by the silica gel column chromatography to obtain 38.0 g (yield: 84%) of the intended compound (25) as an oily product.

Synthesis of Example Compound (A-32):

19.0 g of the compound (25), 0.5 g of palladium/carbon (10%) and 100 ml of methanol were fed into an autoclave, and they were stirred at room temperature under hydrogen pressure of 100 atm. for 3 hours. A solution of 21.6 g of naphthalene-1,5-disulfonate tetrahydrate in 45 ml of methanol was added to the obtained reaction mixture. After the filtration, the obtained filtrate was stirred and crystals thus formed were obtained by the filtration. 31.5 g (yield: 90%) of the intended example compound (A-32) was thus obtained.

NMR(D$_2$O): δ=8.86 (d, 2H, J=9.7 Hz), 8.21 (d, 2H, J=9.7 Hz), 7.72 (dd, 2H, J=9.7 Hz, 9.7 Hz), 7.45 (s, 1H), 7.24 (s, 1H), 3.2–4.0 (m, 14H), 2.8 to 3.1 (m, 1H), 2.36 (s, 3H), 1.8–2.3 (m, 2H), 1.50 (s, 3H), 1.10 (s, 3H).

SYNTHESIS EXAMPLE 4

The compound (A-52-a) of the present invention was synthesized according to the following reaction scheme:

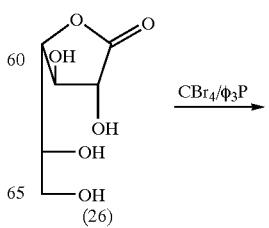

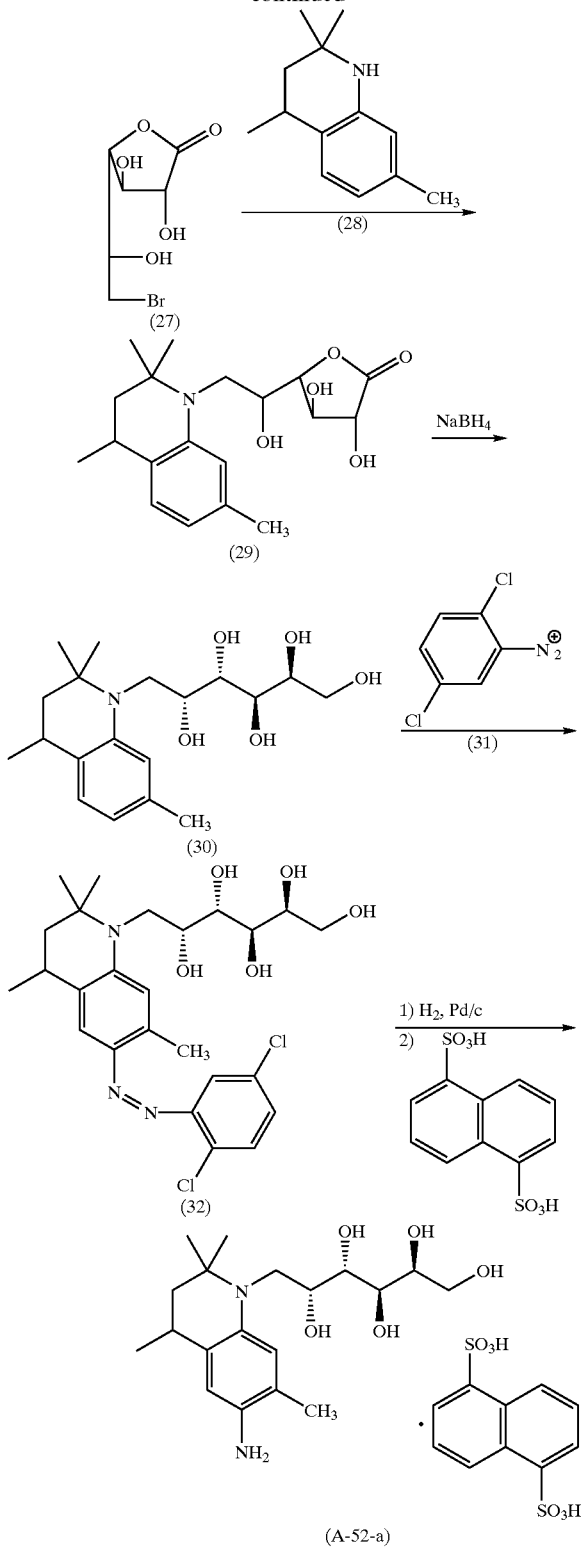

Synthesis of Compound (27):

25.0 g of γ-D-galactonolactone [compound (26)] and 500 ml of pyridine were fed into a three-necked flask. 73.5 g of triphenylphosphine was added thereto under stirring at room temperature and then 46.9 g of carbon tetrabromide was dropped thereinto for a period of 30 minutes. After the completion of the dropping, the resultant mixture was stirred at room temperature for 2 hours. 140 ml of methanol was dropped thereinto for a period of 10 minutes. The solvent was distilled off with an aspirator at an inner temperature of 60° C. or below under reduced pressure. 100 ml of water and 250 ml of toluene were added thereto to conduct the extraction. 50 ml of low-boiling components including water as the main component were distilled off from the obtained aqueous layer by means of an aspirator at an inner temperature of 60° C. or below under reduced pressure. The product was extracted by adding 100 ml of ethyl acetate to the residue eight times. The obtained ethyl acetate layer was dried over anhydrous sodium sulfate and left to stand overnight. The crystals thus formed were filtered to obtain 28.0 g (yield: 83%) of the intended compound (27).

Synthesis of Compound (29):

47.3 g of the compound (28), 22.5 g of sodium iodide, 63 g of sodium hydrogencarbonate and 140 ml of N,N-dimethylacetamide were fed into a three-necked flask. 72.3 g of the compound (27) was dropped into the resultant mixture under stirring under heating to an inner temperature of 90° C. for a period of 15 minutes. After the completion of the dropping, the stirring and heating were continued for 28 hours to keep the inner temperature at 90 to 95° C. and then cooled to 30° C. 1 l of ethyl acetate and 700 ml of water were added to the reaction mixture and the resultant mixture was stirred to conduct the extraction. The obtained ethyl acetate layer was washed with a mixture of 600 ml of water and 200 ml of saturated aqueous common salt solution four times and then dried over anhydrous sodium sulfate. The obtained product was concentrated with a rotary evaporator and then the residue was purified by silica gel column chromatography to obtain 65.0 g (yield: 75%) of the intended compound (29).

Synthesis of Compound (30):

26.0 g of of the compound (29) and 150 ml of methanol were fed into a three-necked flask. 5.7 g of sodium borohydride was slowly added thereinto under stirring and heating under reflux for a period of 5 minutes. After the completion of the addition, the resultant mixture was stirred under heating under reflux for 2 hours and then cooled to 30° C. The reaction mixture was concentrated under reduced pressure with an aspirator. A solution of 10 g of sodium hydroxide in 20 ml of water was added thereto and the resultant mixture was stirred, and then concentrated with an aspirator under reduced pressure. The residue was purified by silica gel column chromatography to obtain 20.0 g (yield: 76%) of the intended compound (30).

Synthesis of Compound (32):

15.7 g of 2,5-dichloroaniline and 90 ml of water were were fed into a three-necked flask. 31 ml of sulfuric acid was added thereto under stirring and under cooling with ice. A solution of 7.4 g of sodium nitrite in 20 ml of water was dropped into the resultant mixture for a period of 10 minutes while the inner temperature was kept at 8° C. or below. After the completion of the dropping, the stirring was continued for 30 minutes. 20.0 g of the compound (30), 55.4 g ml of sodium acetate, 38 ml of acetic acid and 75 ml of methanol were fed into another three-necked flask, and the diazonium salt solution prepared as described above was added thereto under stirring and under cooling with ice to keep the inner temperature at 16° C. or below. In this step, the reaction was traced by TLC, and the addition of the diazonium salt solution was completed when the compound (30) had disappeared from the reaction system. After the completion of the addition, the stirring was continued for additional 30 minutes. Methanol was distilled off under reduced pressure. The reaction mixture was poured onto ice, and neutralized with a sodium hydroxide solution. After the extraction with 1 l of ethyl acetate and 700 ml of water, the obtained ethyl acetate layer was washed with a mixture of 700 ml of water and 100 ml of saturated aqueous common salt solution four times and then dried over anhydrous sodium sulfate. The obtained product was concentrated with a rotary evaporator and then purified by silica gel column chromatography to obtain 20.0 g (yield: 67%) of the intended compound (32).

Synthesis of Example Compound (A-52-a):

20.0 g of the compound (32), 1 g of palladium/carbon (10%) and 80 ml of methanol were fed into an autoclave and stirred at room temperature under a hydrogen pressure of 100 atm. for 8 hours. A solution of 13.7 g of naphthalene-1,5-disulfonic acid in 25 ml of methanol was added to the reaction mixture. The obtained mixture was filtered, and the filtrate was concentrated with a rotary evaporator. 150 ml of ethyl acetate and 150 ml of water were added to the concentrate, and they were stirred to dissolve them and then they were separated to form layers. The aqueous layer thus obtained was washed with 150 ml of ethyl acetate three times. The aqueous layer thus obtained was concentrated with a rotary evaporator, and then the concentrate was dissolved in 50 ml of methanol. The crystals thus formed were filtered by suction to obtain 22.0 g of the intended example compound (A-52-a) (yield: 88%).

SYNTHESIS EXAMPLE 5

The compound (A$_2$-17) was synthesized according to the following reaction scheme:

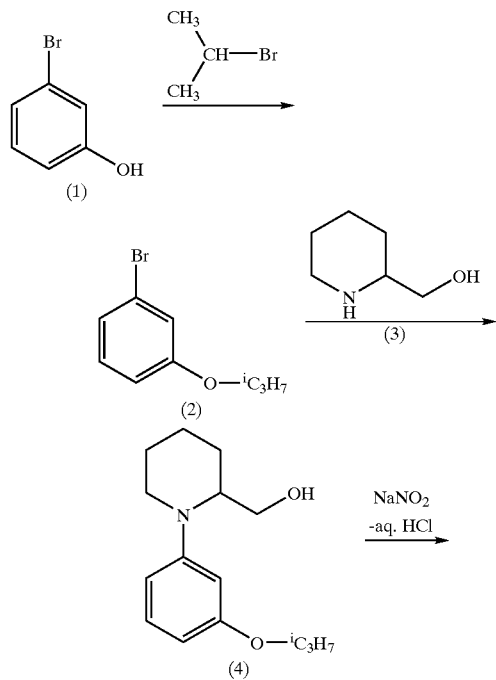

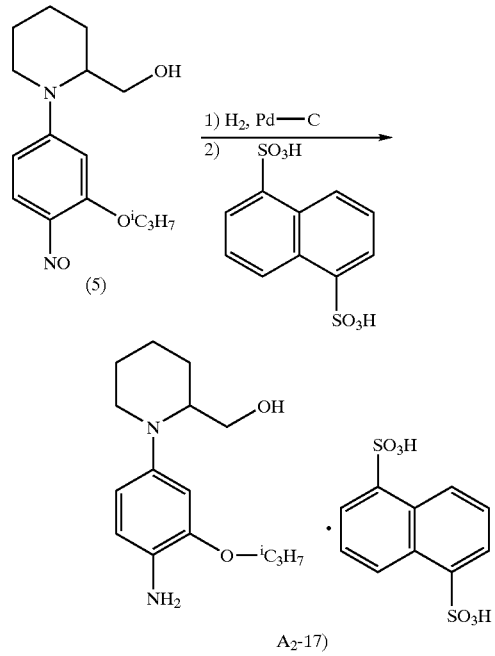

Synthesis of Compound (2):
173.0 g of the compound (1), 276 g of potassium carbonate and 350 ml of N,N-dimethylacetamide were fed into a three-necked flask. 148 g of 2-bromopropane was dropped into the resultant mixture under heating and stirring at an inner temperature of 85° C. for a period of 20 minutes. After the completion of the dropping, the stirring and heating were continued for 3 hours and then the inner temperature was lowered to 30° C. 800 ml of ethyl acetate and 800 ml of water were added to the reaction mixture to conduct the extraction. The obtained ethyl acetate layer was washed with a mixture of 500 ml of saturated aqueous common salt solution and 500 ml of water four times and then the ethyl acetate layer thus obtained was dried over anhydrous sodium sulfate. The obtained product was concentrated with a rotary evaporator and then the residue was purified by silica gel column chromatography to obtain 215 g (yield: 100%) of the intended compound (2).

Synthesis of Compound (4):
72.6 g of of the compound (2), 250 g of the compound (3) and 19.0 g of copper (I) iodide were fed into a three-necked flask, and the resultant mixture was stirred under heating to keep the inner temperature at 130° C. for 1 hour and then cooled to 30 C. 1000 ml of ethyl acetate and 800 ml of water were added to the reaction mixture to conduct the extraction. The obtained ethyl acetate layer was washed with a mixture of 100 ml of saturated aqueous common salt solution and 500 ml of water five times and then the ethyl acetate layer thus obtained was dried over anhydrous sodium sulfate. The obtained product was concentrated with a rotary evaporator and then the residue was purified by silica gel column chromatography to obtain 59.0 g (yield: 70%) of the intended compound (4).

Synthesis of Compound (5):
23.0 g of the compound (4), 26.0 g of hydrochloric acid and 250 ml of methanol were fed into a three-necked flask. A solution of 10.2 g of sodium nitride in 20 ml of water was dropped into the resultant mixture for a period of 30 minutes while the inner temperature was kept at 10° C. or below. After the completion of the dropping, the stirring was continued for 3 hours while the inner temperature was kept at 10° C. or below. Methanol was distilled off with an aspirator under a reduced pressure. 300 ml of ethyl acetate and 100 ml of water were added to the residue and then the resultant mixture was neutralized with 40 g of sodium hydrogencarbonate. After the separation into layers, the ethyl acetate layer was washed with a mixture of 50 ml of saturated aqueous common salt solution and 100 ml of water four times and then dried over anhydrous sodium sulfate. The obtained product was concentrated with a rotary evaporator to obtain the intended compound (5) as the crude product, which was directly subjected to the subsequent step.

Synthesis of Example Compound ($A_2$-17):

The compound (5) obtained as described above, 100 ml of ethanol and 5 g of palladium/carbon (10%) were fed into an autoclave and stirred at room temperature under a hydrogen pressure of 100 atm. for 5 hours. A solution of 33.1 g of naphthalene-1,5-disulfonic acid tetrahydrate in 66 ml of methanol was added to the reaction mixture. The obtained mixture was filtered, and the crystals formed from the filtrate were taken by the filtration to obtain 43.2 g of the intended example compound ($A_2$-17) (yield: 85%).

SYNTHESIS EXAMPLE 6

The compound ($A_2$-27) was synthesized according to the following reaction scheme:

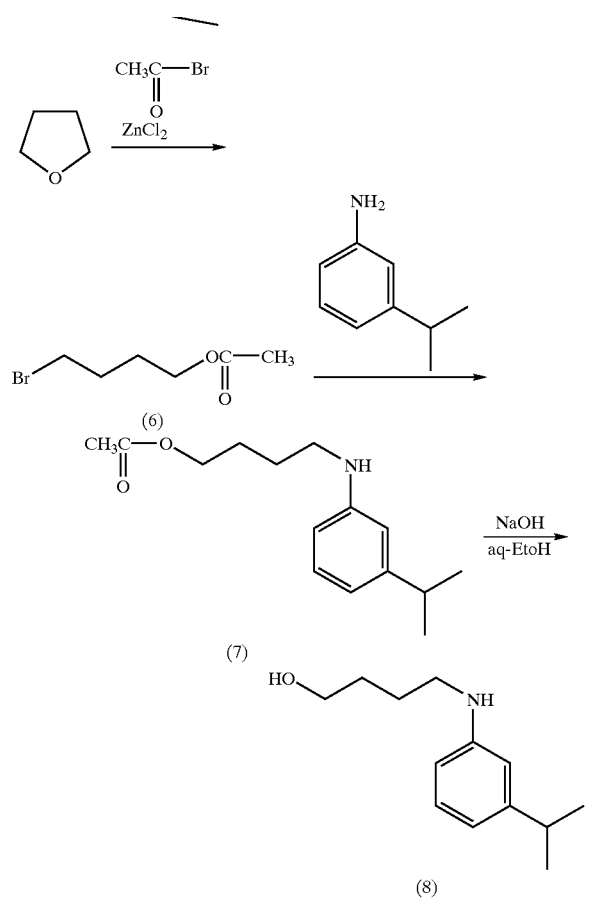

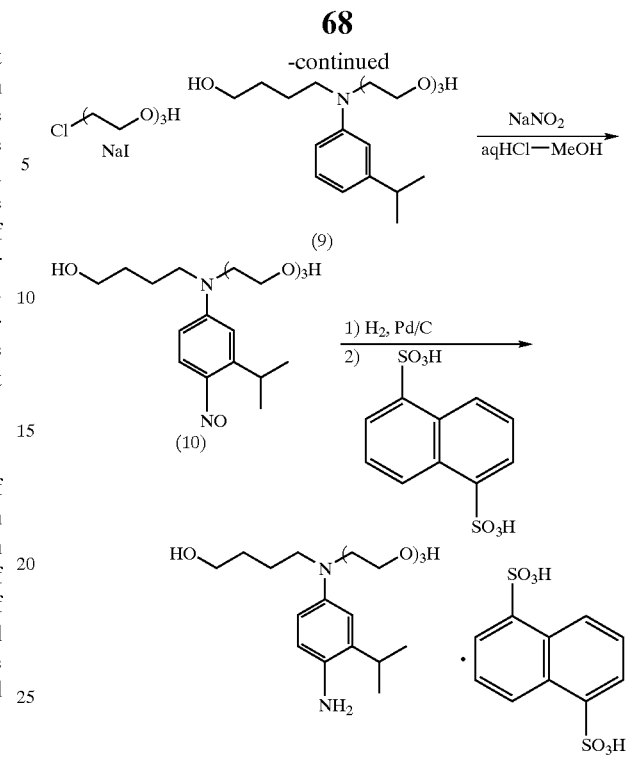

Example Compound ($A_2$-27)

Synthesis of Compound (6):

441 g of tetrahydrofuran and 0.30 g of zinc chloride were fed into a three-necked flask. 500 g of acetyl bromide was dropped thereinto under stirring at room temperature for a period of 1.5 hours. The temperature in the flask was elevated from 18° C. to 60° C. After the completion of the dropping, the stirring was continued under heating at an inner temperature of 87° C. for 1.5 hour. After lowering the inner temperature to 25° C., 1.5 l of ethyl acetate and 2 l of water were added thereto and the resultant mixture was neutralized with sodium hydrogencarbonate under stirring. After the extraction, the obtained ethyl acetate layer was dried over anhydrous sodium sulfate. The obtained product was concentrated and distilled to collect a fraction of 120 to 122° C./35 mmHg to obtain 760 g (yield: 96%) of the intended compound (6).

Synthesis of Example Compound (7):

40.5 g of m-isopropylaniline, 50.4 g of sodium hydrogencarbonate and 150 ml of N,N-dimethylacetamide were fed into a three-necked flask. 64.3 g of the compound (6) was dropped thereinto under stirring and heating to an inner temperature of 130° C. for a period of 2 hours, and the resultant mixture was stirred under heating to an inner temperature of 130° C. for 8 hours. After cooling to an inner temperature of 25° C., the product was extracted with 600 ml of ethyl acetate and 500 ml of water, the obtained ethyl acetate layer was washed with a mixture of 500 ml of water and 100 ml of saturated aqueous common salt solution four times. The obtained ethyl acetate layer was dried over anhydrous sodium sulfate and the product was concentrated with a rotary evaporator. The residue was purified by the column chromatography to obtain 30.6 g (yield: 41%) of the intended compound (7).

Synthesis of Compound (8):

30.6 g of the compound (7) and 150 ml of ethanol were fed into a three-necked flask. An aqueous solution of 19.7 g of sodium hydroxide in 40 ml of water was added to the resultant mixture, and they were directly stirred for 2 hours.

400 ml of ethyl acetate and 500 ml of water were added thereto, and the ethyl acetate layer obtained by the extraction was washed with a mixture of 300 ml of water and 100 ml of saturated aqueous common salt solution four times. The obtained ethyl acetate layer was dried over anhydrous sodium sulfate and the product was concentrated with a rotary evaporator. The residue was purified by the column chromatography to obtain 22.7 g (yield: 89%) of the intended compound (8).

Synthesis of Example Compound (9):

22.7 g of the compound (8), 18.3 g of sodium hydrogencarbonate and 70 ml of N,N-dimethylacetamide were fed into a three-necked flask. 23.9 g of 2-[2-(2-chloroethoxy)ethoxy]ethanol was dropped thereinto under heating and stirring at an inner temperature of 130° C. for a period of 10 minutes, and the resultant mixture was stirred under heating to an inner temperature of 130° C. for four hours. After cooling to an inner temperature of 25° C., the product was extracted with 500 ml of ethyl acetate and 400 ml of water, and the obtained ethyl acetate layer was washed with a mixture of 300 ml of water and 100 ml of saturated aqueous common salt solution four times and then dried over anhydrous sodium sulfate. The obtained product was concentrated with a rotary evaporator, and the residue was purified by the column chromatography to obtain 24.3 g (yield: 66%) of the intended compound (9).

Synthesis of Compound (10):

24.3 g of the compound (9), 200 ml of methanol and 20.3 ml of hydrochloric acid were fed into a three-necked flask. An aqueous solution of 5.7 g of sodium nitrite in 15 ml of water was dropped into the mixture under stirring under cooling with ice for a period of 10 minutes. The inner temperature was 7 to 8° C. in this stage. After the completion of the dropping, the stirring was continued for additional 8 hours. 40 g of sodium hydrogencarbonate was added and the resultant mixture was stirred and filtered by suction. The filtrate was concentrated with a rotary evaporator, and the obtained residue was purified by the column chromatography to obtain 19.5 g (yield: 74%) of the intended compound (10).

Synthesis of Example Compound (A$_2$-27):

19.5 g of the compound (10), 100 ml of ethanol and 3 g of palladium/carbon catalyst (10%) were fed into an autoclave, and they were stirred at room temperature under hydrogen pressure of 100 atm. for 5 hour s. The obtained reaction mixture was filtered, and a solution of 19.1 g of naphthalene-1,5-disulfonate hetrahydrate in 40 ml of methanol was added to the filtrate. The obtained mixture was stirred and then the solvent was distilled off to obtain 33.3 g (yield: 98%) of the intended example compound (Az-27).

SYNTHESIS EXAMPLE 7

The example compound (A$_2$-39) of the present invention was synthesized according to the following reaction scheme:

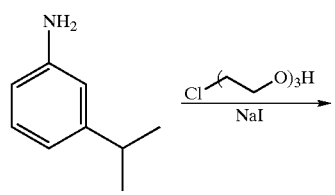

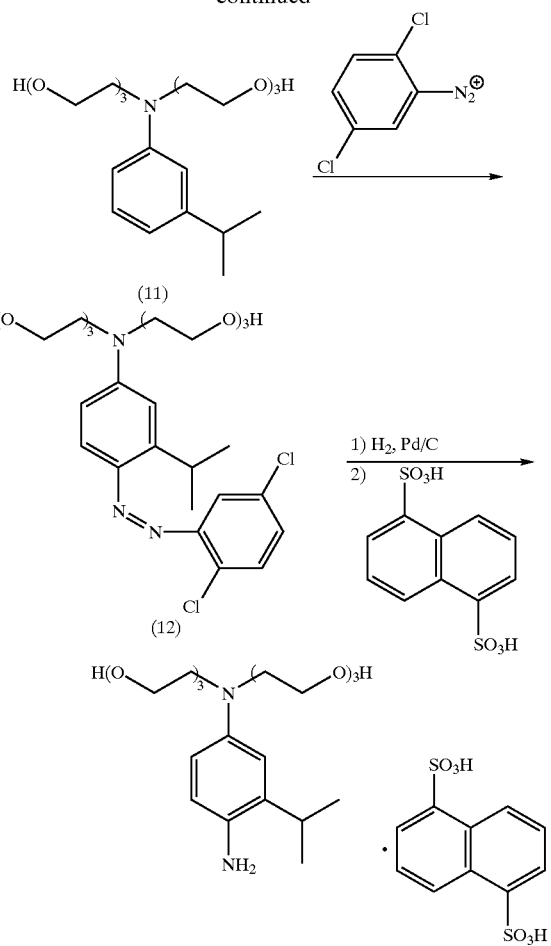

Example Compound (A$_2$-39)

Synthesis of Example Compound (11):

40.6 g of m-isopropylaniline, 202 g of sodium hydrogencarbonate, 45 g of sodium iodide and 300 ml of N,N-dimethylacetamide were fed into a three-necked flask. 202 g of 2-[2-(2-chloroethoxy)ethoxy]ethanol was dropped thereinto under heating and stirring at an inner temperature of 130° C. for a period of 30 minutes. The resultant mixture was stirred under heating to an inner temperature of 130° C. for additional 8 hours. After cooling to an inner temperature of 25° C., the product was extracted with 800 ml of ethyl acetate and 800 ml of water, and the obtained ethyl acetate layer was washed with a mixture of 700 ml of water and 100 ml of saturated aqueous common salt solution four times. The ethyl acetate layer thus obtained was dried over anhydrous sodium sulfate. The obtained product was concentrated with a rotary evaporator, and the residue was purified by the column chromatography to obtain 64.7 g (yield: 54%) of the intended compound (11).

Synthesis of Compound (12) 39.4 g of 2,5-dichloroaniline and 500 ml of water were fed into a three-necked flask. 82 ml of sulfuric acid was added thereto under stirring and under cooling with ice. A solution of 18.4 g of sodium nitrite in 40 ml of water was dropped into the resultant mixture for a period of 10 minutes while the inner temperature was kept at 8° C. or below. After the completion of the dropping, the stirring was continued for 30 minutes. 64.7 g of the compound (11), 133 g of sodium acetate, 97 ml of acetic acid and 500 ml of methanol were fed into another three-necked flask, and the diazonium salt solution prepared as described above was added thereto under stirring and under cooling with ice to keep the inner temperature at 17° C. or below. In this step, the reaction was traced by TLC, and the addition of the diazonium salt solution was completed when the compound (11) had disappeared from the reaction system. After the completion of the addition, the stirring was continued for additional 30 minutes. Methanol was distilled off under reduced pressure. The reaction mixture was poured in water, and neutralized with an aqueous sodium hydroxide solution. After the extraction with 1.5% of ethyl acetate and 500 ml of water, the obtained ethyl acetate layer was washed with a mixture of 700 ml of water and 200 ml of saturated aqueous common salt solution four times and then dried over anhydrous sodium sulfate. The obtained product was concentrated with a rotary evaporator and then the obtained residue was purified by silica gel column chromatography to obtain 5 3.8 g (yield: 58%) of the intended compound (12).

Synthesis of Example Compound ($A_2$-39):

53.8 g of the compound (12), 5 g of palladium/carbon (10%) and 200 ml of ethanol were fed into an autoclave and stirred at room temperature under a hydrogen pressure of 100 atm. for 5 hours. A solution of 33.8 g of naphthalene-1,5-disulfonic acid tetrahydrate in 65 ml of methanol was added to the reaction mixture. After the filtration, the filtrate was concentrated with a rotary evaporator. 400 ml of ethyl acetate and 400 ml of water were added to the concentrate, and they were stirred to dissolve them and then they were separated into layers. The aqueous layer thus obtained was washed with 400 ml of ethyl acetate three times. The aqueous layer thus obtained was concentrated with a rotary evaporator, and then crystals formed from a solution thereof in a mixture of methanol and ethanol were taken by the filtration to obtain 42.9 g of the intended example compound ($A_2$-39) (yield: 65%).

SYNTHESIS EXAMPLE 8

The example compound ($A_2$-40) of the present invention was synthesized according to the following reaction scheme:

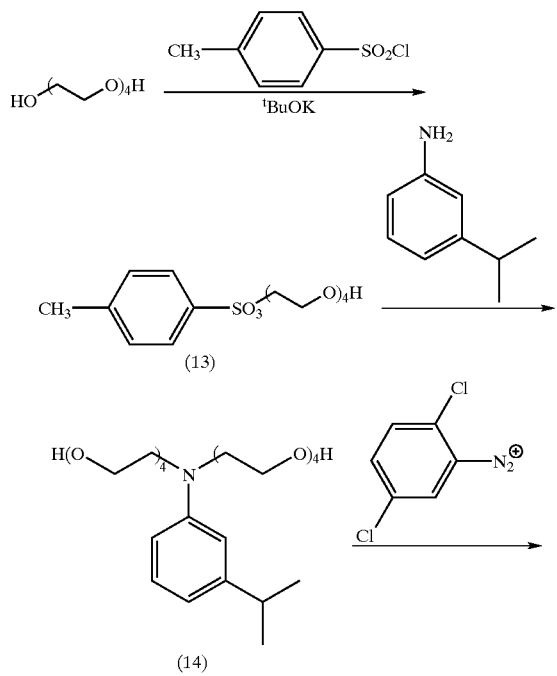

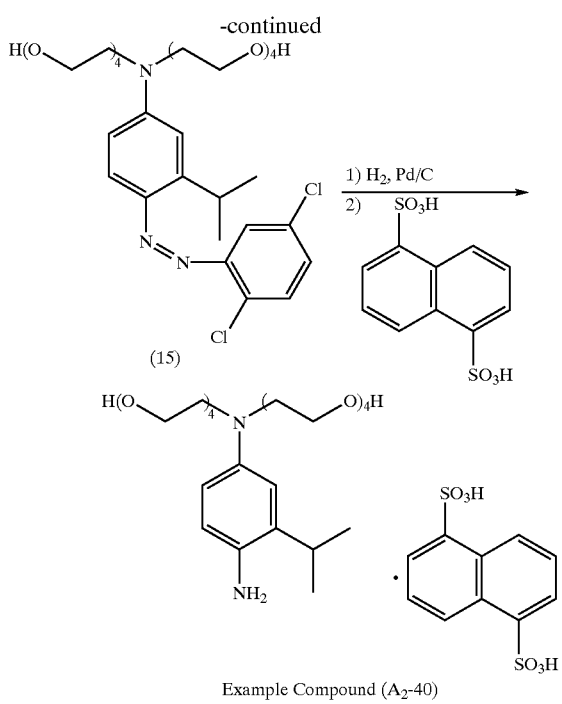

Example Compound ($A_2$-40)

Synthesis of Compound (13):

1100 g of tetraethylene glycol and 1.5 l of tetrahydrofuran were fed into a three-necked flask. 68.3 g of potassium t-butoxide was added thereto under stirring under cooling with ice. The temperature in the flask was elevated to 40° C. The stirring was continued for 30 minutes and then 285.8 g of p-toluenesulfonyl chloride was added thereto while the inner temperature was kept at 15° C. or below. After continuing the stirring for one hour, the ice bath was removed and the stirring was continued at room temperature for 3 hour. Tetrahydrofuran was distilled off under reduced pressure. 1.5 l of ethyl acetate and 2 l of water were added to the residue to conduct the extraction. The obtained ethyl acetate layer was washed with a mixture of 1 l of water and 0.4 l of saturated aqueous common salt solution six times and then dried over anhydrous sodium sulfate. The obtained product was concentrated with a rotary evaporator and then the obtained residue was purified by silica gel column chromatography to obtain 243.7 g (yield: 47%) of the intended compound (13).

Synthesis of Example Compound (14):

40.6 g of m-isopropylaniline, 202 g of sodium hydrogencarbonate, 45 g of sodium iodide and 300 ml of N,N-dimethylacetamide were fed into a three-necked flask. 376.3 g of the compound (13) was dropped thereinto under stirring and heating to an inner temperature of 130° C. for a period of 2 hours, and the resultant mixture was stirred under heating to an inner temperature of 130° C. for 12 hours. After cooling to an inner temperature of 25° C., the product was extracted with 1.2 l of ethyl acetate and 1.2 l of water, the obtained ethyl acetate layer was washed with a mixture of 900 ml of water and 100 ml of saturated aqueous common salt solution four times. The obtained ethyl acetate layer was dried over anhydrous sodium sulfate and the product was concentrated with a rotary evaporator. The residue was purified by the column chromatography to obtain 70.2 g (yield: 48%) of the intended compound (14).

Synthesis of Compound (15):

35.0 g of 2,5-dichloroaniline and 500 ml of water were fed into a three-necked flask. 73 ml of sulfuric acid was added thereto under stirring and under cooling with ice. A solution of 16.3 g of sodium nitrite in 40 ml of water was dropped into the resultant mixture for a period of 10 minutes while the inner temperature was kept at 8° C. or below. After the completion of the dropping, the stirring was continued for 30 minutes. 70.2 g of the compound (14), 118 g of sodium acetate, 86 ml of acetic acid and 500 ml of methanol were fed into another three-necked flask, and the diazonium salt solution prepared as described above was added thereto under stirring and under cooling with ice to keep the inner temperature at 17° C. or below. In this step, the reaction was traced by TLC, and the addition of the diazonium salt solution was completed when the compound (14) had disappeared from the reaction system. After the completion of the addition, the stirring was continued for additional 30 minutes. Methanol was distilled off under reduced pressure. The reaction mixture was poured in water, and neutralized with an aqueous sodium hydroxide solution. After the extraction with 1.5 l of ethyl acetate and 500 ml of water, the obtained ethyl acetate layer was washed with a mixture of 700 ml of water and 200 ml of saturated aqueous common salt solution four times and then dried over anhydrous sodium sulfate. The obtained product was concentrated with a rotary evaporator and then the obtained residue was purified by silica gel column chromatography to obtain 66.6 g (yield: 70%) of the intended compound (15).

Synthesis of Example Compound ($A_2$-40):

66.6 g of the compound (15), 7 g of palladium/carbon (10%) and 200 ml of ethanol were fed into an autoclave and stirred at room temperature under a hydrogen pressure of 100 atm. for 5 hours. A solution of 36.4 g of naphthalene-1,5-disulfonic acid tetrahydrate in 70 ml of methanol was added to the reaction mixture. After the filtration, the filtrate was concentrated with a rotary evaporator. 400 ml of ethyl acetate and 400 ml of water were added to the concentrate, and they were stirred to obtain a solution. Then the solution was divided to form layers. The aqueous layer thus obtained was washed with 400 ml of ethyl acetate three times. Water was distilled off under reduced pressure from the aqueous layer thus obtained to obtain 76.7 g of the intended example compound ($A_2$-40) (yield: 96%).

SYNTHESIS EXAMPLE 9

The example compound ($A_4$-4) was synthesized according to the following reaction scheme:

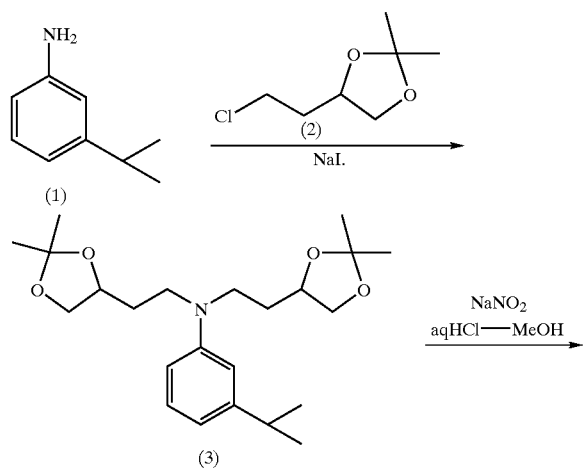

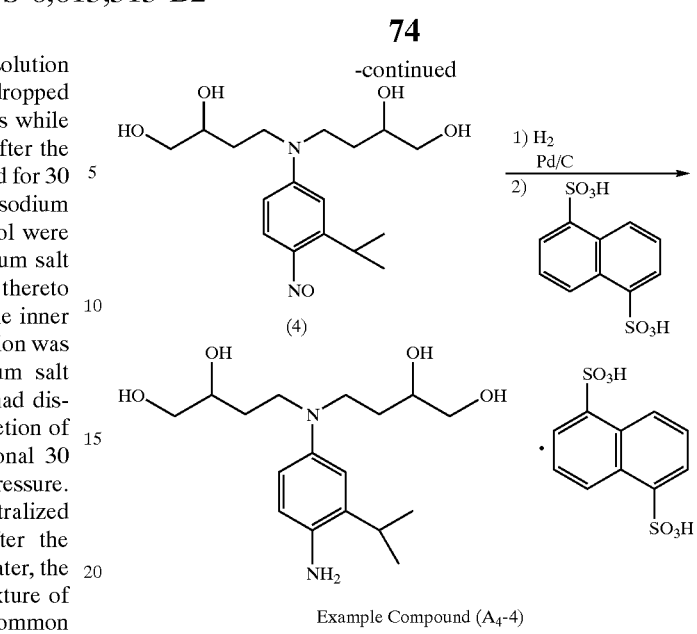

Example Compound ($A_4$-4)

Synthesis of Example Compound (3):

40.6 g of the compound (1), 98.4 g of sodium hydrogencarbonate, 45.0 g of sodium iodide and 200 ml of N,N-dimethylacetamide were fed into a three-necked flask. 128.4 g of the compound (2) was dropped thereinto under heating and stirring at an inner temperature of 130° C. for a period of 30 minutes. The resultant mixture was stirred under heating to keep the inner temperature at 130° C. for additional 4 hours. After cooling to an inner temperature of 25° C., the product was extracted with 700 ml of ethyl acetate and 500 ml of water, and the obtained ethyl acetate layer was washed with a mixture of 500 ml of water and 100 ml of saturated aqueous common salt solution five times. The ethyl acetate layer thus obtained was dried over anhydrous sodium sulfate and then concentrated with a rotary evaporator, and the residue was purified by the column chromatography to obtain 77.4 g (yield: 66%) of the intended compound (3).

Synthesis of Compound (4):

77.4 g of the compound (3), 400 m of methanol and 56 ml of hydrochloric acid were fed into a three-necked flask. An aqueous solution of 15.7 g of sodium nitrite in 30 ml of water was dropped into the mixture under stirring under cooling with ice for a period of 10 minutes. The inner temperature was 8 to 9° C. in this stage. After the completion of the dropping, the stirring was continued for additional 6 hours. 84 g of sodium hydrogencarbonate was added and the resultant mixture was stirred and filtered by suction. The filtrate was concentrated with a rotary evaporator, and the obtained residue was purified by the column chromatography to obtain 53.2 g (yield: 80%) of the intended compound (4).

Synthesis of Example Compound ($A_4$-4):

53.2 g of the compound (4), 300 ml of ethanol and 6 g of palladium/carbon catalyst (10%) were fed into an autoclave, and they were stirred at room temperature under hydrogen pressure of 100 atm. for 5 hours. The obtained reaction mixture was filtered, and a solution of 56.9 g of naphthalene-1,5-disulfonic acid hetrahydrate in 100 ml of methanol was added to the filtrate. The obtained mixture was stirred and then the solvent was distilled off to obtain 93.1 g (yield: 96%) of the intended example compound ($A_4$-4).

SYNTHESIS EXAMPLE 10

The example compound (A$_4$-41-a) of the present invention was synthesized according to the following reaction scheme:

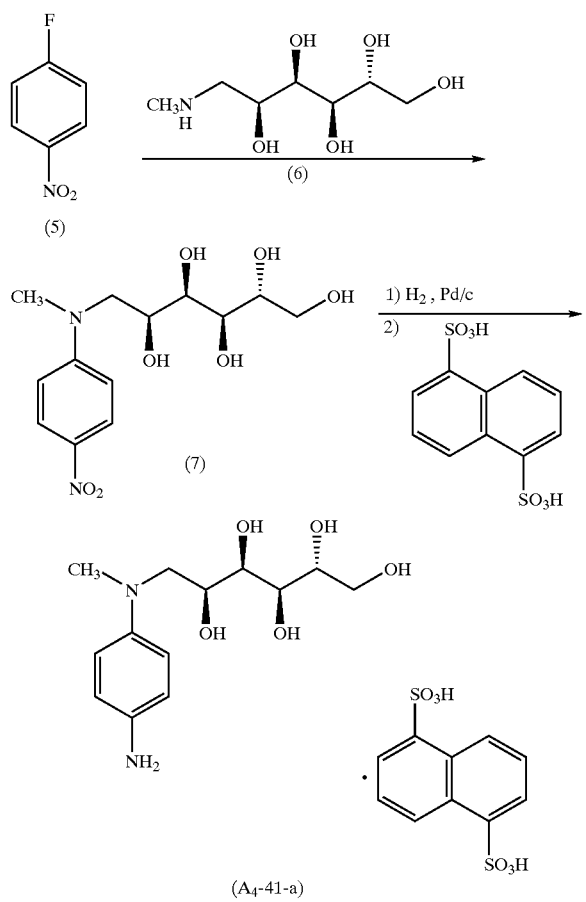

(A$_4$-41-a)

Synthesis of Compound (7):

42.3 g of the compound (5), 70.3 g of N-methyl-D-glucamine [the compound (6)], 200 ml of acetonitrile and 50 ml of water were fed into a three-necked flask. 50.2 ml of triethylamine was dropped thereinto under stirring and heating under reflux for a period of 10 minutes. After the completion of the dropping, the stirring was continued under heating under reflux for 8 hours. After cooling to 70° C., the product was extracted with 100 ml of water, 150 ml of ethyl acetate and 200 ml of hexane, and the obtained aqueous layer was washed with a mixture of 150 ml of ethyl acetate and 150 ml of hexane three times. The temperature was always kept at 50° C. or higher in the course of the extraction and washing. 300 ml of water was added to the aqueous solution thus obtained, and the resultant mixture was stirred under cooling with water. The crystals thus formed was taken by the filtration by suction and then dried to obtain 73.1 g (yield: 77%) of the intended compound (7).

Synthesis of Example Compound (A$_4$-41-a):

73.1 g of the compound (7), 7 g of palladium/carbon (10%) and 220 ml of methanol were fed into an autoclave, and they were stirred at room temperature under hydrogen pressure of 100 atm. for 8 hours. A solution of 83.2 g of naphthalene-1,5-disulfonic acid tetrahydrate in 200 ml of methanol was added to the reaction mixture. The obtained mixture was filtered, and the filtrate was concentrated with a rotary evaporator and then the solvent was distilled off with a vacuum pump under reduced pressure to obtain 127 g (yield: 96%) of the intended example compound (A$_4$-41-a).

SYNTHESIS EXAMPLE 11

The example compound (A$_4$-34-a) of the present invention was synthesized according to the following reaction scheme:

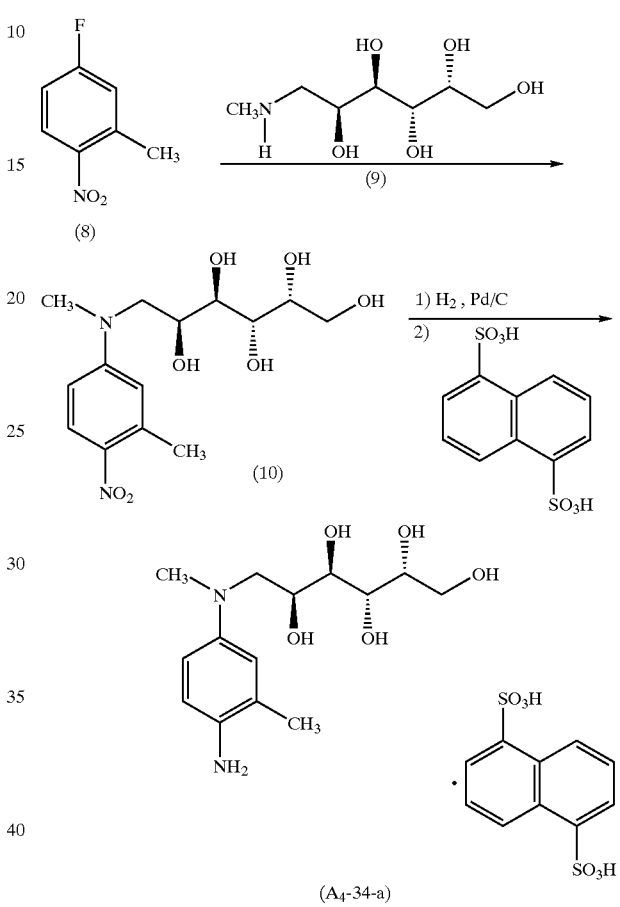

(A$_4$-34-a)

Synthesis of Compound (10):

39.4 g of the compound (8), 59.6 g of 1-deoxy-1-(methylamino)-D-galactitol [the compound (9)], 140 ml of acetonitrile and 40 ml of water were fed into a three-necked flask. 42.5 ml of triethylamine was dropped thereinto under stirring and heating under reflux for a period of 10 minutes. After the completion of the dropping, the stirring was continued under heating under reflux for 8 hours. After cooling to 70° C., the product was extracted with 50 ml of water, 100 ml of ethyl acetate and 100 ml of hexane, and the obtained aqueous layer was washed with a mixture of 150 ml of ethyl acetate and 150 ml of hexane three times. The temperature was always kept at 50° C. or higher in the course of the extraction and washing. 300 ml of water was added to the aqueous solution thus obtained, and the resultant mixture was stirred under cooling with water. The crystals thus formed was taken by the filtration by suction and then dried to obtain 58.7 g (yield: 70%) of the intended compound (10).

Synthesis of Example Compound (A$_4$-34-a):

58.7 g of the compound (10), 5 g of palladium/carbon (10%) and 150 ml of methanol were fed into an autoclave, and they were stirred at room temperature under hydrogen pressure of 100 atm. for 8 hours. A solution of 63.9 g of naphthalene-1,5-disulfonic acid tetrahydrate in 100 ml of methanol was added to the reaction mixture. The obtained mixture was filtered, and the filtrate was concentrated with a rotary evaporator and then the solvent was distilled off with a vacuum pump under reduced pressure to obtain 105 g (yield: 100%) of the intended example compound ($A_4$-34-a).

SYNTHESIS EXAMPLE 12

The example compound ($A_4$-31-a) of the present invention was synthesized according to the following reaction scheme:

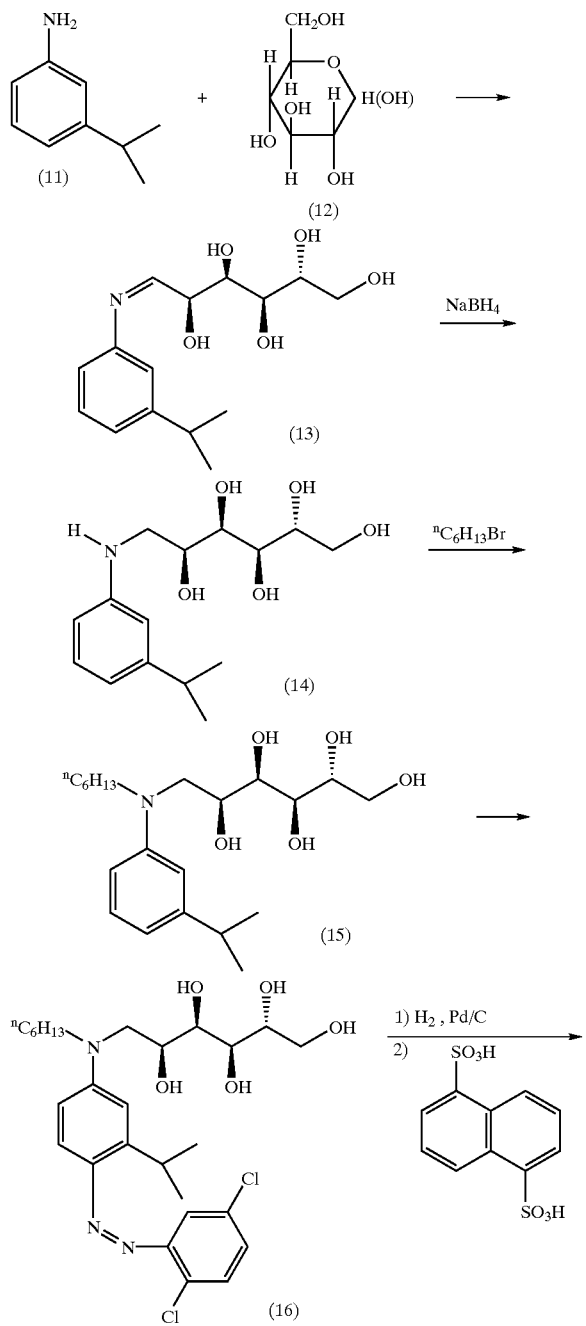

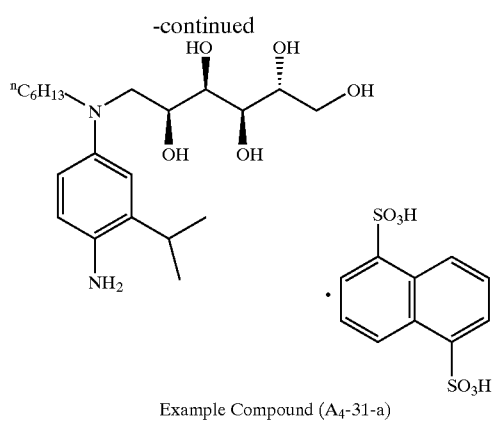

Example Compound ($A_4$-31-a)

Synthesis of Example Compound (13):
 81.2 g of the compound (11), D-glucose [the compound (12)] and 1.2 l of methanol were fed into a three-necked flask. After stirring under heating under reflux for 5 hours, the solvent was distilled off and the product was extracted with 0.8 l of water and 0.7 l of hexane. 1 l of ethyl acetate was added to the obtained aqueous layer. The ethyl acetate layer thus obtained was dried over anhydrous sodium sulfate and concentrated with a rotary evaporator to obtain 110 g (yield: 62%) of the intended compound (13) as the crude product, which was directly subjected to the subsequent step.
Synthesis of Compound (14):
 100 g of of the compound (13) and 700 ml of methanol were fed into a three-necked flask. 25.4 g of sodium borohydride was added thereinto under cooling with water (the inner temperature was elevated to 42° C.). After stirring under these conditions for 2 hours, the resultant mixture was stirred under heating under reflux for 2 hours. The solvent was distilled off, and the product was extracted with a solution of 50 g of sodium hydroxide in 500 ml of water and 700 ml of ethyl acetate, and the obtained ethyl acetate layer was washed with a mixture of 500 ml of water and 100 ml of saturated aqueous common salt solution three times and then dried over anhydrous sodium sulfate. The dry product was concentrated with a rotary evaporator. 300 ml of hexane was added to the residue and the resultant mixture was stirred. Crystals thus formed were taken by the filtration to obtain 70.0 g (yield: 70%) of the intended compound (14).
Synthesis of Compound (15):
 24 g of of the compound (14), 20.0 g of sodium hydrogencarbonat e, 7.2 g of sodium iodide and 72 ml of N,N-dimethylacetamide were fed into a three-necked flask. 15.8 g of hexyl bromide was dropped therein under stirring and heating at an inner temperature of 100° C. for a period of 10 minutes. The resultant mixture was stirred under heating at an inner temperature of 100° C. After cooling the mixture to an inner temperature of 25° C., 300 ml of ethyl acetate and 200 ml of water were added thereto to conduct the extraction. The obtained ethyl acetate layer was washed with a mixture of 200 ml of water and 50 ml of saturated aqueous common salt solution four times and then dried over anhydrous sodium sulfate. The dry product was concentrated with a rotary evaporator. The residue was purified by silica gel column chromatography to obtain 18.0 g (yield: 60%) of the intended compound (15).
Synthesis of Compound (16):
 10.0 g of 2,5-dichloroaniline and 60 ml of water were were fed into a three-necked flask. 20.0 ml of sulfuric acid was added thereto under stirring and under cooling with ice.

A solution of 4.7 g of sodium nitrite in 10 ml of water was dropped into the resultant mixture for a period of 10 minutes while the inner temperature was kept at 8° C. or below. After the completion of the dropping, the stirring was continued for 30 minutes. 14.0 g of the compound (15), 36.1 g of sodium acetate, 25 ml of acetic acid and 50 ml of methanol were fed into another three-necked flask, and the diazonium salt solution prepared as described above was added thereto under stirring and under cooling with ice while the inner temperature was kept at 18° C. or below. In this step, the reaction was traced by TLC, and the addition of the diazonium salt solution was completed when the compound (15) had disappeared from the reaction system. After the completion of the addition, the stirring was continued for additional 30 minutes. 700 ml of water and 1 l of ethyl acetate were added thereto, and the resultant mixture was stirred. After the neutralization with sodium hydrogencarbonate followed by the extraction, the obtained ethyl acetate layer was washed with a mixture of 600 ml of water and 100 ml of saturated aqueous common salt solution and then dried over anhydrous sodium sulfate. The obtained product was concentrated with a rotary evaporator and then purified by silica gel column chromatography to obtain 15.8 g (yield: 78%) of the intended compound (16).

Synthesis of Example Compound ($A_4$-31-a):

10.0 g of the compound (16), 2 g of palladium/carbon (10%) and 100 ml of methanol were fed into an autoclave and stirred at room temperature under a hydrogen pressure of 100 atm. for 5 hours. A solution of 6.5 g of naphthalene-1,5-disulfonic acid tetrahydrate in 15 ml of methanol was added to the reaction mixture. The obtained mixture was filtered, and the filtrate was concentrated with a rotary evaporator. 200 ml of ethyl acetate and 200 ml of water were added to the concentrate, and they were stirred to obtain a solution. Then the solution was divided to form layers. The aqueous layer thus obtained was further washed with 200 ml of ethyl acetate three times. The solvent was distilled off from the aqueous layer thus obtained to obtain 12.0 g (yield: 97%) of the intended example compound ($A_4$-31-a).

The compounds of the general formulae (I) to (V) are incorporated each preferably in an amount of 0.001 to 40% by weight, more preferably 0.01 to 30% by weight, based on the whole hair dye composition.

The compounds of the general formulae (I) to (V) are preferably used in a hair-dyeing method wherein each of them penetrates into hair together with a phenol compound called "coupler" to form a coloring matter in the presence of an oxidizing agent to dye the hair.

The oxidizing agents are, for example, sodium percarbonate, potassium percarbonate, sodium perborate, potassium perborate, sodium peroxide, potassium peroxide, magnesium peroxide, barium peroxide, calcium peroxide, strontium peroxide, hydrogen peroxide adducts of sulfuric acid salts, hydrogen peroxide adducts of phosphoric acid salts, hydrogen peroxide adducts of pyrophosphoric acid salts, urea peroxide and melamine peroxide. Among them, sodium percarbonate, potassium percarbonate, sodium perborate and potassium perborate are preferred.

Various color tones and a further improved hair-dyeing effect can be obtained by adding one or more compounds usually incorporated as dyes into a composition for dyeing keratin fibers, particularly hair, such as p-phenylenediamine, p-toluenediamine, 2-chloro-p-phenylenediamine, p-aminophenol, p-methylaminophenyl, resorcinol, m-phenylenediamine, 5-amino-2-methylphenol, 4-nitro-o-phenylenediamine, 2-nitro-p-phenylenediamine, picramic acid and salts of them. These dyes are used in an amount of 0.001 to 30% by weight. From the viewpoint of the hair-dyeing effect, the amount is preferably 0.01 to 20% by weight.

The hair dye compositions can contain 2,4-diaminophenetol, 1-methoxy-2-amino-4-(2-hydroxyethyl)aminobenzene, salts of them and dyes described in "Standards for raw materials for Quasi-drugs" (published by Yakuji Nippo-sha (Pharmaceutical News Co.) in June, 1991) in addition to the above-described dyes.

The hair dye composition of the present invention can contain other ingredients usually used for hair dyes so far as the effect of the present invention is not impaired.

For example, oily ingredients include natural oils and fats, higher fatty acids, sterols, ester oils, hydrocarbon oils and higher alcohols. Preferred oily ingredients are natural oils and fats, higher fatty acids, sterols and ester oils. The natural oils and fats are, for example, liquid oils and fats such as avocado oil, camellia oil, macadamia nut oil, corn oil, mink oil, olive oil, rapeseed oil, yolk oil, sesame oil, wheat germ oil, castor oil, linseed oil, safflower oil, cotton seed oil, soybean oil, peanut oil, tea seed oil, rice bran oil, jovova oil, germ oil, triglycerol, glycerol trioctanoate and glycerol triisopalmitate.

The higher fatty acids are, for example, lauric acid, myristic acid, palmitic acid, stearic acid, behenic acid, oleic acid, 12-hydroxystearic acid, undecylenic acid, tallic acid, isostearic acid, linoleic acid, linolenic acid, eicosapentaenoic acid (EPA) and docosahexanoic acid (DHA). The sterols are, for example, cholesterol and phytosterol.

The ester oils are, for example, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid esters, N-alkyl glycol monoisostearate, neopentyl glycol dicaprate, diisostearyl malate, glycerol di-2-heptylundecanoate, trimethylolpropane tri-2-ethylhexylate, trimethylolpropane triisostearate, pentaerythritol tetra-2-ethylhexylate, glycerol tri-2-ethylhexylate, cetyl-2-ethyl hexanoate and ethylhexyl palminate.

The hydrocarbon oils are, for example, liquid paraffin, ozocerite, squalene, pristane, paraffin, ceresine, vaseline and microcrystalline wax. The higher alcohols are, for example, linear higher alcohols such as lauryl alcohol, cetyl alcohol, stearyl alcohol, behenyl alcohol, myristyl alcohol, oleyl alcohol and cetostearyl alcohol; and branched higher alcohols such as monostearyl glycerol ether (batyl alcohol), 2-decyltetradecinol, lanolin alcohol, hexyldodecanol, isostearyl alcohol and octyldodecanol.

The hair dye can contain humectants such as glycerol, propylene glycol, dipropylene glycol, polyethylene glycol, chondroitin sulfate, hyaluronic acid salts, diglycerol, 1,3-butylene glycol, pyrrolidonecarboxylic acid, sorbitol, maltitol, lactose, oligosaccharides and wheat polypeptides; and silicones such as methylphenylpolysiloxane, dimethylsiloxane/methyl(polyoxyethylene)siloxane copolymers, rubbery dimethylpolysiloxanes and amino-modified polysiloxanes.

The hair dye can contain antioxidants and stabilizers such as thioglycolic acid salts, L-ascorbic acid salts, hydrogensulfites, hydrosulfites and hydrogensulfates; protein hydrolyzates such as collagen hydrolyzate, keratin hydrolyzate, silk protein hydrolyzate, elastin hydrolyzate and soybean protein hydrolyzate, and quaternized products of them. Other amphipathic substances and surfactants are usable as emulsifiers.

The nonionic surfactants include polyoxyethylene surfactants such as polyoxyethylene alkyl ethers, polyoxyethylene fatty acid esters, partial esters of polyoxyethylene/polyhydric alcohols and fatty acids and polyoxyethylene/hardened castor oil derivatives; alkyl polyglycosides such as octyl polyglycosides; polyglycerol surfactants such as polyglycerol fatty acid esters and polyglycerol alkyl ethers; sugar alcohol hydroxyalkyl ethers such as maltitol hydroxyalkyl ether; and fatty acid diethanolamides. The nonionic surfactants may be used in combination with anionic surfactants such as higher fatty acid salts, alkylbenzenesulfonic acid salts, phosphoric esters, alkylsulfuric acid salts, alkylsulfuric ester salts and polyoxyethylene alkylsulfuric ester salts; amino acids; and cationic surfactants such as alkyltrimethylammonium salts, dialkyldimethylammonium salts and alkyldimethylamine oxides.

The hair dye composition can also contain lower alcohols such as ethanol, butanol, propanol, isopropanol and benzyl alcohols; and higher alcohols such as 2-ethylhexyl alcohol, 2-hexyldecyl alcohol, 2-decyltetradecyl alcohol, isostearyl alcohol, cetostearyl alcohol, lauryl alcoho 1, stearyl alcohol and cetyl alcohol. The sequestering agents and antiseptics are, for example, hydroxyethanediphosphonic acid salts, phenacetin, EDTA and salts thereof, parabens and stannates. The high-molecular compounds are, for example, cationic polymers such as poly(dimethylallylammonium halide), polyethylene glycol, epichlorohydrin, propyleneamine, cationic high-molecular compounds which are condensation products of talloyl amines obtained from beef tallow fatty acids, polyethylene glycol, epichlorohydrin, cationic high-molecular compounds which are condensation products of propyleneamine and coconut oil fatty acids, vinylpyrrolidone, cationic high-molecular compounds of dimethylamino methacrylate copolymer type, and cationic high-molecular compounds of quaternary nitrogen-containing cellulose ether type.

The hair dye composition can also contain a thickening agent selected from among lauric acid diethanolamide, carboxymethylcellulose, carboxyvinyl polymers, hydroxyethylcellulose, hydroxypropylcellulose, methylcellulose, xanthane gum, carrageenan, alginic acid salts, pectin, feseran, gum arabic, gatch gum, Karaya gum, tragacanth gum, agar powder, bentonite and crosslinking polyacrylic acid salts.

It is also preferred that the hair dye composition of the present invention contains a pH regulator selected from among hydrochloric acid, sulfuric acid, nitric acid, phosphoric acid, pyrophosphoric acid, acetic acid, lactic acid, citric acid, succinic acid, tartaric acid, malic acid, levulinic acid, and sodium, potassium or ammonium salts of them, pigments and perfumes.

The hair dye composition of the present invention may be of one-pack type, two-pack type comprising the first pack containing an oxidation color and the second pack containing an oxidizing agent, or poly-pack type. This composition can be in any state suitable for dyeing keratin fibers, particularly human hair, such as liquid, cream or gel. It is preferred to store the composition in the form of a powder and to add water to form a fluid, cream, gel or the like at the time of the use. It is also preferred to keep the composition in an aerosol vessel together with a propellant.

EXAMPLES

The following Examples will further illustrate the present invention, which by no means limit the invention.

Example 1

(Sample No. 1)

|  | wt. % |
|---|---|
| p-Toluenediamine sulfate | 10.0 |
| p-Aminophenol | 3.0 |
| 5-Amino-2-methylphenol | 1.0 |
| Resorcinol | 2.0 |
| Sodium percarbonate | 40.0 |
| Diammonium hydrogenphosphate | 15.0 |
| Chlorostearyl trimethylammonium | 2.0 |
| Disodium edetate | 0.2 |
| Xantham gum | 6.5 |
| Sodium carboxymethyl cellulose | 20.0 |
| Perfume | 0.3. |

Sample Nos. 2 to 22 were prepared in the same manner as that described above except that p-toluenediamine sulfate was replaced by an equimolar amount of a compound shown in (Table 1). (Tests on dyeing properties and shampooing resistance)

1. Evaluation of Dyeing Properties:

80 ml of water was added to 20 g of each of sample Nos. 1 to 18 and they were mixed together to obtain a hair-dyeing fluid. This fluid was applied to a bundle of human hair streaked with gray hair, left to stand at room temperature for 30 minutes and shampooed. The bundle of human hair thus dyed was macroscopically observed, and the dyeing properties of the sample were evaluated according to the following criteria:

⊚: Hair dyed natural dark brown, and gray hair was substantially completely covered.
◯: Although hair dyed natural dark brown, gray hair was observed a little.
Δ: Hair dyed brown and gray hair was noticeable to some extent.
X: Hair dyed light brown and gray hair was noticeable.

2. Evaluation of Shampoo Resistance:

After the completion of the evaluation of the dyeing properties, each bundle was divided into two equal parts. One of them was washed by rubbing ten times by hands in a commercial shampoo solution and then dried. This procedure was repeated ten times. The washed bundle was macroscopically compared with the unwashed bundle by placing them side by side. The shampoo resistance was evaluated according to the following criteria:

⊚: Hair was not faded at all.
◯: Hair was slightly faded.
Δ: Hair was apparently faded.
X: Hair was seriously faded.

(Tests of spreadabillity/applicability and level-dyeing properties)

Hair of ten panelists was dyed with sample Nos. 1 to 18, and the spreadabillity/applicability and level-dyeing properties of each sample in the course of dyeing hair were evaluated according to the following criteria:

3. Spreadability and Applicability:

⊙: The sample had an extremely high spreadability and was easily applicable.

○: The sample had a high spreadability and was easily applicable.

Δ: The spreadability of the sample was not so high and it was not easily applicable.

X: The spreadability of the sample was low and it could not be evenly applied.

4. Level-Dyeing Properties:

⊙: Hair was evenly dyed.
○: Hair was almost evenly dyed.
Δ: Hair was almost unevenly dyed.
X: Unevenness of dyeing hair was serious.

TABLE 1

| Sample No. | Compound | Dyeing property | Spreadability applicability | Level-dyeing | Shampoo resistance | Remarks |
|---|---|---|---|---|---|---|
| 1 | p-Toluene diamine sulfate | ○ | ○ | ○ | ○ | Comp. Ex. |
| 2 | Compd. A-1 | ⊙ | ○ | ⊙ | ○ | Ex. of the present invention |
| 3 | Compd. A-4 | ⊙ | ○ | ⊙ | ○ | Ex. of the present invention |
| 4 | Compd. A-5 | ○ | ○ | ○ | ⊙ | Ex. of the present invention |
| 5 | Compd. A-8 | ⊙ | ○ | ⊙ | ○ | Ex. of the present invention |
| 6 | Compd. A-30 | ⊙ | ○ | ○ | ⊙ | Ex. of the present invention |
| 7 | Compd. A-25 | ⊙ | ○ | ○ | ○ | Ex. of the present invention |
| 8 | Compd. A-26 | ⊙ | ⊙ | ○ | ○ | Ex. of the present invention |
| 9 | Compd. A-31 | ⊙ | ⊙ | ⊙ | ⊙ | Ex. of the present invention |
| 10 | Compd. A-32 | ⊙ | ⊙ | ⊙ | ⊙ | Ex. of the present invention |
| 11 | Compd. A-33 | ⊙ | ⊙ | ⊙ | ⊙ | Ex. of the present invention |
| 12 | Compd. A-34 | ⊙ | ⊙ | ⊙ | ⊙ | Ex. of the present invention |
| 13 | Compd. A-35 | ⊙ | ⊙ | ⊙ | ⊙ | Ex. of the present invention |
| 14 | Compd. A-37 | ⊙ | ⊙ | ⊙ | ⊙ | Ex. of the present invention |
| 15 | Compd. A-39 | ⊙ | ○ | ⊙ | ○ | Ex. of the present invention |
| 16 | Compd. A-43 | ⊙ | ⊙ | ⊙ | ⊙ | Ex. of the present invention |
| 17 | Compd. A-46 | ⊙ | ⊙ | ⊙ | ⊙ | Ex. of the present invention |
| 18 | Compd. A-52 | ⊙ | ⊙ | ⊙ | ⊙ | Ex. of the present invention |
| 19 | Comp. compd.-1 | ○ | Δ | Δ | ○ | comp. ex. |
| 20 | Comp. compd.-2 | Δ | Δ | X | X | " |
| 21 | Comp. compd.-3 | Δ | Δ | Δ | X | " |

TABLE 1-continued

| Sample No. | Compound | Dyeing property | Spreadability applicability | Level-dyeing | Shampoo resistance | Remarks |
|---|---|---|---|---|---|---|
| 22 | Comp. compd.-4 | Δ | X | X | X | " |

Comparative Compound-1

Comparative Compound-2

Comparative Compound-3

Comparative Compound-4

The results are summarized in Table 1. It is understood from Table 1 that the compounds of the present invention have very good dyeing properties, excellent spreadability/applicability and level-dyeing properties and a high shampoo resistance. These excellent results could not be obtained prior to the present invention and could not be expected from the prior technique.

Example 2

| | wt. % |
|---|---|
| Example compound (4–32) | 25.0 |
| p-Aminophenol | 4.0 |
| m-Phenylenediamine sulfate | 0.5 |
| Resorcinol | 3.0 |
| 2-Nitro-p-phenylenediamine | 1.0 |
| Sodium perborate | 30.0 |
| Sodium laurylsulfate | 8.0 |
| Hydroxyethyl cellulose/hydroxypropyl trimethylammonium chloride ether | 2.0 |

-continued

| | wt. % |
|---|---|
| Edetic acid | 0.2 |
| Xantham gum | 6.0 |
| Hydroxyethyl cellulose | 20.0 |
| Perfume | 0.3 |

100 ml of water was added to 30 g of the powder hair dye having the above-described composition, and they were mixed together to obtain a hair-dyeing fluid. This fluid was applied to a bundle of human hair streaked with gray hair, left to stand at room temperature for 20 minutes and shampooed. The bundle of human hair was dyed natural dark brown, and gray hair was substantially completely covered. The shampoo resistance was good. After leaving the dyed hair at 60° C. for two weeks, the stability was still excellent.

Example 3

Hair dye compositions were prepared in the same manner as that of Example 2 except that the example compound (A-32) was replaced with an equimolar amount of example compound (A-3), (A-15), (A-25), (A-27), (A-30) or (A-39). The same test as that of Example 2 was repeated to prove that the dyeing properties and shampoo resistance were excellent.

Example 4

Hair dye compositions were prepared in the same manner as that of Example 2 except that the example compound (A-32) was replaced with an equimolar amount of example compound (A-13), (A-46) or (A-52). The same test as that of Example 2 was repeated to prove that each hair dye composition realized a natural dark brown color, had excellent dyeing properties and a high safety and did not irritate the scalp.

Example 5

Hair dye compositions were prepared in the same manner as that of Example 2 except that the example compound (A-32) was replaced with an equimolar amount of example compound (A-6), (A-9), (A-22), (A-35), (A-37) or (A-41). The same test as that of Example 2 was repeated to prove that each hair dye composition (oxidation color) had excellent dyeing properties and realized a comfortable feeling upon use, and the dyed hair was smooth and could be easily brushed.

Example 6

The hair-dyeing properties were evaluated in the same manner as that of Example 1 except that compounds shown in Table 2 were used. The results are summarized in Table 2.

TABLE 2

| Sample No. | Compound | Dyeing property | Spreadability applicability | Level-dyeing | Shampoo resistance | Remarks |
|---|---|---|---|---|---|---|
| 1 | p-Toluene diamine sulfate | ○ | ○ | ○ | ○ | Comp. Ex. |
| 2 | Compd. $A_2$-1 | ⊙ | ⊙ | ⊙ | ⊙ | Ex. of the present invention |
| 3 | Compd. $A_2$-2 | ⊙ | ⊙ | ⊙ | ○ | Ex. of the present invention |
| 4 | Compd. $A_2$-3 | ⊙ | ⊙ | ⊙ | ⊙ | Ex. of the present invention |
| 5 | Compd. $A_2$-14 | ⊙ | ⊙ | ⊙ | ⊙ | Ex. of the present invention |
| 6 | Compd. $A_2$-15 | ⊙ | ○ | ○ | ⊙ | Ex. of the present invention |
| 7 | Compd. $A_2$-17 | ⊙ | ⊙ | ⊙ | ⊙ | Ex. of the present invention |
| 8 | Compd. $A_2$-19 | ○ | ⊙ | ⊙ | ⊙ | Ex. of the present invention |
| 9 | Compd. $A_2$-37 | ⊙ | ⊙ | ⊙ | ⊙ | Ex. of the present invention |
| 10 | Compd. $A_2$-38 | ⊙ | ⊙ | ⊙ | ⊙ | Ex. of the present invention |
| 11 | Compd. $A_2$-43 | ⊙ | ⊙ | ⊙ | ⊙ | Ex. of the present invention |
| 12 | Compd. $A_2$-44 | ⊙ | ⊙ | ⊙ | ⊙ | Ex. of the present invention |
| 13 | Comp. compd.-21 | X | Δ | Δ | Δ | Comp. ex. |
| 14 | Comp. compd.-22 | X | Δ | Δ | Δ | " |

Comparative Compound-21

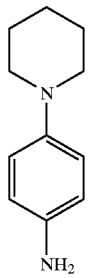

Comparative Compound-22

TABLE 2-continued

| Sample No. | Compound | Dyeing property | Spreadability applicability | Level-dyeing | Shampoo resistance | Remarks |
|---|---|---|---|---|---|---|
| | H-N(CH₂CH₂O)₂H on phenyl-NH₂ | | | | | |

It is understood from Table 2 that the compounds of the present invention had excellent dyeing properties, spreadability/applicability and level-dyeing properties and had a high shampoo resistance. These excellent results could not be obtained prior to the present invention and could not be expected from the prior technique.

Example 7

The tests were conducted in the same manner as that of Example 2 except that the compound used in Example 2 was replaced with example compound ($A_2$-38). Excellent results similar to those of Example 2 were obtained.

Example 8

Hair dye compositions were prepared in the same manner as that of Example 7 except that the example compound ($A_2$-38) was replaced with an equimolar amount of example compound ($A_2$-3), ($A_2$-5), ($A_2$-16), ($A_2$-18), ($A_2$-31) or ($A_2$-42). The same test as that of Example 7 was repeated to prove that the dyeing properties and shampoo resistance thereof were excellent.

Example 9

Hair dye compositions were prepared in the same manner as that of Example 7 except that the example compound ($A_2$-38) was replaced with an equimolar amount of example compound ($A_2$-10), ($A_2$-19), ($A_2$-24) or ($A_2$-30). The same test as that of Example 7 was repeated to prove that dyed hair could be easily bound together. A pleasant feeling was realized upon use.

Example 10

Hair dye compositions were prepared in the same manner as that of Example 7 except that the example compound ($A_2$-38) was replaced with an equimolar amount of example compound ($A_2$-36), ($A_2$-39), ($A_2$-40) or ($A_2$-43). The same test as that of Example 7 was repeated to prove that each hair dye composition was safe and did not irritate the scalp.

Example 11

The hair-dyeing properties were evaluated in the same manner as that of Example 1 except that compounds shown in Table 3 were used. The results are summarized in Table 3.

TABLE 3

| Sample No. | Compound | Dyeing property | Spreadability applicability | Level-dyeing | Shampoo resistance | Remarks |
|---|---|---|---|---|---|---|
| 1 | p-Toluene diamine sulfate | ○ | ○ | ○ | ○ | Comp. Ex. |
| 2 | Compd. $A_4$-2 | ⊙ | ⊙ | ⊙ | ○ | Ex. of the present invention |
| 3 | Compd. $A_4$-4 | ⊙ | ⊙ | ⊙ | ○ | Ex. of the present invention |
| 4 | Compd. $A_4$-7 | ⊙ | ⊙ | ⊙ | ⊙ | Ex. of the present invention |
| 5 | Compd. $A_4$-18 | ⊙ | ⊙ | ⊙ | ⊙ | Ex. of the present invention |
| 6 | Compd. $A_4$-22 | ○ | ⊙ | ⊙ | ○ | Ex. of the present invention |
| 7 | Compd. $A_4$-25 | ⊙ | ⊙ | ⊙ | ○ | Ex. of the present invention |

TABLE 3-continued

| Sample No. | Compound | Dyeing property | Spreadability applicability | Level-dyeing | Shampoo resistance | Remarks |
|---|---|---|---|---|---|---|
| 8 | Compd. $A_4$-33 | ◉ | ◉ | ◉ | ◉ | Ex. of the present invention |
| 9 | Compd. $A_4$-34 | ◉ | ◉ | ◉ | ◉ | Ex. of the present invention |
| 10 | Comp. compd.-41 | X | Δ | Δ | X | Ex. of the present invention |
| 11 | Comp. compd.-42 | X | Δ | Δ | Δ | Ex. of the present invention |
| 12 | Comp. compd.-43 | X | Δ | Δ | X | Ex. of the present invention |

Comparative Compound-41

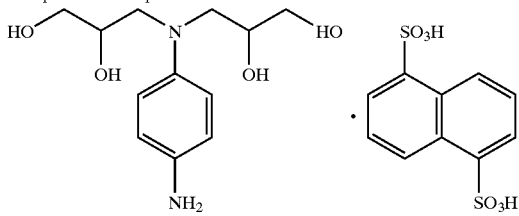

Comparative Compound-42

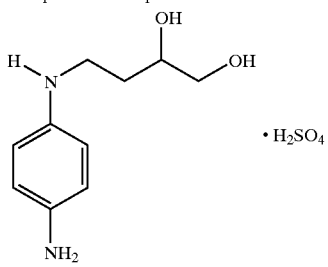

Comparative Compound-43

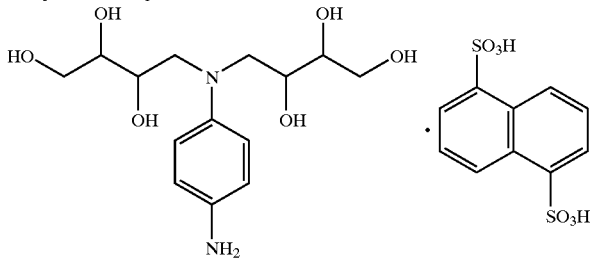

It is understood from Table 3 that the compounds of the present invention had excellent dyeing properties, spreadability/applicability and level-dyeing properties and had a high shampoo resistance. These excellent results could not be obtained prior to the present invention and could not be expected from the prior technique.

Example 12

The tests were conducted in the same manner as that of Example 2 except that the compound used in Example 2 was replaced with example compound ($A_4$-7). Excellent results similar to those of Example 2 were obtained.

Example 13

Hair dye compositions were prepared in the same manner as that of Example 12 except that the example compound ($A_4$-7) was replaced with example compound ($A_4$-6), ($A_4$-18), ($A_4$-24) or ($A_4$-33). The same test as that of Example 12 was repeated to prove that the composition had excellent dyeing properties and shampoo resistance.

Example 14

Hair dye compositions were prepared in the same manner as that of Example 12 except that the example compound ($A_4$-7) was replaced with an equimolar amount of example compound ($A_4$-21), ($A_4$-29), ($A_4$-31), ($A_4$-32), ($A_4$-34) or ($A_4$-36). The same test as that of Example 12 was repeated to prove that each hair dye composition had excellent dyeing properties, shampoo resistance and safety and did not irritate the scalp.

Thus, according to the present invention, a hair dye composition having excellent dyeing properties, spreadability/applicability and level-dyeing properties in the hair dyeing process and excellent shampoo resistance can be obtained.

What is claimed is:

1. A method for dyeing hair which comprises a step of applying to the hair a hair dye composition containing a compound of the following formula (I):

$$\text{(I)}$$

wherein in formula (I),
- $R_1$ represents 2-methanesulfonamidoethyl, 3,4-dihydroxybutyl, 2,3,4,5,6-pentahydroxyhexyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-[2-(2-[2-(2-hydroxyethoxy)ethoxy]ethoxy)ethoxy]ethyl, 2-(2-[2-(2-[2-(2-hydroxyethoxy)ethoxy]ethoxy)ethoxy]ethoxy)ethyl, 2-(2-[2-(2-[2-(2-[2-(2-hydroxyethoxy)ethoxy]ethoxy)ethoxy]ethoxy)ethoxy]ethoxy)ethyl, methoxyethoxy)ethoxy]ethyl, 2-(2-(2-butoxyethoxy)ethoxy]ethyl, mercaptoethyl, pyrimidinyl, carboxymethyl, 2-carbamoylaminoethyl, sulfopropyl or 2-bromoethyl group,
- $R_2$ represents a halogen atom or a substituted or unsubstituted substituent selected from the group consisting of an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups;
- Z represents a trimethylene group, with the proviso that at least one of $R_1$ and Z is substituted by a substituent containing at least one of nitrogen atom, oxygen atom and sulfur atom when $R_1$ is an alkyl or aryl group;
- n represents 0 or an integer of 1 to 3, with the proviso that $R_2$'s are optionally the same or different or they optionally form a ring when n is 2 or higher;
- A represents an acid radical and A-H is an acid; and m represents 0 or a positive integer.

2. The method according to claim 1, wherein in formula (I),
- $R_2$ represents a substituent selected from the group consisting of halogen atoms and alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups; and
- Z represents a trimethylene group unsubstituted or substituted with a hydroxyl, alkyl or carboxyl group, which has 2 to 30 carbon atoms in total, with the proviso that at least one of $R_1$ and Z is substituted by a substituent containing at least one of nitrogen atom, oxygen atom and sulfur atom when $R_1$ is an alkyl or aryl group.

3. The method according to claim 2, where
- $R_2$ represent a substituent selected from the group consisting of methyl, i-propyl, methoxy, chlorine, and 2,3-dihydroxypropyl, or two $R_2$'s together form a furan ring;
- Z represents a trimethylene group unsubstituted or substituted with a hyroxyl, alkyl or carboxyl group, which has 2 to 6 carbon atoms in total, with the proviso that at least one of $R_1$ and Z is substituted by a substituent containing at least one of nitrogen atom, oxygen atom and sulfur atom;
- n represents 0 or an integer of 1 or 2, with the proviso that $R_2$'s may be the same or different or they may form a ring when n is 2;
- A-H is an acid selected from the group consisting of hydrochloric acid, sulfuric acid, p-toluenesulfonic acid and naphthalene-1,5-disulfonic acid; and
- m represents an integer of 1 to 3.

4. The method according to claim 1, wherein $R_1$ represents 3,4-dihydroxybutyl, 2,3,4,5,6-pentahydroxyhexyl, 2-(2-hydroxyethoxy)ethyl, 2-[2-(2-hydroxyethoxy)ethoxy]ethyl, 2-(2-[2-(2-hydroxyethoxy)ethoxy]ethoxy)ethyl, 2-(2-[2-(2-[2-(2-hydroxyethoxy)ethoxy]ethoxy)ethoxy]ethoxy)ethyl or mercaptoethyl.

5. A method for dyeing hair which comprises a step of applying to the hair a hair dye composition containing at least one of the compounds of the following formulae (II) or (III)

$$\text{(II)}$$

$$\text{(III)}$$

wherein in formula (II),
- $R_{11}$ represents a halogen atom or a substituted or unsubstituted substituent selected from the group consisting of an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups;
- Y represents a tetramethylene, pentamethylene or hexamethylene group substituted by a substituent containing at least one of carbon atom, nitrogen atom, oxygen atom and sulfur atom;

$n_1$ represents 0 or an integer of 1 to 4, with the proviso that $R_{11}$'s are optionally the same or different or they optionally form a ring when $n_1$ is 2 or higher;

a part of Y and $R_{11}$ do not form a ring together;

$A_1$ represents an acid radical and $A_1$-H is an acid; and $m_1$ represents 0 or a positive integer, wherein in formula (III), $R_{21}$ represents an alkyl, aryl or heterocyclic group;

$R_{22}$ represents a hydrogen atom or an alkyl, aryl or heterocyclic group;

$R_{23}$ represents a halogen atom or a substituted or unsubstituted substituent selected from the group consisting of an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups;

$n_{21}$ represents an integer of 2 to 8;

$n_{22}$ represents 0 or an integer of 1 to 4, with the proviso that $R_{23}$'s are optionally the same or different or together form a ring when $n_{22}$ is 2 or higher;

$R_{21}$ does not form a ring with $R_{23}$ and does not have four or more hydroxyl groups in the molecule;

$A_2$ represents an acid radical and $A_2$-H is an acid; and $m_2$ represents 0 or a positive integer.

6. A method for dyeing hair which comprises a step of applying to the hair a hair dye composition containing at least one of the compounds of the following formulae (IV) or (V):

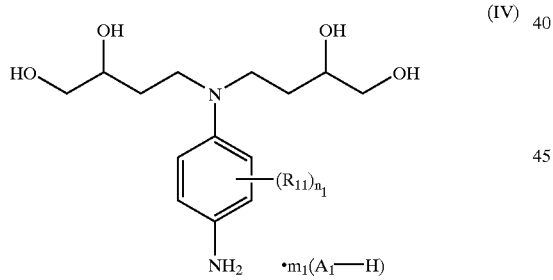

(IV)

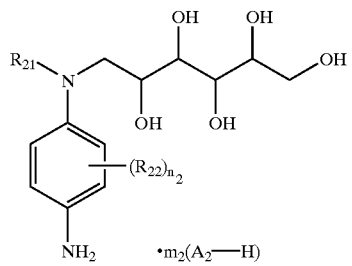

(V)

wherein in formula (IV), $R_{41}$ represents a halogen atom or a substituted or unsubstituted substituent selected from the group consisting of an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups;

$n_{41}$ represents 0 or an integer of 1 to 4, with the proviso that $R_{41}$'s are optionally the same or different or together form a ring when $n_{41}$ is 2 or higher;

$A_{41}$ represents an acid radical and $A_{41}$-H is an acid; and $m_{41}$ represents 0 or a positive integer, wherein in formula (V), $R_{51}$ represents a hydrogen atom or an alkyl, aryl or heterocyclic group;

$R_{52}$ represents a halogen atom or a substituted or unsubstituted substituent selected from the group consisting of an alkyl, aryl, heterocyclic, cyano, nitro, hydroxyl, carboxyl, sulfo, alkoxyl, aryloxy, acylamino, amino, alkylamino, anilino, ureido, sulfamoylamino, alkylthio, arylthio, alkoxycarbonylamino, sulfonamido, carbamoyl, sulfamoyl, sulfonyl, alkoxycarbonyl, heterocyclic oxy, azo, acyloxy, carbamoyloxy, silyl, silyloxy, aryloxycarbonylamino, imido, heterocyclic thio, sulfinyl, phosphonyl, aryloxycarbonyl, acyl and mercapto groups;

$n_{51}$ represents 0 or an integer of 1 to 4, with the proviso that $R_{52}$'s are optionally the same or different or together form a ring when $n_{51}$ is 2 or higher;

$R_{51}$ does not form a ring with $R_{52}$;

$A_{51}$ represents an acid radical and $A_{51}$-H is an acid; and $m_{51}$ represents 0 or a positive integer.

\* \* \* \* \*